United States Patent
Ney et al.

(10) Patent No.: US 8,604,168 B2
(45) Date of Patent: Dec. 10, 2013

(54) GLYCOMACROPEPTIDE MEDICAL FOODS FOR NUTRITIONAL MANAGEMENT OF PHENYLKETONURIA AND OTHER METABOLIC DISORDERS

(75) Inventors: Denise M. Ney, Brooklyn, WI (US); Mark R. Etzel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 361 days.

(21) Appl. No.: 12/813,988

(22) Filed: Jun. 11, 2010

(65) Prior Publication Data

US 2010/0317597 A1   Dec. 16, 2010

Related U.S. Application Data

(60) Provisional application No. 61/186,690, filed on Jun. 12, 2009.

(51) Int. Cl.
*A61K 38/16* (2006.01)
*A61K 35/20* (2006.01)

(52) U.S. Cl.
USPC ............ 530/360; 530/395; 514/5.5; 562/575; 562/560

(58) Field of Classification Search
USPC .................................. 530/360, 395; 514/5.5
See application file for complete search history.

(56) References Cited

U.S. PATENT DOCUMENTS 5,968,586 A   10/1999  Etzel
6,168,823 B1   1/2001  Etzel

FOREIGN PATENT DOCUMENTS

WO   98/08402   5/1998

OTHER PUBLICATIONS

Reyes, A. A., (J. Am. Soc. Nephrol. 4:1039-1045, 1993).*
World Health Organization, Protein and Amino Acid Requirements in Human Nutrition, Geneva Switzerland: United Nations University, 2007.
Turner et al., "Total sulfur amino acid requirement of healthy school-aged children as determined by indicator amino acid oxidation technique" 2006 Am J Clin Nutr. 83:619-23.
Norton et al., "The leucine content of a complete meal directs peak activation but not duration of skeletal muscle protein synthesis and mammalian target of rapamycin signaling in rats" 2009 J Nutr 139:1103-1109.
Ney et al., "Dietary Glycomacropeptide Supports Growth and Reduces the Concentrations of Phenylalanine in Plasma and Brain in a Murine Model of Phenylketonuria" 2008 J. Nutr. 138: 316-322.
Lim et al. Acceptable low-phenylalanine foods and beverages can be made with glycomacropeptide from cheese whey for individuals with PKU, Molecular Genetics and Metabolism 92 (2007) 176-178.
Crozier et al., "Oral Leucine Administration Stimulates Protein Synthesis in Rat Skeletal Muscle" 2005 J Nutr 135:376-382.
Ball et al., "The in vivo sparing of methionine by cysteine in sulfur amino acid requirements in animal models and adult humans" 2006 J Nutr. 136:1682S-93S.
Institute of Medicine, Chapter 10: Proteins and Amino Acids; in Dietary Reference Intakes for Energy, Carbohydrates, Fiber, Fat, Protein and Amino Acids, Washington DC: National Academy Press, 2002.

* cited by examiner

*Primary Examiner* — David Lukton
(74) *Attorney, Agent, or Firm* — Quarles & Brady, LLP

(57) ABSTRACT

Medical foods containing glycomacroprotein and additional supplemented amounts of arginine, leucine, and optionally other amino acids, such as tyrosine, are disclosed. The medical foods can be used to provide the complete protein requirements for patients having metabolic disorders such as phenylketonuria.

42 Claims, 13 Drawing Sheets

GLYCOMACROPEPTIDE MEDICAL FOODS FOR NUTRITIONAL MANAGEMENT OF PHENYLKETONURIA AND OTHER METABOLIC DISORDERS

CROSS-REFERENCE TO RELATED APPLICATION

This application claims the benefit of U.S. Provisional Application No. 61/186,690, filed on Jun. 12, 2009, which is incorporated by reference herein in its entirety.

STATEMENT REGARDING FEDERALLY SPONSORED RESEARCH OR DEVELOPMENT

This invention was made with government support under DK071534 awarded by the National Institutes of Health. The government has certain rights in the invention.

FIELD OF THE INVENTION

This invention relates generally to medical foods used for the nutritional management of metabolic disorders such as phenylketonuria. In particular, the present invention is directed to medical foods containing glycomacropeptide as a primary protein source supplemented with additional amounts of the amino acids arginine, leucine, and tyrosine.

BACKGROUND OF THE INVENTION

Phenylalanine (Phe) is an indispensable amino acid that is converted to tyrosine by the enzyme phenylalanine hydroxylase (PAH; EC 1.14.16.1) in an individual with normal metabolism. About 1 in every 15,000 infants born annually have absent or impaired function of this enzyme and are diagnosed with the metabolic disorder phenylketonuria (PKU) (Scriver C. R. 2001, The Metabolic & Molecular Bases of Inherited disease, 8th ed. New York: McGraw-Hill). If the diet of an individual with PKU is not modified within the first 20 days of life, Phe and its breakdown products accumulate in the blood and brain, causing neurological damage and cognitive disability.

Dietary management of PKU requires a low-Phe diet, suggested for life. Foods such as meat, dairy, legumes, and bread must be avoided by individuals with PKU because of the high Phe content. Although some low-protein natural foods are allowed in the low-Phe diet (mainly certain fruits and vegetables), the majority of dietary protein in the standard PKU diet is typically supplied by a Phe-free amino acid formula. A daily tally of total Phe consumption for adults older than 19 years of age must not exceed a target value from 220 to 770 mg/day for females or 290 to 1,200 mg/day for males (Acosta P & Yanicelli S. 2001, Protocol 1-Phenylketonuria (PKU), in Division, R. P., (editor), The Ross Metabolic Formula System Nutrition Support Protocols. 4th ed.: Ross Product Division).

The standard amino acid formula-based diet for PKU is difficult to follow, restrictive, and unpalatable. Non-compliance, a common problem with the standard PKU diet, can cause severe neuropsychological impairment. Thus, there is a need in the art for medical foods that are more palatable than the standard amino-acid based formulas and that provide PKU patients with necessary protein, including essential amino acids, while effectively maintaining low Phe levels in the blood and brain.

SUMMARY OF THE INVENTION

The present invention provides medical foods designed to increase dietary compliance and quality of life for individuals with metabolic disorders such as PKU. In one aspect, the invention encompasses medical foods for the management of a metabolic disorder. Such foods contain glycomacropeptide (GMP) and additional supplemented amounts of certain amino acids, including arginine and leucine. Preferably, the weight ratio within the medical foods of the amino acid arginine to the total protein is from about 60 to 90 milligrams arginine/gram total protein; more preferably, the weight ratio is about 75 milligrams arginine/gram total protein. Preferably, the weight ratio within the medical foods of the amino acid leucine to the total protein is from about 100 to 200 milligrams leucine/gram total protein; more preferably, about 100 milligrams leucine/gram total protein.

In certain embodiments, the medical foods additionally contain a supplemented amount of the amino acid tyrosine. Preferably, the weight ratio within the medical foods of the amino acid tyrosine to the total protein is from about 62 to 93 milligrams tyrosine/gram total protein; more preferably, about 85 milligrams tyrosine/gram total protein.

In some embodiments, the total weight of the additional supplemented amino acids within the medical foods is from about 22% to 38% of the total weight of the protein from GMP and the supplemented amino acids together. The foods may be additionally supplemented with other amino acids, including without limitation histidine and tryptophan. Preferably, in embodiments further containing supplemented amounts of the amino acids tryptophan and histidine, the total weight of the additional supplemental amino acids is from about 25% to 42% of the total weight of the protein from the GMP and the supplemented amino acids together. Optionally, the medical food is not additionally supplemented with the amino acid methionine.

In certain embodiments, the medical foods encompassed by the invention may be targeted to specific metabolic disorders by varying the preferred combination of additional supplemental amino acids contained in the foods. For example, for the management of a phenylalanine metabolism disorders such as phenylketonuria, the foods preferably contain supplemental amounts of the amino acids arginine, leucine, and tyrosine in addition to the GMP. However, for the management of tyrosine metabolism disorders such as tyrosinemia, the foods would not contain any supplemental amount of tyrosine.

The medical foods encompassed by the invention may be in the form of a variety of standard food products. Preferred forms include beverages, bars, wafers, puddings, gelatins, crackers, fruit leathers, nut butters, sauces, salad dressings, crisp cereal pieces, flakes, puffs, a pellets, or extruded solids.

In certain embodiments, the medical foods may be heat-treated during production, such as, for example, by baking the foods. The inventors have determined that during heat treatment, amino acid levels may decrease; particularly the amino acid levels of any added tryptophan, tyrosine, histidine, leucine, or arginine. Accordingly, in some such embodiments, the amount of initial additional supplemental amino acids used to make the medical foods is higher than for foods that are not heat-treated, so that the final weight ratio falls within the preferred ranges. As non-limiting examples, in preferred embodiments, the initial weight ratio of the amino acid tryptophan to total protein within the medical food before heat treatment is greater than about 12 milligrams tryptophan/gram total protein, the initial weight ratio of the amino acid tyrosine to total protein within the medical food before heat treatment is greater than about 85 milligrams tyrosine/gram total protein, the initial weight ratio of the amino acid histidine to total protein within the medical food before heat treatment may be greater than about 23 milligrams histidine/ gram total protein, the initial weight ratio of the amino acid leucine to total protein within the medical food before heat treatment is greater than about 100 milligrams leucine/gram total protein, and/or the initial weight ratio of the amino acid arginine to total protein within the medical food before heat treatment is greater than about 75 milligrams arginine/gram total protein.

In such exemplary embodiments, the initial amino acid levels within the medical foods may be such that the final weight ratio of the amino acid tryptophan to total protein within the medical food after heat treatment is from about 12 to 14 milligrams tryptophan/gram total protein, the final weight ratio of the amino acid tyrosine to total protein within the medical food after heat treatment is from about 62 to 93 milligrams tyrosine/gram total protein, the final weight ratio of the amino acid histidine to total protein within the medical food after heat treatment is from about 20 to 24 milligrams histidine/gram total protein, the final weight ratio of the amino acid leucine to total protein within the medical food after heat treatment is from about 100 to 200 milligrams leucine/gram total protein, and/or the final weight ratio of the amino acid arginine to total protein within the medical food after heat treatment is from about 60 to 90 milligrams arginine/gram total protein.

The medical foods of the invention that are used in a PKU management diet must contain very low phenylalanine levels. Accordingly, in certain preferred embodiments, the GMP included in the medical foods contains not more than 2.0 milligrams phenylalanine contaminant per gram GMP protein. Although GMP of such purity may be provided by a commercial vendor, in certain such embodiments, the GMP may be purified before it is included in the medical food. Because of the addition of supplemental amounts of amino acids to the foods that are not present in purified GMP, in certain preferred embodiments, the medical food of the inventions contains less than 1.5 milligrams phenylalanine per gram total protein. Certain non-protein ingredients, such as chocolate, may contribute trace amounts of phenylalanine to the medical foods; accordingly, in certain embodiments, the medical foods contain from about 1.2 to about 1.8 milligrams phenylalanine per gram total protein.

The medical foods of the invention that are used in managing a tyrosine metabolism disorder must contain very low phenylalanine plus tyrosine levels. Accordingly, such embodiments do not contain supplemented amounts of tyrosine. Preferably, in embodiments for managing a tyrosine metabolism disorder, the medical food contains less than 2.0 milligrams phenylalanine and tyrosine together per gram total protein.

In some embodiments for managing a tyrosine metabolism disorder containing supplemental amounts of the amino acids arginine and leucine, the total weight of the additional supplemented amino acids within the medical foods is from about 16% to 29% of the total weight of the protein from GMP and the supplemented amino acids together. In yet other such embodiments for managing a tyrosine metabolism disorder, in addition to leucine and arginine, the medical foods contain additional supplemented amounts of the amino acids histidine and tryptophan. Preferably, in such embodiments, the total weight of the additional supplemental amino acids is from about 19% to 33% of the total weight of the protein from the GMP and the supplemented amino acids together. To maintain recommend supplementation levels of the other supplemented amino acids in the absence of tyrosine, additional GMP may be added to the medical foods.

In a second aspect, the invention encompasses methods of making the medical foods described previously. The method includes the steps of providing glycomacropeptide (GMP) and additional supplemented amounts of certain amino acids, including arginine and leucine, and mixing the provided materials with one or more non-protein ingredients to make a food. Preferably, the weight ratio of the amino acid arginine provided to the total protein provided is from about 60 to 90 milligrams arginine/gram total protein; more preferably, about 75 milligrams arginine/gram total protein. Preferably, the weight ratio of the amino acid leucine provided to the total protein provided is from about 100 to 200 milligrams leucine/gram total protein; more preferably, the ratio is about 100 milligrams leucine/gram total protein.

In some preferred embodiments of the method, a supplemented amount of the amino acid tyrosine is also provided. Preferably, the weight ratio of the amino acid tyrosine provided to the total protein provided is from about 62 to 93 milligrams tyrosine/gram total protein; more preferably, the ratio is about 85 milligrams tyrosine/gram total protein. In some such embodiments, the total weight of the additional supplemented amino acids is from about 22% to 38% of the total weight of protein from GMP and the supplemented amino acids together.

In certain embodiments, the method encompassed by the invention may be modified to make medical foods targeted to specific metabolic disorders by varying the provided combination of supplemented amino acids. For example, for making medical foods used for the management of a phenylalanine metabolism disorders such as phenylketonuria, supplemental amounts of the amino acids arginine, leucine, and tyrosine in addition to the GMP are provided. However, for the making of medical foods used for the management of tyrosine metabolism disorders such as tyrosinemia, no supplemental amounts of tyrosine would be provided.

In certain preferred embodiments, the method includes the step of purifying the GMP so that it contains no more than 2.0 mg phenylalanine contaminant per gram GMP protein. In some such embodiments, the step of purifying the GMP may be performed by one or more of the following techniques: cation exchange chromatography, ultrafiltration, and diafiltration. Such embodiments may also include an additional step of drying the purified GMP by lyophilization or spray drying.

Certain embodiments may include the additional step of allowing the food to set to form a pudding, gelatin, or fruit leather. Other embodiments may include the step of forming the food into a bar, a cracker, a flake, a puff, or a pellet, or extruding the food as an extruded solid.

Certain embodiments may include the additional step of heat-treating the provided mixture when making the food. A non-limiting example of such a step is baking the food in an oven or other heated chamber. The inventors have determined that certain amino acids, including tyrosine, tryptophan, arginine, leucine, and histidine, are lost or degraded during heat treatment. Accordingly, in such embodiments, it is preferred that the initial amounts of additional supplemental amino acids used to make the medical foods are provided at higher levels than for foods that are not heat-treated, so that as amino acids are lost or degraded through heat treatment, the final weight ratio falls within preferred ranges.

As a non-limiting example, in preferred embodiments, the initial weight ratio of the amino acid tryptophan provided to total protein provided before heat treatment may be greater than about 12 milligrams tryptophan/gram total protein; the initial weight ratio of the amino acid tyrosine provided to the total protein provided before heat treatment may be greater than about 85 milligrams tyrosine/gram total protein; the initial weight ratio of the amino acid histidine provided to total protein provided within the medical food before heat treatment may be greater than about 23 milligrams histidine/gram total protein; the initial weight ratio of the amino acid leucine provided to total protein provided within the medical food before heat treatment may be greater than about 100 milligrams leucine/gram total protein; and/or the initial weight ratio of the amino acid arginine provided to total protein provided before heat treatment may be greater than about 75 milligrams arginine/gram total protein.

During heat treatment, these amino acid levels within the food may decrease. It is preferred that the final weight ratio of the amino acid tryptophan to total protein within the medical food after heat treatment is from about 12 to 14 milligrams tryptophan/gram total protein, the final weight ratio of the amino acid tyrosine to total protein within the medical food after heat treatment is from about 62 to 93 milligrams tyrosine/gram total protein, the final weight ratio of the amino acid histidine to total protein within the medical food after heat treatment is from about 20 to 24 milligrams histidine/gram total protein, the final weight ratio of the amino acid leucine to total protein within the medical food after heat treatment is from about 100 to 200 milligrams leucine/gram total protein, and/or the final weight ratio of the amino acid arginine to total protein within the medical food after heat treatment is from about 60 to 90 milligrams arginine/gram total protein.

In a third aspect, the invention encompasses methods of treating a metabolic disorder, including without limitation a phenylalanine metabolism disorder, a tyrosine metabolism disorder, a tryptophan metabolism disorder, or a histidine metabolism disorder. These methods include the step of administering to a human having a metabolic disorder a medical food containing glycomacropeptide (GMP) and additional supplemented amounts of two or more amino acids, including arginine and leucine. Preferably, the weight ratio within the medical food of the amino acid arginine to the total protein is from about 60 to 90 milligrams arginine/gram total protein; more preferably, the ratio is about 75 milligrams arginine/gram total protein. Preferably, the weight ratio within the medical food of the amino acid leucine to the protein is from about 100 to 200 milligrams leucine/gram total protein; more preferably, about 100 milligrams leucine/gram total protein.

In such embodiments where the medical food is not further supplemented with tyrosine, the human treated with the medical food may have a tyrosine metabolism disorder, including without limitation Type I tyrosinemia, Type II tyrosinemia, Type III tyrosinemia/Hawkinsinuria, or Alkaptonuria/Ochronosis. In such embodiments, the medical food preferably contains less than 2.0 milligrams phenylalanine and tyrosine together per grams total protein.

In yet other embodiments, the administered medical food additionally contains a supplemented amount of the amino acid tyrosine. Preferably, the weight ratio within the medical food of the amino acid tyrosine to the total protein is from about 62 to 93 milligrams tyrosine/gram total protein; more preferably, the ratio is about 85 milligrams tyrosine/gram total protein. In such embodiments, the human treated with the medical food may have a phenylalanine metabolism disorder, including without limitation phenylketonuria (PKU), a tryptophan metabolism disorder, including without limitation hypertryptophanemia, or a histidine metabolism disorder, including without limitation carnosinemia, histidinemia, or urocanic aciduria. In embodiments where a human with a tryptophan metabolism disorder is treated, the administered medical food does not contain supplemented amounts of tryptophan. In embodiments where a human with a histidine metabolism disorder is treated, the administered medical food does not contain supplemented amounts of histidine.

In embodiments where the human being treated has a phenylalanine metabolism disorder, the human is preferably at least two years old. Preferably, the medical food administered contains less than 1.5 milligrams phenylalanine per gram total protein.

These and other features of the present invention will become apparent to the skilled artisan from the following detailed description considered in conjunction with the accompanying drawings.

DETAILED DESCRIPTION OF THE INVENTION

I. In General

Figure 1:
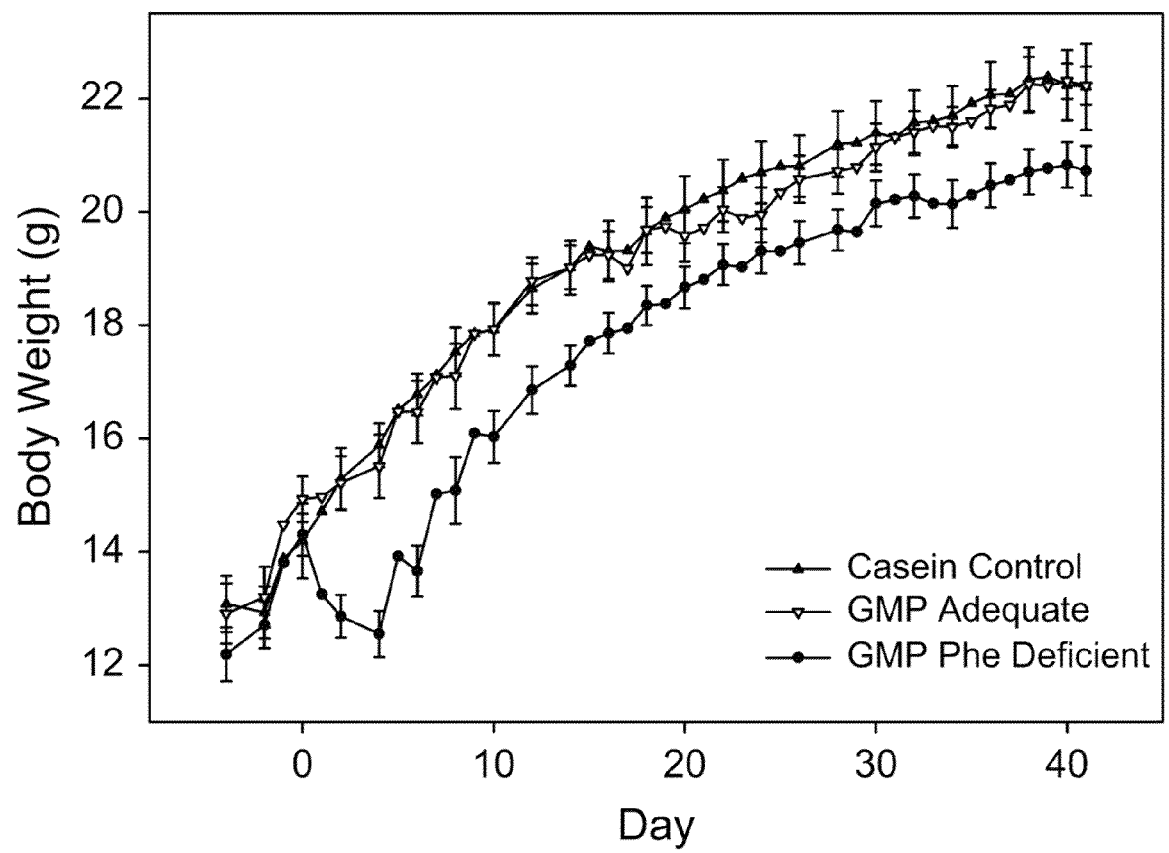
FIG. 1 shows body weight as a function of time in weanling WT mice fed diets containing casein, GMP supplemented with limiting IAA (GMP adequate), or GMP supplemented with limiting IAA except Phe (GMP Phe deficient) over a 42 d. period. Values are means±SEM; n=10. Phe was added to the drinking water for the GMP Phe-deficient group (1 g Phe/L) on d 4 through the end of the study. There were no significant differences for changes in daily BW from d 14 to d 42.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "about" means within a range from 10% below to 10% above a given value.

As used herein, the term "medical food" means "a food which is formulated to be consumed or administered enterally under the supervision of a physician and which is intended for the specific dietary management of a disease or condition for which distinctive nutritional requirements, based on recognized scientific principles, are established by medical evaluation" (from section 5(b) of the Orphan Drug Act, 21 U.S.C. 360ee (b) (3)). Medical foods are distinguished from the broader category of foods for special dietary use and from foods that make health claims by the requirement that medical foods be intended to meet distinctive nutritional requirements of a disease or condition, used under medical supervision and intended for the specific dietary management of a disease or condition.

The term "medical foods" does not pertain to all foods fed to sick patients. Medical foods are foods that are specially formulated and processed (as opposed to a naturally occurring foodstuff used in a natural state) for the patient who is seriously ill or who requires the product as a major treatment modality. To be considered a medical food, a product must, at a minimum, meet the following criteria: the product must be a food for oral or tube feeding; the product must be labeled for the dietary management of a specific medical disorder, disease, or condition for which there are distinctive nutritional requirements; and the product must be intended to be used under medical supervision (from U.S. Food and Drug Administration, Guidance for Industry: Frequently Asked Questions About Medical Foods, Center for Food Safety and Applied Nutrition, May 2007).

As used herein, a "supplemented amount" of an amino acid refers to the quantity of amino acid that is added to a mixture or contained in a food that does not come from (a) trace contamination of the GMP protein, or (b) trace amounts of amino acids contained in non-protein products. A non-limiting example of a non-protein product is chocolate, which has trace amounts of Phe, but is not recognized a s a significant source of protein or amino acids. Supplemented amounts may come from any other source that is recognized as containing significant amounts of a given amino acid or protein containing the amino acid, including without limitation commercial amino acid supplements.

As used herein, "total protein" within a food means the aggregate of the protein from the GMP within the food and the protein from additional supplemented amino acids within the food.

The following abbreviations are used throughout the present disclosure: AA, amino acid; Ala, alanine; Arg, arginine; Asn, asparagine; Asp, aspartic acid; BW, body weight; Cys, cysteine; DRI, dietary reference intakes; Gln, glutamine; Glu, glutamic acid; Gly, glycine; GMP, glycomacropeptide; His, histidine; IAA, indispensible amino acid; Iso or Ile, isoleucine; Leu, leucine; LNAA, large neutral amino acids; Met, methionine; MS/MS, tandem mass spectroscopy; PAH, phenylalanine hydroxylase; PE, protein equivalent; Phe, phenylalanine; PKU, phenylketonuria; Pro, proline; SEM, standard error of the mean; Ser, serine; Thr, threonine; Tyr, tyrosine; Trp, tryptophan; Val, valine; WT, wild type.

II. The Invention

The inventors have recently determined that medical foods made with glycomacropeptide protein supplemented with additional amounts of the amino acids arginine, histidine, leucine, and optionally, other amino acids, as the amino acid/protein source contained in the foods, provide a complete, low-Phe source of protein in the diet for individuals with PKU or other metabolic disorders. These foods are more palatable than standard AA formulas, and optimize the ability of GMP to lower levels of Phe in the blood and brain. Accordingly, the present invention provides medical foods, methods of making such foods, and methods of administering such foods as a protein source to individuals with metabolic disorders such as PKU.

In one aspect, the invention provides medical foods containing a complete low Phe protein source. The primary protein source in the medical foods of the present invention is Glycomacropeptide (GMP), a naturally occurring protein that contains no Phe in its pure form. GMP is formed during cheese making when chymosin specifically cleaves κ-casein between the 105 to 106 amino acid residues. Para-κ-casein (residues 1 to 105) coagulates, forming cheese curd, while GMP (residues 106 to 169) remains in the whey. GMP is highly polar and is glycosylated by galactosamine, galactose, and o-sialic acid at one or more threonine amino acid sites.

"GMP protein" refers to pure GMP polypeptide without the glycosylating moieties. GMP protein contains 47% (w/w) indispensable amino acids, but contains no histidine (His), tryptophan (Trp), tyrosine (Tyr), arginine (Arg), Cysteine (Cys) or Phe.

A number of methods can be used to isolate GMP from whey. Detailed examples of purification methods can be found, for example, in U.S. Pat. No. 5,968,586. Current large-scale technologies to isolate GMP from whey use ion exchange chromatography or ultrafiltration. GMP has an isoelectric point (pI) below 3.8, whereas other major whey proteins have pI values above 4.3. This physicochemical difference between GMP and other whey proteins is commonly used in isolation processes to separate GMP from whey.

Commercially available GMP contains Phe contaminants from residual whey proteins. The amount of Phe contamination in commercial GMP varies widely (i.e. 5 mg Phe/g product, manufacturer literature, Davisco Foods Intl., Eden Prairie, Minn., U.S.A.; 2.0 mg Phe/g product, Lacprodan cGMP-20 manufacturer literature, Arla Foods, Arhus, Denmark). Traditional amino acid formula is free of Phe, which allows an individual with PKU to consume natural foods that contain Phe to meet their daily allowance. Preferred GMP for use in the present invention contains no more than 2.0 mg Phe/g GMP.

In certain preferred embodiments, commercially obtained GMP may be purified to remove Phe contaminants before being used in the medical foods of the present invention. Possible purification processes are well known in the art, and include without limitation trapping contaminating whey proteins in crude GMP by adsorption onto a cation exchange resin and collecting the purified GMP in the flow-through fraction. Additional techniques known in the art, such as, for example, Ultrafiltration/diafiltration (UF/DF), can be used to concentrate the GMP and wash out peptides, salts, and non-protein nitrogen. After the purification and concentration steps, a number of techniques known in the art can be used to dry the purified, concentrated GMP, including without limitation lyophilization and spray drying.

Pure GMP contains no His, Tyr, Trp, Cys, Arg, or Phe, and is low in leucine (Leu). His, Trp, Phe, and Leu are all indispensable amino acids. Tyr, and Arg are conditionally indispensable amino acids, because Phe is a precursor to Tyr, and glutamate, proline and aspartate are precursors to Arg. As a result, GMP as a primary protein source in foods must be supplemented to provide a nutritionally complete protein. The inventors have determined optimal ranges for supplemental amounts of the amino acids arginine, leucine, and tyrosine that are different than what had been suggested previously in the art.

Accordingly, in certain preferred embodiments, the present invention includes medical foods for the management of a metabolic disorder where the medical foods contain glycomacropeptide (GMP) and additional optimized supplemental amounts of the amino acids arginine, leucine and/or tyrosine. Other amino acids may also be included in the medical foods of the invention. However, because the inventors have determined that methionine supplementation is not necessary, and in fact would make the medical foods less palatable, in certain preferred embodiments, the medical foods of the invention do not contain an additional supplemented amount of the amino acid methionine. Amino acids approved for use in food products can be obtained from a variety of commercial sources known in the art.

The preferred weight ratio within the medical food of each supplemented amino acids is expressed in the units of milligrams of that amino acid in the final medical food per gram of total protein, where a gram of total protein is defined as the sum of the protein from GMP (g nitrogen×6.25) and from the additional supplemented amino acids (g nitrogen×6.25). In certain preferred embodiments, the total weight of the additional supplemented amino acids is preferably from about 22% to 38% of the total weight of the protein from GMP and the supplemented amino acids added together.

Preferably, the weight ratio within the medical foods of the amino acid arginine to the protein is from about 60 to 90 milligrams arginine/gram total protein; more preferably, the weight ratio within the medical foods of the amino acid arginine to the total protein is about 75 milligrams arginine/gram total protein.

The preferred weight ratio within the medical foods of the amino acid leucine to the protein is from about 100 to 200 milligrams leucine/gram total protein; more preferably, the weight ratio within the medical foods of the amino acid leucine to the total protein is about 100 milligrams leucine/gram total protein.

In those embodiments containing supplemental amounts of tyrosine, the preferred weight ratio within the medical foods of the amino acid tyrosine to the total protein is from about 62 to 93 milligrams tyrosine/gram total protein; more preferably, the weight ratio within the medical foods of the amino acid tyrosine to the total protein is about 85 milligrams tyrosine/gram total protein.

In certain embodiments, the medical foods may optionally contain additional supplemented amino acids. For example, histidine and/or tryptophan may be included in the medical foods. For histidine supplementation, the preferred weight ratio within the medical foods of histidine to the total protein is from about 20 to 24 milligrams histidine/gram total protein; more preferably, the weight ratio within the medical foods of the amino acid histidine to the total protein is about 23 milligrams histidine/gram total protein.

For tryptophan supplementation, the preferred weight ratio within the medical foods of tryptophan to the total protein is from about 12 to 14 milligrams tryptophan/gram total protein; more preferably, the weight ratio within the medical foods of the amino acid tryptophan to the total protein is about 12 milligrams tryptophan/gram total protein.

In certain embodiments, the medical foods may be additionally supplemented with essential vitamins and minerals, providing required non-protein nutritional supplementation in addition to a complete protein source. Furthermore, the medical foods may contain a variety of other low-Phe substances that are typically contained in conventional foods (non-protein ingredients).

The invention is not limited to medical foods for the treatment of Phe metabolism disorders such as PKU; instead the medical foods of the invention additionally include foods for the management of a metabolism disorder of other amino acids that are not present in GMP (i.e. metabolism disorders of His, Trp, Tyr, or Phe). For embodiments used in the management of tyrosine metabolism disorders such tyrosinemia, the optimal supplemental amounts of arginine and leucine are included in the foods, but no supplemental amount of tyrosine is included. To adjust for the lost tyrosine, the amount of GMP can be increased. In some such embodiments, the total weight of the additional supplemented amino acids is preferably from about 16% to 29% of the total weight of the protein from GMP and the supplemented amino acids added together. Preferably, the amount of tyrosine plus phenylalanine together in such embodiments is less than 2.0 mg per gram total protein.

The medical foods of the present invention encompass a wide variety of food types, including without limitation a formula, a beverage, a bar, a wafer, a pudding, a gelatin, a cracker, a fruit leather, a nut butter, a sauce, a salad dressing, a flake, a crisp cereal piece, a puff, a pellet, or an extruded solid. These and other possible food types would be easily recognized by those skilled in the art, and conventional manufacturing methods could be used to make the medical foods of the invention using the ingredients of the invention along with other low-Phe substances typically used in conventional foods.

A number of the possible types of food encompassed by the invention are subject to heat treatment during production. As a non-limiting example, crackers, bars, and crisp cereal pieces may be baked. Extruded solids may be heated prior to extrusion. Fruit leathers, sauces, and crisp cereal pieces can be made by heating a mixture prior to cooling and, in some cases, drying the final product. Accordingly, in certain embodiments, the medical foods of the invention are heat-treated during production.

The inventors have determined that heat treatment may lead to a significant loss of the additional supplemented amino acids. For example, free amino acids such as Trp, Tyr, His, Leu, and Arg may undergo the Maillard reaction. Light exposure can accelerate the Tyr photodegradation reaction. Loss of the additional supplemented amino acids by heat treatment or light exposure would increase the amount of additional supplemented amino acids that must be added to the medical foods. Thus, in some preferred embodiments, the initial weight ratio of each supplemented amino acid would be set higher for foods that are heat treated than for foods that are not heat-treated such that after loss the final remaining amount of each supplemented amino acid falls within the preferred weight ratio.

In another aspect, the invention encompasses a method of making medical foods for the management of a metabolic disorders such as PKU. The method includes the steps of providing glycomacropeptide (GMP) and additional supplemented amounts of amino acids including arginine and leucine, and mixing the provided materials with other substances to make the foods. In certain embodiments of the method, the weight ratio of the amino acid arginine provided to the protein provided is from about 60 to 90 milligrams leucine/gram total protein, preferably about 75 milligrams arginine/gram total protein. In certain embodiments of the method, the weight ratio of the amino acid leucine provided to the total protein provided is from about 100 to 200 milligrams leucine/gram total protein, preferably about 100 milligrams leucine/gram total protein.

As described above, a variety of other substances can be used in making the foods, including non-protein ingredients typically used to make conventional foods. The other substances used, however, must be low-Phe or Phe-free substances.

In some embodiments, it is preferred that the total weight of the additional supplemented amino acids used in the method is from about 22% to 38% of the total weight of the protein from GMP and the supplemented amino acids together. The method encompasses conventional techniques used to make a variety of food types. As non-limiting examples, the food mixture may be allowed to set to form a pudding, gelatin, or fruit leather; the food mixture may be formed into a bar, a cracker, a flake, a puff, or a pellet; or the food may be extruded as an extruded solid. In some embodiments of the method, the food mixture is heat treated. Examples of heat treatment include without limitation baking the food mixture, pasteurizing the food mixture, boiling the heat mixture, or subjecting the mixture to heated extrusion.

In certain embodiments of the method, the weight ratio of the amino acid tyrosine provided to the protein provided is from about 62 to 93 milligrams tyrosine/gram total protein, preferably about 85 milligrams tyrosine/gram total protein.

In certain embodiments of the method, the weight ratio of the amino acid histidine provided to the protein provided is from about 20 to 24 milligrams histidine/gram total protein, preferably about 23 milligrams histidine/gram total protein.

In certain embodiments of the method, the weight ratio within the food of the amino acid tryptophan to the protein is from about 12 to 14 milligrams tryptophan/gram total protein, preferably about 12 milligrams tryptophan/gram total protein.

The method may also include the step of purifying the GMP so that it contains not more than 2.0 mg phenylalanine contaminant per gram GMP protein. A number of techniques known in the art can be used to purify the GNP, including without limitation the use of cation exchange chromatography, ultrafiltration and diafiltration. The purified GNP may further be dried using any one of a number of known drying techniques, including without limitation lyophilization or spray drying.

In yet another aspect, the invention encompasses a method of treating a metabolic disorder. This method includes the steps of selecting a patient with a metabolic disorder and administering to the patient a medical food comprising glycomacropeptide (GMP) and additional optimal supplemented amounts of the amino acids arginine and leucine. Preferably, the weight ratio within the medical food of the amino acid arginine to the total protein is from about 60 to 90 milligrams arginine/gram total protein, more preferably about 75 milligrams arginine/gram total protein. Preferably, the weight ratio within the food of the amino acid leucine to the total protein is from about 100 to 200 milligrams leucine/gram total protein, more preferably about 100 milligrams leucine/gram total protein.

The metabolic disorder is preferably one of a Phe metabolism disorder, a His metabolism disorder, a Trp metabolism disorder, a Tyr metabolism disorder, or a Phe metabolism disorder. In some embodiments, the total weight of the additional supplemented amino acids in the administered medical food is from about 22% to 38% of the total weight of the GMP protein and supplemented amino acids together.

In certain embodiments of the method, the medical food is not supplemented with tyrosine, and the selected patient has a tyrosine metabolism disorder. In such embodiments, the medical food preferable contains less than 2.0 milligrams phenylalanine plus tyrosine per gram total protein. In some such embodiments, the total weight of the additional supplemented amino acids in the administered medical food is from about 16% to 29% of the total weight of the GMP protein and supplemented amino acids together.

In certain embodiments of the method, the medical foods used in the method further contain additional optimal supplemented amounts of the amino acid tyrosine. Preferably, the weight ratio within the medical food of the amino acid tyrosine to the total protein is from about 62 to 93 milligrams tyrosine/gram total protein, more preferably about 85 milligrams tyrosine/gram total protein. If optimal amounts of arginine, leucine and tyrosine are included, the selected patient may have a phenylalanine metabolism disorder, a histidine metabolism disorder, or a tryptophan metabolism disorder. If the patient has a histidine metabolism disorder, the medical food administered does not contain a supplemented amount of histidine. If the patient has a tryptophan metabolism disorder, the medical food administered does not contain a supplemented amount of tryptophan.

Subject to the limitations noted above, other amino acids may optionally be included in the medical foods used in the method. In certain embodiments of the method, the weight ratio within the medical food of the amino acid histidine to the total protein is from about 20 to 24 milligrams histidine/gram total protein, preferably about 23 milligrams histidine/gram total protein.

In certain embodiments of the method, the weight ratio within the food of the amino acid tryptophan to the total protein is from about 12 to 14 milligrams tryptophan/gram total protein, preferably about 12 milligrams tryptophan/gram total protein.

In certain preferred embodiments, the patient selected has the metabolic disorder PKU. The medical foods of the invention are more palatable than conventional amino acid formulas, help decrease harmful Phe levels in the plasma and brain, and help improve protein retention in such patients. In some embodiments, the food is administered to a human that is at least two years old.

Although in certain preferred embodiments, the patient selected has the metabolic disorder PKU, the method encompasses the administration of the medical foods to patients having other metabolic disorders. Other metabolic disorders that could be effectively treated by administering the foods of the present invention include: Tyrosine metabolism disorders (Type I tyrosinemia, Type II tyrosinemia, Type III tyrosinemia/Hawkinsinuria, and Alkaptonuria/Ochronosis); Tyrptophan metabolism disorders (Hypertryptophanemia); and Histidine metabolism disorders (Carnosinemia, Histidinemia, and Urocanic aciduria).

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Supplemented Glycomacropeptide Diet in Murine Model of PKU

In this example, Applicants demonstrate that in a standard mouse model of PKU, a supplemented glycomacropeptide diet supports growth and reduces phenylanine concentrations in both plasma and brain, as compared an amino acid diet. The murine model of PAH deficiency, the Pah$^{enu2}$ mouse (PKU mouse) is a suitable model to study the nutritional management of PKU as it exhibits hyperphenylalaninemia and cognitive defects similar to humans with PKU. Moreover, parallel to the human low-Phe diet in which the majority of dietary protein is provided by amino acids, studies in the PKU mouse utilize an amino acid-based diet often free of Phe with provision of Phe in drinking water. Our objective was to assess how ingestion of diets containing GMP as the sole protein source support growth and impact the concentrations of amino acids, in particular Phe, in plasma and brain of wild-type (WT) and PKU mice. The results demonstrated suitable growth and significantly reduced concentrations of Phe in plasma and the brain of PKU mice fed GMP compared with an amino acid diet.

Materials and Methods.

Mice.

The animal facilities and protocols reported were approved by the University of Wisconsin-Madison Institutional Animal Care and Use Committee. Male and female 4- to 6-wk-old WT mice weighing 18-22 g were bred on the same background as the PKU mice (C57B1/6, Jackson Laboratories). PKU mice were homozygous for the Pah mutation but were bred and backcrossed onto the C57B1/6 background to increase breeding facility. Breeding pairs of PKU mice were provided by Cary O. Harding, Oregon Health and Science University, Portland, Oreg. Genotyping for the presence of the $Pah^{enu2}$ mutation was performed by PCR analysis of tail biopsy DNA on an amplified region of exon 7. Mice were individually housed in stainless steel, wire-bottom cages in a room maintained at 22° C. on a 12-:12-h light:dark cycle and were given free access to water. The mice were weighed every day at 1000 and food intake was determined daily. At the conclusion of each experiment, mice were anesthetized using isoflurane via an anesthesia machine (IsoFlo, Abbott Laboratories) and killed by cardiac puncture/exsanguination between 0800 and 1000 with removal of food 1 h before being killed.

Diets.

Purified diets were designed to provide similar amounts of vitamins, minerals, energy, and macronutrients (See Table 1). The protein source in the diets was provided by casein, free amino acids, GMP (BioPURE GMP, Davisco Foods), and GMP processed to reduce residual Phe content (see Etzel M. R., J Nutr. 2004; 134:S996-1002). The GMP diets were supplemented with 1.5 times the NRC suggested requirement (see NRC, Nutrient Requirements of the Mouse, in Nutrient Requirements of Laboratory Animals, 4th ed. Washington D.C.: National Academy Press; 1995) for the following limiting IAA to compensate for faster absorption and degradation of amino acids compared with intact protein: arginine, histidine, leucine, methionine, tryptophan, and tyrosine. The nitrogen content of the amino acid and GMP low-Phe diets was similar, 24.1 and 22.9 g nitrogen/kg diet, respectively, and both diets provided 175 g amino acids/kg of diet. Complete amino acid analysis of the diets was conducted in the Experiment Station Chemical Laboratories, University of Missouri-Columbia (Columbia, Mo.) (See Table 2).

TABLE 1

| Ingredient | Experimental diets | | | | |
|---|---|---|---|---|---|
| | Casein | GMP adequate | GMP, Phe deficient | GMP, low Phe | Amino acid, low Phe |
| | | | g/kg | | |
| Protein | | | | | |
| Casein | 200.0 | | | | |
| BioPure GMP[1] | | 200.0 | | 200.0 | |
| Wisconsin GMP[2] | | | 200.0 | | |
| L-Arginine HCl | | 4.6 | 4.6 | 4.6 | 12.1[3] |
| L-Cystine | 3.0 | | | | 3.5 |
| L-Histidine, HCl—H$_2$0 | | 3.2 | 3.2 | 3.2 | 4.5 |
| L-Leucine | | 6.8 | 7.0 | 6.8 | 11.1 |
| L-Methionine | | 7.0 | 7.0 | 7.0 | 8.2 |
| L-Phenylalanine | | 10.4 | | 0.15 | 0-2.5 |
| L-Tyrosine | | 5.0 | 5.0 | 5.0 | 5.0 |
| L-Tryptophan | | 1.3 | 1.5 | 1.3 | 1.8 |
| Carbohydrate | | | | | |
| Sucrose | 180.0 | 180.0 | 180.0 | 180.0 | 359.0 |
| Cornstarch | 302.0 | 279.0 | 287.0 | 288.0 | 150.0 |
| Maltodextrin | 130.0 | 130.0 | 130.0 | 130.0 | 150.0 |
| Cellulose | 50.0 | 50.0 | 50.0 | 50.0 | 30.0 |
| Fat | | | | | |
| Soybean oil | 70.0 | 70.0 | 70.0 | 70.0 | 80.0 |
| Choline bitartrate | 2.5 | 2.5 | 2.5 | 2.5 | 2.5 |
| Vitamins and minerals | | | | | |
| Vitamin mix AIN-93-VX[4] | 10.0 | 10.0 | 10.0 | 10.0 | 13.0 |
| Mineral mix AIN-93G-MX[4] | 35.0 | 35.0 | 35.0 | 35.0 | 35.0 |
| Sodium chloride | 8.0 | | | | |
| Sodium phosphate dibasic | 5.0 | | | | |
| Calcium phosphate monobasic | | 5.0 | 5.0 | 5.0 | 8.0 |
| Calcium carbonate | 3.8 | | 1.6 | | |
| Magnesium oxide | 0.3 | | 0.3 | | |
| Antioxidant | | | | | |
| t-Butylhydroquinone | 0.01 | 0.01 | 0.01 | 0.01 | 0.02 |

[1]BioPURE GMP; Davisco Foods International, Inc., LeSueur, MN.
[2]Commercial GMP processed to reduce Phe content.
[3]In addition, the following L-amino acids were included for a total of 175 g amino acids/kg diet: alanine, 3.5; asparagine, 6.0; aspartic acid, 3.5; glutamic acid, 40; glycine, 23.3; isoleucine, 8.2; lysine HCl, 18.0; proline, 3.5; serine, 3.5; threonine, 8.2; and valine, 8.
[4]As reported by Reeves et al, AIN-93 purified diets for laboratory rodents: final report of the American Institute of Nutrition ad hoc writing committee on the reformulation of the AIN-76A rodent diet. J Nutr. 1993; 123: 1939-51.

TABLE 2

Amino acid profile of diets

| Amino acid | Casein | GMP adequate | GMP, Phe deficient | GMP, low Phe | Amino acid, low Phe |
|---|---|---|---|---|---|
| | | | g amino acid/kg | | |
| Alanine | 5.4 | 8.4 | 8.4 | 8.8 | 3.5 |
| Arginine | 6.8 | 1.2 | 3.8 | 3.7 | 8.4 |
| Aspartic acid | 12.6 | 13.0 | 12.9 | 14.3 | 9.7 |
| Cysteine | 3.4 | 0.2 | 0.2 | 0.2 | 3.5 |
| Glutamic | 41.2 | 32.3 | 31.9 | 33.5 | 40.0 |
| Glycine | 3.4 | 1.8 | 1.7 | 2.1 | 23.3 |
| Histidine | 5.7 | 2.6 | 2.9 | 2.9 | 2.6 |
| Isoleucine | 9.3 | 16.0 | 15.5 | 15.1 | 9.0 |
| Leucine | 17.2 | 10.0 | 10.7 | 12.0 | 13.9 |
| Lysine | 15.1 | 8.8 | 8.7 | 8.1 | 17.0 |
| Methionine | 4.8 | 8.3 | 7.9 | 8.3 | 8.2 |
| Phenylalanin | 9.4 | 10.1 | 0.4 | 2.2 | 2.4 |
| Proline | 19.3 | 18.3 | 18.1 | 18.5 | 5.3 |
| Serine | 8.0 | 8.9 | 9.2 | 10.4 | 2.8 |
| Threonine | 7.2 | 32.9 | 23.5 | 27.5 | 8.2 |
| Tryptophan | 2.3 | 1.4 | 1.5 | 1.5 | 1.8 |
| Tyrosine | 8.6 | 4.2 | 4.0 | 4.9 | 4.1 |
| Valine | 12.0 | 12.5 | 12.3 | 14.1 | 9.4 |

Experimental Design.

Three experiments were conducted. Expt. 1 tested the adequacy of GMP supplemented with IAA to support food intake and growth in 4-wk-old, male WT mice fed for 42 d. Three dietary treatment groups (n=10/group) were included: casein control, GMP supplemented with all limiting IAA (GMP adequate), and, to establish that Phe was limiting, GMP processed to reduce residual Phe and supplemented with all limiting IAA except Phe (GMP Phe deficient). When food intake failed after 3 d of feeding the GMP Phe-deficient diet, we added Phe to the drinking water (1 g Phe/L) on d 4.

Expt. 2 tested the ability of diets containing amino acids and GMP to support growth in male and female PKU mice (5-8 wk old) when Phe was provided in the drinking water (1 g Phe/L) for 21 d. Three dietary treatment groups were included (n=10/group): PKU mice fed the GMP Phe-deficient diet, PKU mice fed an amino acid Phe-deficient diet, and WT mice fed the GMP-adequate diet. We measured drinking water intake daily in PKU mice and adjusted for evaporation to determine the amount of Phe consumed.

Expt. 3 evaluated the ability of diets containing amino acids and GMP that were supplemented with a minimum amount of Phe (determined from Expt. 2) to support growth and affect the concentrations of amino acids in plasma and the brain of male and female PKU mice fed for 47 d. Four dietary treatment groups were included: 6-wk-old WT mice fed casein (n=8) or the GMP-adequate diet (n=7) and 8- to 10-wk-old PKU mice fed the amino acid, low-Phe (n=10) or the GMP, low-Phe diet (n=11). There were similar numbers of male and female mice in each treatment group. Blood samples were obtained by orbital bleeding for amino acid analysis using heparinized capillary tubes after 21 d of feeding (n=5/group). Mice were anesthetized, killed by cardiac exsanguination, and decapitated after 47 d. The brains were quickly removed and placed on a glass plate cooled by dry ice. Using visual landmarks, samples were taken from the following 5 regions; cerebellum, brain stem, hypothalamus, parietal cortex, and the anterior piriform cortex. The samples were placed in preweighed polystyrene tubes, weighed to determine sample mass, and stored at −80° C. until processing.

Amino Acid Analysis.

Blood was collected by cardiac puncture into syringes containing a final concentration of 2.7 mmol/L EDTA and plasma was isolated by centrifugation at 1700×g; 15 min at 4° C. The profile of free amino acids in plasma was determined using a Beckmann 6300 amino acid analyzer equipped with an ion chromatography system using post column ninhydrin derivatization. The samples were deproteinized with sulfosalicylic acid, centrifuged (14,000×g; 5 min, and passed through a 0.2-µm syringe filter before adding an internal standard and injecting into the column.

The profile of free amino acids in the brain was determined in the Amino Acid Analysis Laboratory, University of California-Davis, School of Veterinary Medicine (Davis, Calif.) using a Biochrom 30 amino acid analyzer (Biochrom). The procedure for extraction of amino acids from the brain samples included the addition of 3% sulfosalicylic acid containing 100 µmol/L Norleucine as an internal standard (Sigma Chemicals) in a ratio of 1:10 (wt:v), homogenization with an ultrasonic needle for 2 min, centrifugation at 14,000×g; 20 min at 4° C., and filtration of supernatant through a 0.45-µm syringe drive filter. The filtrate was adjusted to pH 2.2 with 0.4 mol/L LiOH and 0.05 mL was injected into the column. Values are expressed as nmol amino acid/g wet tissue weight.

Statistics.

Statistical analyses were conducted using SAS version 8.2 (SAS Institute) and R (Universitat Wien, Vienna, Austria). Data were analyzed using general linear models. The differences between dietary treatment groups were determined by the protected least significant difference technique. Statistics were performed on log-transformed data when residual plots indicated unequal variance among groups as occurred for some of the data. Where appropriate, sex was included as a covariate to adjust for its potential influence. Changes in body weight (BW) among treatment groups were assessed with repeated measures analysis in Expt. 1. Among PKU mice, simple linear regression was used to examine the correlations between dietary intakes of amino acids 48 h prior to death and the concentrations of amino acids in plasma and brain. All values are presented as means±SE; $P \leq 0.05$ was considered significant.

Results

Expt. 1.

Initial and final BW did not differ among the 3 dietary treatment groups (See FIG. 1). Food intake and BW did not differ when comparing the casein and GMP adequate groups throughout the 42-d study. Mice stopped eating the GMP Phe-deficient diet after 3 d, at which time Phe was added to the drinking water and food intake resumed. The 3 dietary groups did not differ in changes in daily BW from d 14 to d 42.

The profile of amino acids in plasma was significantly altered with intake of GMP compared with casein. WT mice fed the GMP-adequate or Phe-deficient diets showed elevated plasma concentrations of the IAA, threonine, isoleucine, and methionine, which were 3-fold, 2.4-fold, and 1.6-fold, respectively, of the concentrations in mice fed the casein diet (data not shown). Mice fed the GMP Phe-deficient diet showed significantly lower plasma concentrations of Phe and tyrosine compared with the GMP-adequate and casein groups.

Expt. 2.

Initial (16-18±1.4 g) and final (19-21±1.3 g) BW and food intake (3.3 to 4.1±0.3 g/d) did not significantly differ among the 3 treatment groups for 21 d. Mean Phe intake in PKU mice was 6.5±0.5 mg Phe/d with ingestion of the amino acid Phe-deficient diet and 5.9±0.3 mg Phe/d with ingestion of the GMP Phe-deficient diet (P>0.10). Considering our observations from Expt. 1 and 2 that growth may be limited with provision of Phe in the drinking water, we decided to supplement the low-Phe amino acid and GMP diets for Expt. 3 to contain 2.5 g Phe/kg diet. This provided a daily Phe intake for growing PKU mice of 7.5-10 mg Phe.

Expt. 3.

Gain in BW, feed utilization based on the ratio of feed intake to gain in BW, and the protein efficiency ratio did not differ among the 4 dietary treatment groups (see Table 3). PKU mice were ~2 g heavier than WT mice (P<0.05), consistent with the former being 2 wk older. Female mice of both genotypes weighed less than male mice at the end of the study (20±1 g vs. 25±1 g; n=17-18; P<0.0001).

TABLE 3

BW, feed utilization, and organ mass of WT and PKU mice fed diets containing casein, GMP, or amino acids (Expt. 3)[1]

|  | WT mice | | PKU mice | |
| --- | --- | --- | --- | --- |
|  | Casein | GMP adequate | Amino acid, low Phe | GMP, low Phe |
| n | 8 | 7 | 10 | 11 |
| BW | | | | |
| Initial, g | 16.9 ± 0.8[bc] | 16.3 ± 1.2[c] | 19.3 ± 1.0[a] | 18.6 ± 0.9[ab] |
| Final, g | 21.2 ± 1.1[b] | 21.2 ± 0.9[b] | 23.8 ± 1.3[a] | 23.3 ± 0.8[a] |
| Gain, g/47 d | 4.3 ± 0.6 | 5.0 ± 0.7 | 4.5 ± 0.8 | 4.7 ± 0.7 |
| Feed utilization | | | | |
| Feed intake, g | 147 ± 5[b] | 145 ± 4[b] | 169 ± 8[a] | 166 ± 4[a] |
| Feed:gain ratio | 39 ± 6 | 32 ± 3 | 45 ± 6 | 40 ± 6 |
| Protein efficiency ratio[2] | 0.17 ± 0.02 | 0.20 ± 0.08 | 0.15 ± 0.02 | 0.16 ± 0.03 |
| Relative organ mass, g/100 g BW | | | | |
| Kidney | 1.38 ± 0.04[b] | 1.28 ± 0.02[bc] | 1.48 ± 0.05[a] | 1.26 ± 0.02[c] |
| Heart | 0.51 ± 0.01[b] | 0.60 ± 0.04[a] | 0.52 ± 0.01[b] | 0.52 ± 0.01[b] |
| Liver | 4.61 ± 0.20[b] | 4.77 ± 0.13[b] | 5.22 ± 0.09[a] | 5.31 ± 0.11[a] |

[1]Values are means ± SE. Means in a row with superscripts without a common letter differ, P < 0.05.
[2]Protein efficiency ratio, g gain in BW/g protein intake.

Relative organ mass showed significant differences due to diet and sex. Kidney mass was significantly greater in PKU mice fed the amino acid diet compared with the other groups. Heart mass was significantly greater in WT mice fed the GMP-adequate diet compared with the other groups. PKU mice fed either the amino acid or GMP diet showed significantly greater relative mass of liver compared with WT mice. Female mice of both genotypes showed significantly lower relative kidney mass and significantly greater relative heart mass compared with male mice.

The profile of amino acids in plasma was affected by diet and sex (see Table 4).

TABLE 4

Concentrations of amino acids in plasma of WT and PKU mice fed diets containing casein, GMP, or amino acids (Expt. 3)[1]

|  | WT mice | | PKU mice | |
| --- | --- | --- | --- | --- |
| Amino acid | Casein | GMP adequate acid | Amino Acid low Phe | GMP low Phe |
|  | | | μmol/L | |
| Alanine | 793 ± 97 | 570 ± 108 | 698 ± 63 | 580 ± 75 |
| Arginine | 86 ± 7[a] | 61 ± 5[b] | 81 ± 7[a] | 62 ± 5[b] |
| Aspartate | 30 ± 2 | 25 ± 3 | 23 ± 2 | 24 ± 2 |
| Citrulline | 46 ± 4 | 41 ± 3 | 57 ± 6 | 53 ± 6 |
| Cystine | 8 ± 2 | 8 ± 2 | 11 ± 3 | 8 ± 3 |
| Glutamate | 47 ± 4 | 44 ± 4 | 36 ± 4 | 41 ± 3 |
| Glutamine | 565 ± 41[ab] | 613 ± 35[a] | 430 ± 17[c] | 505 ± 25[bc] |
| Glycine | 248 ± 15[b] | 227 ± 21[b] | 654 ± 43[a] | 182 9[b] |
| Histidine | 91 ± 8[a] | 65 ± 4[b] | 71 ± 4[b] | 62 ± 4[b] |
| Isoleucine | 95 ± 8[b] | 155 ± 31[a] | 78 ± 5[b] | 155 ± 15[a] |
| Leucine | 190 ± 11[a] | 123 ± 13[b] | 108 ± B[b] | 130 ± 8[b] |
| Lysine | 501 ± 49[a] | 277 ± 12[c] | 397 ± 37[b] | 269 ± 16[c] |
| Methionine | 96 ± 9 | 85 ± 13 | 80 ± 9 | 70 ± 9 |
| Ornithine | 63 ± 6[a] | 35 ± 2[c] | 47 ± 4[b] | 40 ± 3[bc] |
| Phenylalanine | 59 ± 3[c] | 45 ± 3[c] | 851 ± 29[a] | 756 ± 21[b] |
| Proline | 209 ± 35[a] | 228 ± 83[a] | 74 ± 6[b] | 97 ± 11[b] |
| Serine | 248 ± 24[ab] | 207 ± 23[bc] | 265 ± 14[a] | 173 ± 10[c] |
| Taurine | 643 ± 22 | 600 ± 67 | 624 ± 63 | 532 ± 45 |
| Threonine | 303 ± 32[b] | 562 ± 76[8] | 331 ± 19[b] | 557 ± 65[a] |
| Tryptophan | 110 ± 7[a] | 106 ± 16[ab] | 87 ± 10[c] | 93 ± 5[bc] |

TABLE 4-continued

Concentrations of amino acids in plasma of WT and PKU mice fed diets containing casein, GMP, or amino acids (Expt. 3)[1]

|  | WT mice | | PKU mice | |
| --- | --- | --- | --- | --- |
| Amino acid | Casein | GMP adequate acid | Amino Acid low Phe | GMP low Phe |
|  | | | μmol/L | |
| Tyrosine | 121 ± 12[a] | 82 ± 7[b] | 31 ± 3[c] | 25 ± 2[c] |
| Valine | 293 ± 31[a] | 228 ± 30[1] | 184 ± 16[c] | 262 ± 22[ab] |
| BCAA[2] | 609 ± 49[a] | 505 ± 66[a] | 370 ± 16[b] | 548 ± 41[a] |

[1]Values are means ± SE, n = 8. Means in a row with superscripts without a common letter differ, P < 0.05.
[2]BCAA, Sum of isoleucine, leucine, and valine.

PKU mice fed either the amino acid or GMP low-Phe diet showed 15-fold greater plasma concentrations of Phe and a 60-70% decrease in plasma concentrations of tyrosine and proline compared with WT mice fed either the casein or GMP diets. Both WT and PKU mice fed GMP diets showed plasma concentrations of threonine and isoleucine that were ~2 times the values in WT and PKU mice fed the casein or amino acid diets (P<0.002). Decreased plasma concentrations of lysine were noted in WT and PKU mice fed GMP diets (272±11 μmol/L) compared with WT and PKU mice fed the casein or amino acid diets (443±31 μmol/L; P<0.0001; n=17-18). Female mice of both genotypes showed greater plasma concentrations of tyrosine (74±6 vs. 53±8 μmol/L) and tryptophan (113±5 vs. 81±5 μmol/L) compared with male mice (P<0.01; n=17-18).

PKU mice fed GMP compared with the amino acid diet had significant differences in the concentrations of amino acids in plasma. PKU mice had a significant 11% decrease in the concentration of Phe in plasma with ingestion of GMP compared with the amino acid diet for 47 d; this effect was not observed at 21 d. Phe intake for the last 48 h before mice were killed was similar for PKU mice (16-18 mg Phe/48 h) but was significantly lower compared with WT mice (58-66 mg Phe/48 h). The sum of plasma concentrations of the branched chain amino acids, isoleucine, leucine and valine, increased by 50% in PKU mice fed GMP compared with the amino acid diet; however, the concentration of leucine did not differ. Among the PKU mice, dietary amino acid intake for the last 48 h before mice were killed and the concentrations of amino acids in plasma were correlated. The highest positive correlations ($P<0.0001$; n=15) include the following: glycine, $R^2=0.88$; threonine, $R^2=0.45$; isoleucine, $R^2=0.44$; and valine, $R^2=0.34$.

The profile of amino acids in the cerebellum differed significantly due to diet but not sex (see Table 5). The concentration of Phe in cerebellum of PKU mice was 3 to 4 times the value in WT mice ($P<0.0001$). The concentrations of tyrosine and the sum of the branched chain amino acids in cerebellum of PKU mice were ~50% of that in WT mice regardless of diet ($P<0.0001$). PKU mice fed the GMP diet had a 20% decrease in the concentration of Phe in cerebellum compared with PKU mice fed the amino acid diet.

Figure 2:
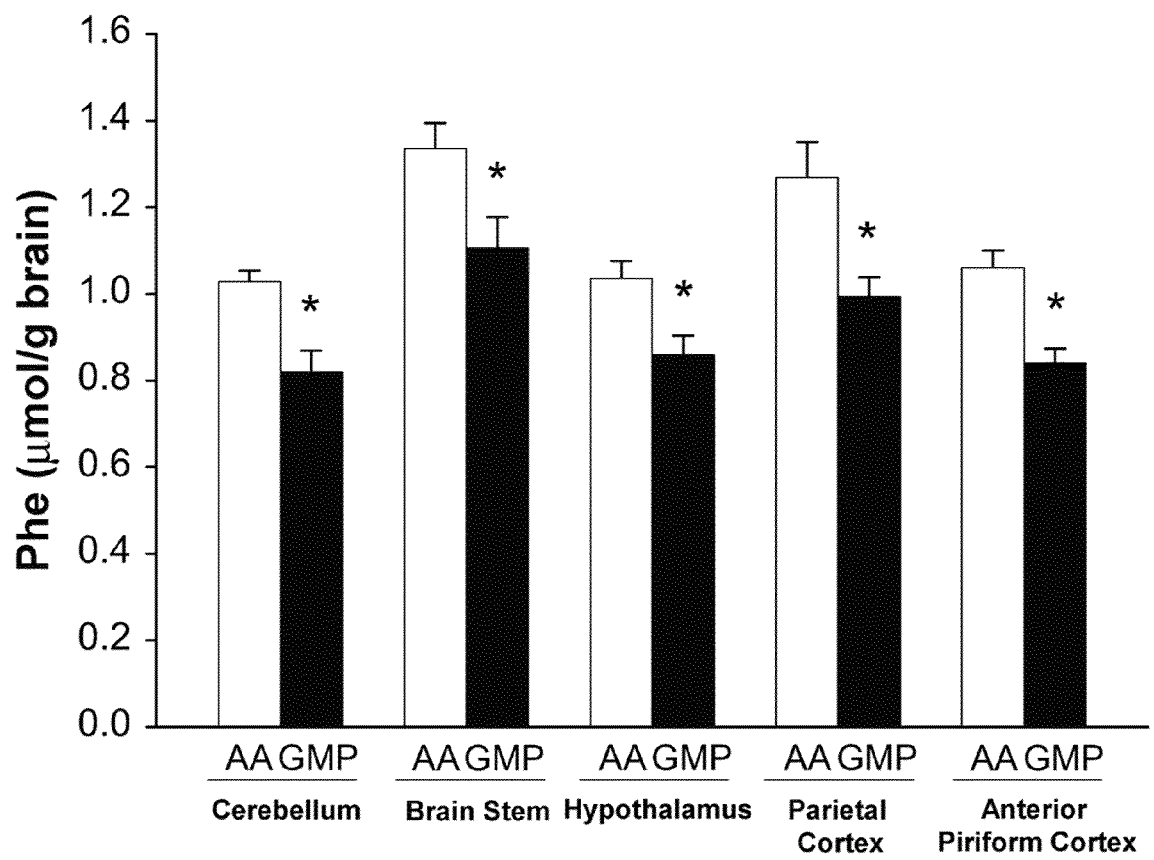
FIG. 2 shows the concentration of Phe in 5 sections of brain, cerebellum, brain stem, hypothalamus, parietal cortex, and anterior piriform cortex, of PKU mice fed the GMP or amino acid (AA) diet for 47 d. Values are means±SEM; n=8. *Different from AA, P≤0.001.
Figure 3:
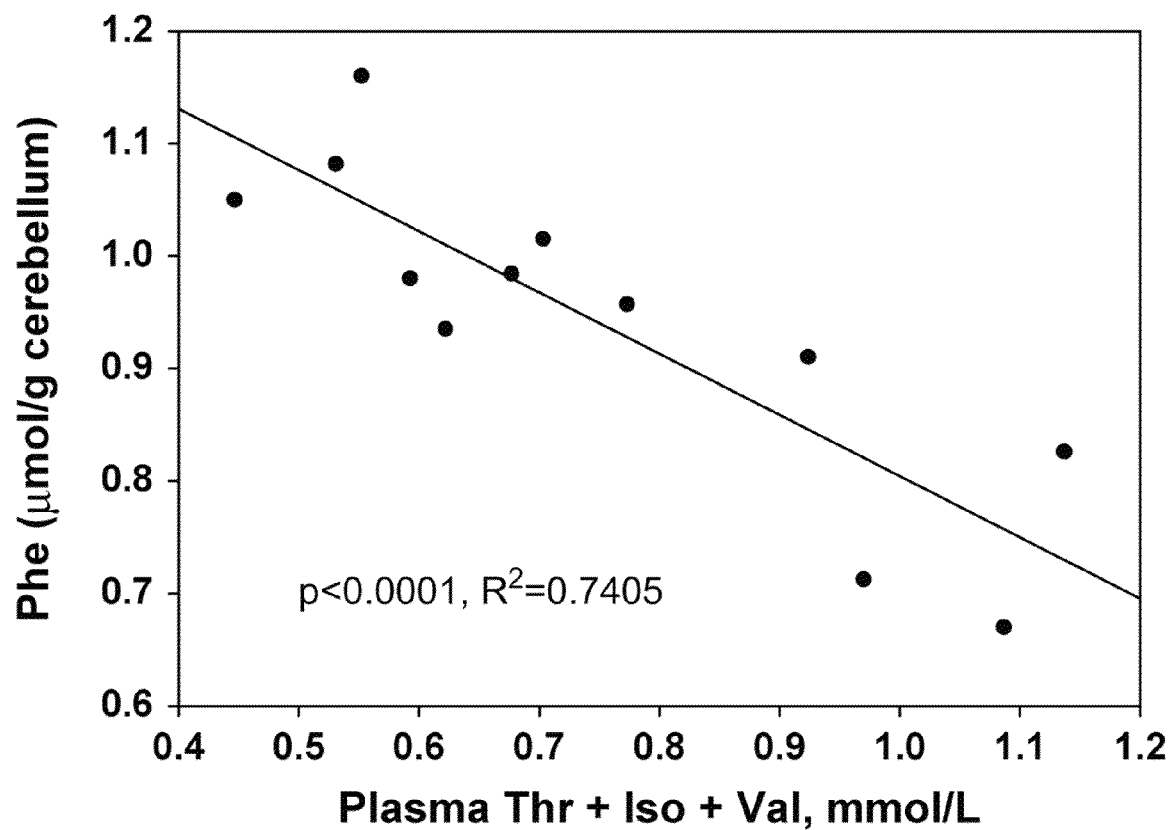
FIG. 3 shows cerebellum Phe levels for PKU mice fed the GMP or amino acid (AA) diet for 47 d as a function of plasma threonine (Thr)+isoleucine (Iso)+valine (Val) levels.

Moreover, this response of a 20% decrease in Phe concentration was noted in each of 5 sections of brain sampled: cerebellum, brain stem, hypothalamus, parietal cortex, and anterior piriform cortex (FIG. 2). The concentrations of threonine and isoleucine in the cerebellum increased 70-100% in PKU mice fed the GMP diet compared with the amino acid diet ($P<0.0001$). A similar trend was noted for higher valine concentration in the cerebellum of PKU mice fed the GMP diet compared with the amino acid diet ($P<0.10$). The concentration of Phe in the cerebellum of PKU mice was inversely correlated with the concentrations of threonine, isoleucine, and valine in plasma as well as the sum of the concentrations of threonine, isoleucine, and valine in plasma, $R^2=0.65-0.77$ ($P<0.0001$) (FIG. 3). The concentration of glutamine in cerebellum was 11% lower in PKU mice compared with WT mice regardless of diet ($P<0.05$). The concentrations in the cerebellum of tryptophan, the precursor of the neurotransmitter serotonin, and glycine, a precursor of the glycinergic neurotransmitter system of the brain, did not differ among groups.

Discussion

This study assesses the ability of diets containing GMP supplemented with IAA as the sole protein source to support growth and affect the concentrations of amino acids in the plasma and brains of PKU mice. In support of utilization of GMP as a source of low-Phe protein in the PKU diet, we observed similar growth with significantly lower concentrations of Phe in the plasma and brains of PKU mice fed GMP compared with an amino acid diet.

When fed as the sole source of dietary protein, GMP contains limiting amounts of several IAA for growing mice including: arginine, histidine, leucine, methionine, Phe, tryptophan, and tyrosine. Our results showed adequate growth of mice that are fed GMP supplemented with these limiting IAA. In Expt. 1, weanling WT mice fed casein or the GMP-adequate diet had virtually identical growth over 6 wk. In Expt. 3, PKU mice fed GMP or amino acid diets with similar Phe intake showed gains in BW, feed efficiency and a protein efficiency ratio that were not significantly different. These data demonstrate that GMP supplemented with limiting IAA provides a nutritionally adequate source of dietary protein for growing mice.

Consumption of a diet that is deficient in an IAA rapidly depresses the concentration of the limiting IAA in plasma and brain with reduced food intake in rats (Harper, et al., Physiol Rev. 1970; 50:428-39). Thus, it was not surprising that in Expt. 1, mice stopped eating the GMP Phe-deficient diet and lost BW after only 3 d of this diet and that addition of Phe to the drinking water normalized food intake and gain in BW. The plasma concentrations of isoleucine and threonine in WT mice fed the GMP-adequate diet were 2 to 3 times those in WT mice fed the casein diet. However, these alterations in plasma amino acid concentrations did not impair food intake in mice fed GMP once the deficiency of Phe was corrected.

TABLE 5

Concentrations of amino acids in cerebellum of WT and PKU mice fed diets containing casein, GMP, or amino acids (Expt. 3)[1]

| Amino acid | WT mice | | PKU mice | |
| --- | --- | --- | --- | --- |
| | Casein | GMP adequate | Amino acid low Phe | GMP low Phe |
| | | | nmol/g | |
| Alanine | 2380 ± 193 | 2145 ± 134 | 2082 ± 27 | 2303 ± 83 |
| Arginine | 55 ± 8 | 50 ± 6 | 35 ± 3 | 40 ± 5 |
| Aspartate | 9060 ± 306 | 9122 ± 256 | 8406 ± 191 | 8836 ± 630 |
| Citrulline | 373 ± 39 | 320 ± 42 | 293 ± 29 | 277 ± 25 |
| Half-Cystine | 110 ± 22 | 99 ± 15 | 93 ± 21 | 149 ± 39 |
| Glutamate | 12,870 ± 837 | 13,264 ± 712 | 12,886 ± 367 | 13,254 ± 505 |
| Glutamine | 11,459 ± 88$^a$ | 11,209 ± 197$^a$ | 10,049 ± 359$^b$ | 10,099 ± 250$^b$ |
| Glycine | 3923 ± 316 | 3764 ± 228 | 4383 ± 334 | 3753 ± 291 |
| Histidine | 216 ± 17 | 186 ± 12 | 236 ± 9 | 200 ± 8 |
| Isoleucine | 197 ± 19$^a$ | 192 ± 24$^a$ | 61 ± 21$^c$ | 123 ± 21$^b$ |
| Leucine | 462 ± 66$^a$ | 366 ± 43$^a$ | 164 ± 30$^b$ | 185 ± 30$^b$ |
| Lysine | 683 ± 35$^a$ | 581 ± 38$^b$ | 678 ± 31$^a$ | 615 ± 10$^{ab}$ |
| Methionine | 309 ± 18 | 286 ± 24 | 214 ± 14 | 163 ± 24 |
| Ornithine | 5 ± 1 | 5 ± 2 | 3 ± 2 | 7 ± 4 |
| Phenylalanine | 271 ± 34$^c$ | 232 ± 22$^c$ | 1030 ± 25$^a$ | 820 ± 49$^b$ |
| Proline | 312 ± 29 | 255 ± 35 | 187 ± 15 | 218 ± 24 |
| Serine | 1856 ± 91$^b$ | 1780 ± 87$^{bc}$ | 2156 ± 44$^a$ | 1609 ± 78$^c$ |
| Taurine | 10,886 ± 58 | 11,109 ± 292 | 10,896 ± 108 | 10,603 ± 96 |
| Threonine | 1300 ± 49$^c$ | 2590 ± 87$^a$ | 1589 ± 46$^b$ | 2695 ± 82$^a$ |
| Tryptophan | 90 ± 26 | 86 ± 12 | 59 ± 2 | 73 ± 3 |
| Tyrosine | 341 ± 27$^a$ | 278 ± 25$^b$ | 128 ± 14$^c$ | 128 ± 12$^c$ |
| Valine | 337 ± 40$^a$ | 304 ± 27$^{ab}$ | 187 ± 11$^c$ | 246 ± 20$^{bc}$ |
| BCAA2 | 966 ± 127$^a$ | 862 ± 92$^a$ | 413 ± 55$^b$ | 553 ± 39$^b$ |

[1]Values are means ± SE, n = 8. For PKU mice, the sample size was 3 for the following amino acids: alanine, aspartate, citrulline, glutamine, proline, taurine, and tryptophan. Means in a row with superscripts without a common letter differ, P < 0.05.
2BCAA, Sum of isoleucine, leucine, and valine.

Thus, we conclude that ingestion of GMP supplemented with all limiting IAA alters the plasma amino acid profile without reducing food intake in growing mice.

In contrast to other IAA, hepatic uptake of threonine is low and oxidation of threonine to $CO_2$ via liver threonine dehydratase activity (EC 4.2.1.16) is limited in both humans (Darling et al., Am J Physiol Endocrinol Metab. 2000; 278:E877-84) and rats (Harper, et al., Physiol Rev. 1970; 50:428-39). Thus, an increase in dietary threonine without an increase in total protein intake results in expansion of the plasma threonine pool without toxicity if diets provide <15 times the normal level of threonine. The concentration of threonine in plasma showed the largest increase with ingestion of GMP compared with the casein and amino acid diet in all 3 experiments.

Degradation of threonine to glycine via threonine dehydrogenase (EC 1.1.1.103) is a major catabolic pathway in rats but not in humans (Darling, et al., Am J Physiol Endocrinol Metab. 2000; 278:E877-84). Elevated glycine levels are potentially neurotoxic in the brain due to the glycinergic neurotransmitter system that can inhibit or stimulate transmission of nervous impulses (Spencer et al., J Neurosci. 1989; 9:2718-36). However, our demonstration of no increase in the concentration of glycine in both plasma and brain suggests that feeding a GMP diet that provides 3 times the normal intake of threonine is not sufficient to modify the concentration of glycine in brain. Taken together, these findings support the safety of dietary GMP.

In addition, the 11% decrease in the concentration of Phe in plasma of PKU mice fed GMP compared with the amino acid diet for 47 d is a positive finding for the nutritional management of PKU. The finding of greatest relevance to the management of PKU and the known neurotoxic effects of Phe is our observation that PKU mice fed GMP compared with the amino acid diet had a 20% decrease in the concentrations of Phe in 5 sections of brain. The concentration of Phe in brain is the best correlate of mental impairment in individuals with PKU (Donlon et al., Metabolic and Molecular Basis of Inherited Disease, in Scriver et al., editors, 8th ed. 77th chapter, Hyperphenylalaninemia: Phenylalanine Hydroxylase Deficiency, New York: McGraw-Hill; 2007). The most likely explanation for the reduced concentration of Phe in the brain of PKU mice fed GMP is that elevated plasma levels of LNAA due to ingestion of GMP competitively inhibit Phe transport across the blood brain barrier via the LNAA carrier protein that has a significantly lower Km in the brain compared with the gut. This conclusion is supported by a significant inverse correlation between higher plasma concentrations of threonine, isoleucine, and valine and lower brain concentration of Phe. Interestingly, previous research demonstrates that isoleucine, but not threonine, competitively inhibits Phe transport in rat brain (Tovar et al., J Neurochem. 1988; 51:1285-93).

In summary, we demonstrate that PKU mice fed a diet with 20% GMP supplemented with IAA compared with an amino acid diet show similar growth and lower concentrations of Phe in plasma and the brain. These data establish that GMP can be formulated into a nutritionally adequate complete protein for growing mice and suggest that long-term feeding studies may provide further insight into the metabolism of GMP. Our findings support continued research to establish the efficacy of foods and beverages made with GMP in the nutritional management of PKU in humans.

Example 2

Palatability of Foods Made with GMP and Supplemental AAs

In this Example, Applicants made a variety of palatable, low-phe foods and beverages with GMP and assessed their acceptability by conducting consumer sensory studies in individuals with PKU. Results demonstrate acceptability of products made with GMP.

Materials and Methods

Foods and Beverages.

Figure 4:
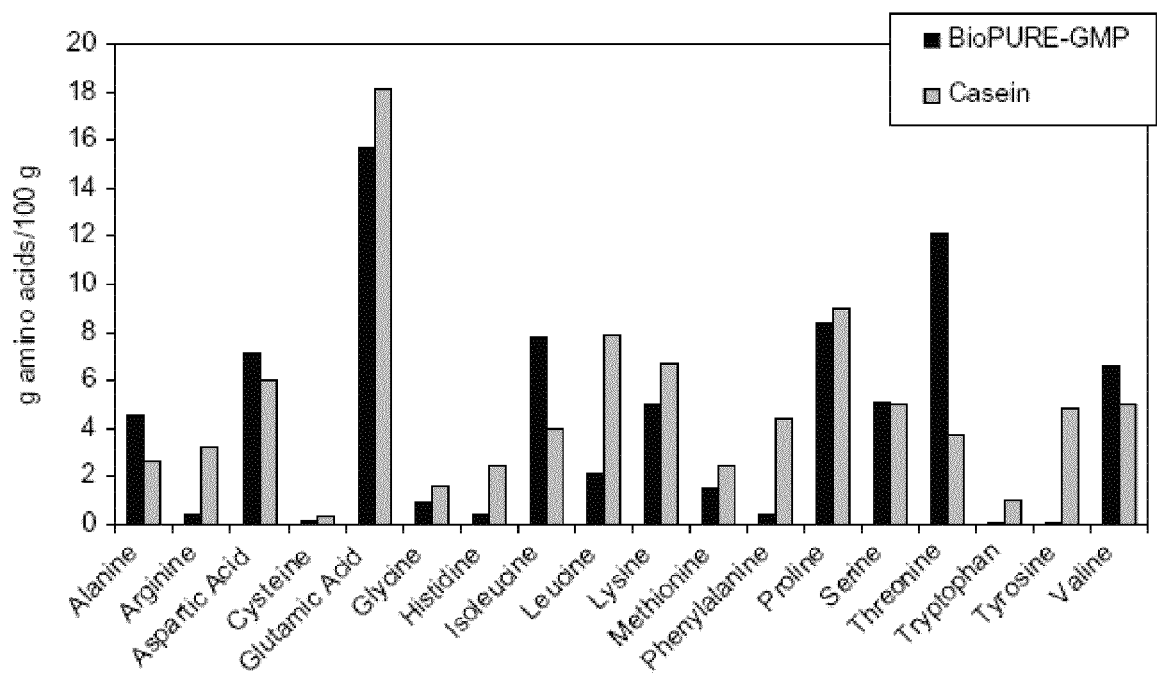
FIG. 4 shows the amino acid profile of glycomacropeptide (BioPURE-GMP; Davisco Foods International Inc., LeSueur, Minn.) and casein (ALACID; New Zealand Milk Products, Santa Rosa, Calif.) expressed as g amino acid per 100 g product.

Strawberry pudding, strawberry fruit leather, chocolate beverage, snack cracker and an orange sports beverage containing GMP were developed for this study in the Food Applications Laboratory at the Wisconsin Center for Dairy Research (CDR), University of Wisconsin-Madison (UW). The BioPURE-GMP (Davisco Foods International, Inc., LeSueur, Minn.) was used to formulate GMP products. The amino acid profile of BioPURE-GMP compared to casein is shown in FIG. 4.

A commercial amino acid-based chocolate beverage and low protein cracker were included in the taste testing to provide comparisons between GMP products and products currently used in the PKU diet. The nitrogen concentration of GMP and amino acid beverages was similar. The energy and protein content of all foods tested is provided in Table 6.

TABLE 6

Mean acceptability ratings of foods and beverages made with GMP as tested in individuals with PKU

| Product | No. of subjects | Appearance | Odor | Taste | Texture | Overall |
|---|---|---|---|---|---|---|
| A. Acceptability ratings for GMP pudding, fruit leather, and sports beverage | | | | | | |
| GMP strawberry pudding | 31 | 4.0 ± 0.7 | 3.6 ± 1.1 | 4.2 ± 1.0 | 4.1 ± 0.8 | 4.2 ± 0.9 |
| GMP strawberry fruit leather | 31 | 3.4 ± 0.8 | 3.8 ± 0.9 | 3.4 ± 1.1 | 3.0 ± 0.9 | 3.4 ± 1.0 |
| GMP orange sports beverage | 18 | 4.1 ± 0.6 | 36 ± 0.9 | 2.9 ± 1.2 | 3.8 ± 1.0 | 3.3 ± 1.1 |
| B. Acceptability rating for GMP and amino acid-based chocolate beverage | | | | | | |
| GMP chocolate beverage | 32 | 3.8 ± 0.8[a] | 3.7 ± 1.0[a] | 3.2 ± 1.1[a] | 3.3 ± 1.0 | 3.3 ± 1.0[a] |
| Amino acid chocolate beverage | 32 | 3.1 ± 1.1[b] | 2.8 ± 1.3[b] | 2.2 ± 1.3[b] | 3.1 ± 1.1 | 2.5 ± 1.4[b] |

TABLE 6-continued

Mean acceptability ratings of foods and beverages made with GMP as tested in individuals with PKU

| Product | No. of subjects | Appearance | Odor | Taste | Texture | Overall |
|---|---|---|---|---|---|---|
| C. Acceptability ratings for GMP and a low-protein snack cracker | | | | | | |
| GMP snack crackers | 18 | $3.8 \pm 0.6^a$ | $3.9 \pm 0.8^a$ | $3.7 \pm 0.8^a$ | $3.6 \pm 0.9$ | $3.6 \pm 1.4$ |
| Low protein crackers | 18 | $3.2 \pm 0.9^b$ | $3.2 \pm 0.8^b$ | $2.9 \pm 1.1^b$ | $3.2 \pm 1.2$ | $2.9 \pm 1.3$ |

The energy and protein content of the foods tested is as follows:
GMP strawberry pudding, 213 kcal and 5.7 g protein per ½ cup serving (113 g);
GMP fruit leather, 60 kcal and 0.7 g protein per 15 g;
GMP orange sports beverage, 67 kcal and 7.9 g protein per 8 oz (234 g);
GMP chocolate beverage, 148 kcal and 10.2 g protein per 8 oz (236 g);
amino acid chocolate beverage, 187 kcal and 11.4 g protein per 8 oz (202 g);
GMP snack crackers, 110 kcal and 1.3 g protein per 30 g;
low protein crackers, 135 kcal and 0.1 g protein per 30 g.
Means ± standard deviation (score reference: 1, dislike very much; 2, dislike; 3, neither like nor dislike; 4, like; 5, like very much).
Means with different letter superscripts (a or b) in the same column for B. or C. do significantly differ at p 0.05.

Sensory Studies to Assess Acceptability of Foods and Beverages.

The protocol for sensory studies was approved by the Social and Behavioral Sciences Institutional Review Board, UW. Three sensory studies were performed with PKU subjects attending PKU Summer Camps in 2004 and 2005 and a PKU family conference in 2005 (n=49; age range 12-42 years). The studies were conducted in the Sensory Analysis Laboratory, Department of Food Science, UW or at the Waisman Center.

Test samples of 20-30 g were presented to subjects in balanced random order with three digit blind codes. Foods and beverages were rated using a five-point hedonic scale (1=dislike very much, 2=dislike, 3=neither like nor dislike, 4=like, 5=like very much) to evaluate five sensory categories, including appearance, odor, taste, texture and overall acceptability.

Statistical Analysis.

Dependent t-test was performed to analyze mean acceptability scores for GMP chocolate beverage and amino acid chocolate beverage. Group means were considered to be significantly different at p 6 0.05, as determined by a two-tailed t-test using Statistical Analysis Software package (SAS Institutes Inc., Version 9.1.3, Cary, N.C., USA). Acceptability scores for GMP snack crackers and low protein crackers were compared using general linear model procedure (PROC GLM) followed by Fisher's least square means for mean separation. Data are presented as means with standard deviations.

Results

PKU subjects tasted a total of 7 products during PKU events in 2004 and 2005 (Table 6). Among these foods and beverages, GMP strawberry pudding was the most acceptable (overall score of 4.2±0.9) and other foods in order of overall acceptability were GMP snack crackers (3.6±1.4), GMP strawberry fruit leather (3.4±1.0), GMP chocolate beverage (3.3±1.0), GMP orange sports beverage (3.3±1.1), and low protein crackers (2.9±1.3). An amino acid chocolate beverage was least acceptable (2.5±1.4). A score of <3 indicates that a food or beverage is unacceptable with respect to a specific category, whereas a score of 3 indicates neutral acceptance.

PKU subjects rated the appearance, odor, taste and overall acceptability of GMP chocolate beverage as significantly more acceptable compared to the amino acid based beverage ($p \le 0.05$, Table 6B). Appearance, odor and taste of the GMP snack crackers were rated as significantly more acceptable compared to the low protein cracker ($p \le 0.05$), but overall acceptability was not significantly different between the two types of crackers (Table 6C).

Discussion

These data demonstrate that the functional properties of GMP are especially well suited for use in beverages and semi-solid foods such as pudding. For example, GMP is soluble in acid with an isoelectric point of below 3.8, forms gels or foams, and has good heat stability. GMP actually enhanced the chocolate flavor used in the beverage with the added feature that the chocolate flavor helped to mask the dairy flavor of GMP. These data suggest that GMP can be used to make a beverage that is more palatable than the amino acid formulas currently required as the primary source of protein in the PKU diet.

Example 3

Case Study of Adult with PKU Following a Ten Week GNP Diet

This Example is a case report of a 29 year old male with PKU who used GMP-based foods as his sole protein source for a ten week period. The test subject reported that GMP-based foods tasted better than the standard amino acid formula, and his plasma levels of Phe were lower overall for the ten weeks that he consumed the GMP-based diet.

Approval was granted by the Health Sciences Institutional Review Board, University of Wisconsin-Madison to conduct an outpatient study in subjects with PKU to evaluate the safety and acceptability of dietary GMP. A 29-year-old male PKU subject with a genotype of R261Q and R408W was studied. The subject adhered to the low-Phe diet from birth through 12 years but was of diet during adolescence, which resulted in the development of spastic quadriparesis and a seizure disorder that was treated with standard anticonvulsant therapy. The subject completed a 15-week study comparing GMP with his usual prescribed amino acid formula (Phenylade and Amino Acid Blend; Applied Nutrition, Cedar Knolls, N.J., USA) as the primary source of dietary protein.

The protocol consisted of a diet in which he consumed his usual amino acid formula for the first 3 weeks and the last 2 weeks of the study. During the middle 10 weeks of the study, GMP food products chosen by the subject replaced all of the amino acid formula and included: GMP orange sports beverage (28 oz/day; 28 g protein), GMP pudding (1.5 cups/day; 15 g protein) and GMP snack bar (1 bar/day; 5 g protein). See Table 7 for the nutritional composition of the GMP foods.

For six weeks of the study, weighed portions of food with precisely controlled Phe content were sent to the subject's home. The Phe content of the diets was determined by analysis of selected foods for amino acid content and calculation of Phe content for the remaining foods matched in quantity and packing lot in both diets (US Department of Agriculture ARS (2005) USDA Nurient Database for Standard Reference, Release 18). For the remaining 9 weeks of the study, the subject purchased and weighed his own food using menus planned with the metabolic dietician. Although Phe intake was well-controlled for 15 weeks, the results for Phe concentrations in blood and plasma presented here are based on the 6 weeks that food was provided to the subject.

TABLE 7

Nutritional composition of GMP food products[a]

| Product | Serving size | Energy [kJ (kcal)] | Protein (g) | Phe (mg) |
|---|---|---|---|---|
| Orange sports drink | 340 g (12 oz) | 419 (100) | 12 | 33 |
| Chocolate beverage | 227 g (8 oz) | 628 (150) | 10 | 33 |
| Caramel beverage | 227 g (8 oz) | 670 (160) | 10 | 26 |
| Strawberry pudding | 114 g (½ cup) | 921 (220) | 5 | 13 |
| Chocolate pudding | 114 g (½ cup) | 921 (220) | 5 | 21 |
| Ranch dressing | 45 g (1.5 oz) | 419 (100) | 5 | 15 |
| Cinnamon crunch bar | 55 g (1 bar) | 711 (170) | 5 | 14 |

[a]GMP food products were developed in the Wisconsin Center for Dairy Research except for the ranch dressing and cinnamon crunch bar, which were developed by Cambrooke Foods of Boston.

The macronutrient profile provided by the amino acid and GMP diets was constant and included: 10 880-11 300 kJ/day (2600-2700 kcal/day), 10-11% energy from protein (0.84 g protein/kg), 24-26% energy from fat, and 63-66% energy from carbohydrate. The subject maintained a body weight of 87 kg during the study. The daily Phe content was 1100 mg Phe for 4 weeks and 1180 mg Phe for 2 weeks; this provided approximately 13 mg Phe per kg of body weight. The amino acid formula and GMP food products each provided 0.6 g protein per kg body weight. The GMP food products were supplemented to provide 130%, or 150% for tyrosine, of the amino acid scoring pattern for a complete protein for the following limiting amino acids, expressed as mg amino acid per g GMP protein: histidine, 23; leucine, 72; tryptophan, 9; and tyrosine, 71. A multivitamin/mineral supplement, a calcium/phosphorus supplement and 500 mg of L-tyrosine twice a day were taken with the GMP diet to ensure intakes similar to those provided by the amino acid formula.

Blood samples were obtained after an overnight fast and prior to breakfast for determination of Phe concentration using one of two analytical methods known to give different values (Gregory et of (2007) Genet Med 9:761-765). Tandem mass spectroscopy (MS/MS) was used for analysis of Phe concentrations in blood spots collected on filter paper by the subject between 09:00 and 09:30 Rashed et al. (1995) Pediatr Res 38: 324-331) and a Beckman 6300 amino acid analyzer was used for analysis of the plasma amino acid profile obtained by venepuncture in a local clinic between 12:00 and 12:30 (Slocum and. Cummings (1991), Amino Acid Anaylsis of Physiological Samples, in Hommes, F A, ed., Techniques in Diagnostic Human Biochemical Genetics: A Laboratory Manual. New York: Wiley-Liss, 87-126).

Figure 5:
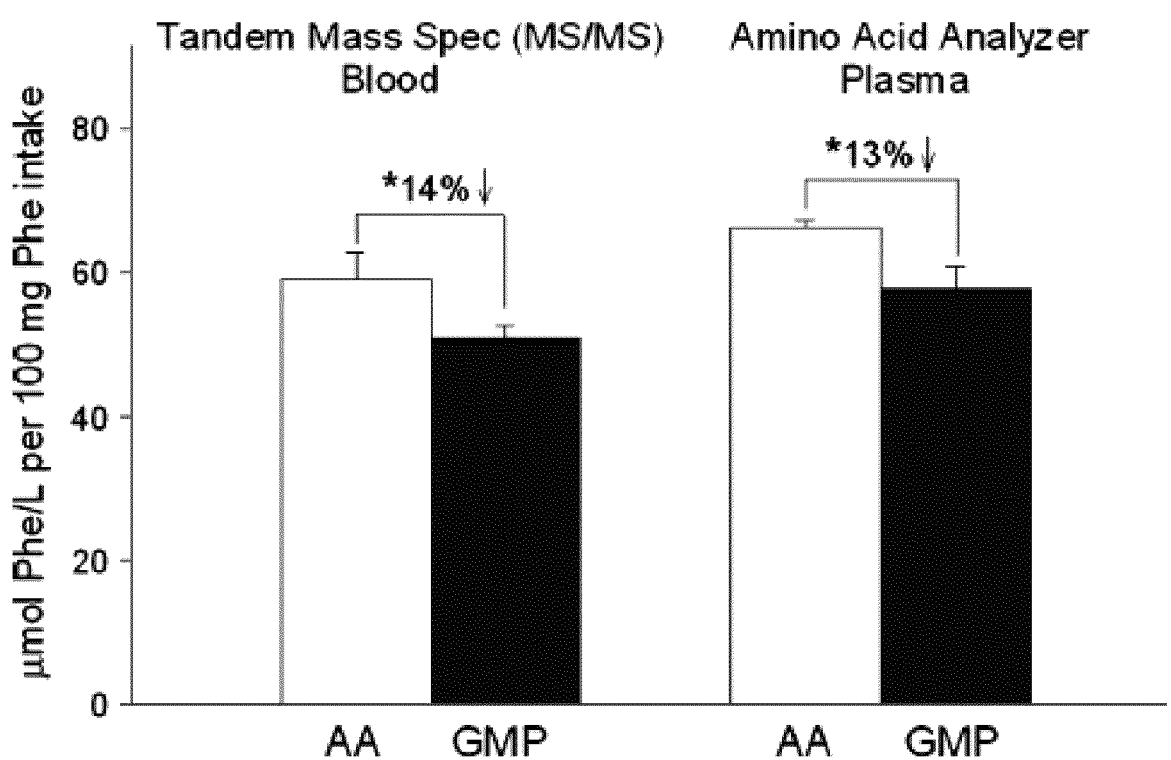
FIG. 5 shows mean Phe concentrations obtained after an overnight fast before breakfast from a single PKU subject fed an amino acid (AA) or glycomacropeptide (GMP) diet for 15 weeks at home. Data are shown for 6 weeks of the 15-week study period when only foods with known Phe content were provided to the subject: weeks 3 and 15 (AA diet) and weeks 4, 7, 11 and 13 (GMP diet). Phe concentrations in blood and plasma were corrected for Phe intake and expressed as mmol Phe/L per 100 mg Phe intake. Phe concentration was determined using one of two methods, blood spot collection analysed with tandem mass spectroscopy (MS/MS) and measurement of plasma Phe with an AA analyser. Values are means±SE; AA diet (n=4 plasma Phe and n=4 blood Phe), GMP diet (n=4 plasma Phe and n=8 blood Phe). *Different from the AA diet, p<0.05.

Statistical differences in blood and plasma amino acid concentrations for the amino acid and GMP dietary periods were evaluated by t-test with the assumption that the amino acid measurements were independent over time; $p<0.05$ was considered significant. When expressed relative to 100 mg of Phe intake based on provision of meals with known Phe content, mean fasting plasma and blood Phe concentrations were significantly reduced by 13-14% with consumption of the GMP diet compared with the amino acid diet (FIG. 5). The absolute concentration of Phe in plasma was reduced by approximately 10% (from 736 to 667 mmol/L) with consumption of the GMP diet compared with the amino acid diet (see Table 8). Plasma tyrosine concentration was not significantly different with the GMP and amino acid diets. No adverse effects were noted with consumption of the GMP diet based on physical examinations and the results of chemistry panel analyses which included electrolytes, albumin, prealbumin, and liver function tests.

Consistent with the amino acid profile of GMP and studies in the PKU mouse (see Example 1), significant increases in plasma concentrations of the LNAA were noted with ingestion of the GMP diet compared with the amino acid diet (Table 8). Threonine increased 2.6-fold, isoleucine increased 1.7-fold, and the sum of the branched-chain amino acids increased 16% with the GMP diet. Interestingly, this subject was previously given a supplementation trial with a mixture of indispensable LNAA (PreKUnil; NiLab, Korsoer, Denmark), but this was stopped because his seizures became worse. The LNAA preparation contained a larger proportion of amino acids from tyrosine and tryptophan and proportionately less from threonine and the branched-chain amino acids than GMP, which contains approximately 80% of indispensable amino acid content from a combination of threonine and the branched-chain amino acids. Thus, GMP appears to provide a safe dietary source of LNAA for this subject. Plasma concentration of proline increased 40% with the GMP diet association with a 2-fold increase in proline ingestion with GMP compared with the amino acid formula. There was a small increase in plasma concentration of glutamine and citrulline with the GMP diet compared with the amino acid diet that was not associated with a change in liver function tests.

TABLE 8

Fasting concentrations of amino acids in plasma with ingestion of the amino acid diet compared to the GMP diet in a single PKU subject[a]

| | Concentration (imol/L) | | |
|---|---|---|---|
| Amino acid | Amino acid diet | GMP diet | Normal range |
| Alanine | 296 ± 26 | 331 ± 5 | 177-583 |
| Arginine | 58 ± 2 | 62 ± 3 | 15-128 |
| Citrulline | 26 ± 2 | 48 ± 7* | 12-55 |
| Cystine | 31 ± 1 | 42 ± 5 | 5-82 |
| Glutamate | 46 ± 10 | 53 ± 7 | 10-131 |
| Glutamine | 698 ± 22 | 858 ± 16** | 205-756 |
| Glycine | 428 ± 7 | 428 ± 22 | 151-490 |
| Histidine | 69 ± 3 | 75 ± 2 | 41-125 |
| Isoleucine | 42 ± 3 | 69 ± 1** | 30-108 |
| Leucine | 92 ± 3 | 91 ± 3 | 72-201 |
| Lysine | 189 ± 8 | 201 ± 5 | 48-284 |
| Methionine | 19 ± 1 | 19 ± 3 | 10-42 |
| Ornithine | 61 ± 7 | 51 ± 6 | 48-195 |
| Phenylalanine | 736 ± 13 | 667 ± 24[b] | 35-85 |
| Proline | 153 ± 7 | 214 ± 13** | 97-329 |
| Serine | 95 ± 1 | 88 ± 8 | 58-181 |
| Taurine | 65 ± 6 | 59 ± 13 | 54-210 |

TABLE 8-continued

Fasting concentrations of amino acids in plasma with ingestion of the amino acid diet compared to the GMP diet in a single PKU subject[a]

| Amino acid | Concentration (imol/L) | | |
|---|---|---|---|
| | Amino acid diet | GMP diet | Normal range |
| Threonine | 95 ± 4 | 246 ± 12** | 60-225 |
| Tryptophan | 33 ± 2 | 35 ± 2 | 10-140 |
| Tyrosine | 53 ± 5 | 45 ± 6 | 34-112 |
| Valine | 241 ± 15 | 275 ± 14 | 119-336 |
| BCAA[c] | 374 ± 17 | 435 ± 15* | 221-645 |

*, **Different from the AA diet, *$p < 0.05$, **$p < 0.01$.
[a]Values are mean ± TSE, n = 4; blood samples were obtained after an overnight fast and prior to breakfast between 12:00 and 12:30 on different days distributed across the 5 weeks of the amino acid diet and the 10 weeks of the GMP diet.
[b]p = 0.073.
[c]BCAA = sum of leucine, isoleucine, and valine.

Overall, the subject enjoyed the GMP diet and reported that he felt more alert with that diet than with his usual amino acid diet. Because the subject enjoyed the GMP food products, he was more inclined to distribute them throughout the day. He consumed GMP food products approximately three times per day compared with once per day for the amino acid formula. It is well known that spacing the amino acid medical foods for PKU throughout the day lowers blood Phe levels owing to improved utilization of amino acids for protein synthesis. Thus, one explanation for the reduced blood Phe levels with consumption of GMP is improved protein synthesis due to consumption of a sufficient amount of high-quality protein throughout the day. Alternatively, the greater intake of LNAA with GMP may have contributed to the decrease in plasma Phe levels, particularly the high intake of threonine (~70 mg per kg per day).

In sum, compliance with the highly restrictive, low-Phe diet required for the management of PKU remains poor during adolescence and adulthood, resulting in elevated blood Phe levels, neuropsychological deterioration, and the tragic consequences of maternal PKU. Dietary GMP, an abundant food ingredient naturally low in Phe content, provides an innovative approach to improving the nutritional management of PKU. This Example indicates that incorporation of low-Phe foods and beverages made with GMP into the PKU diet improves the taste, variety and convenience of the diet. A more tasty and versatile low-Phe diet may lead to improved dietary compliance, metabolic control and ultimately quality of life for individuals with PKU.

Example 4

Eleven Subject Clinical Trial Comparing GMP Supplemented with Limiting Amino Acids to Amino Acid Formula as Primary Protein Source for Nutritional Management of PKU This example shows that a diet using GMP supplemented with limiting amino acids as a protein source is a safe and highly acceptable alternative to synthetic AA formulas in the nutritional management of PKU. As an intact protein source, GMP improves protein retention and phenylalanine utilization compared with AAs.

To further evaluate the potential benefits of GMP in the PKU diet, an 8-d clinical investigation was conducted in individuals with PKU. The objective was to investigate the effects of substituting GMP food products for the AA formula on acceptability, safety, plasma AA concentrations, and measures of protein utilization in subjects with PKU.

Subjects and Methods

Subjects.

Twelve subjects with PKU who were routinely monitored at the Biochemical Genetics Program, the Waisman Center, the University of Wisconsin-Madison, participated in this study between March 2006 and June 2008. One subject (age: 10 y) withdrew from the study because she was unable to complete the protocol. Thus, data from 11 subjects (age range: 11-31 y; 7 males and 4 females) are reported (See Table 9). The University of Wisconsin-Madison Health Sciences Institutional Review Board approved this study.

Criteria for participation included a diagnosis of classical or variant PKU and a willingness to consume ≥50% of the prescribed volume of the AA formula. Optimal control of plasma phenylalanine concentrations, however, was not a prerequisite for participation. Optimal control includes maintenance of phenylalanine concentrations between 120 and 360 μmol/L for neonates through age 12 y, between 120 and 600 μmol/L for adolescents, and <900 μmol/L for adults. The diagnosis of PKU was based on concentration of phenylalanine measured before initiation of dietary treatment during infancy; those with classical PKU show phenylalanine concentrations of ≥1200 μmol/L (see Table 9). All subjects in this study were diagnosed with classical PKU, except for one subject who was determined to have a variant form of PKU (subject 1).

Mutation analysis was completed for each subject by DNA sequencing of the PAH gene (Laboratory Service Section, Texas Department of State Health Services, Austin, Tex.) using primers designed by Guldberg et al. (Hum Mol Genet 1993; 2:1703-7). All subjects were compound heterozygous for PAH mutations (Table 9). Five subjects showed 2 copies of mutations considered to express primarily a classical phenotype and 6 subjects showed a classical mutation and a mutation observed in PKU patients with variant and/or non-PKU hyperphenylalaninemia mutations.

Because a formal evaluation of each subject's dietary prescription had not been completed within 2 y of study recruitment, a phenylalanine allowance for all subjects was determined before study initiation. For this study, phenylalanine allowance was defined as the amount of dietary phenylalanine intake that allowed for a constant plasma phenylalanine concentration (±5% variance) as determined by sequential increases in phenylalanine intake with frequent monitoring of blood phenylalanine concentrations in blood spots. Each subject's dietary phenylalanine allowance was verified by completing one or more "dry runs" in which all food, beverages, and formula were provided for a 5-d period with measurement of phenylalanine concentrations in blood spots before and at the end of each dry run. Plasma phenylalanine concentrations at the initiation of the study ranged from 192 μmol/L (subject 10) to 1011 μmol/L (subject 2; Table 9). To maintain these plasma phenylalanine concentrations, the dietary phenylalanine allowance for the subjects ranged from 5.8 mg/kg (subject 10) to 26.7 mg/kg (subject 2).

TABLE 9

Individual characteristics of 11 subjects with phenylketonuria

| Subject no./sex | Age at study initiation y | Height/ weight cm/kg | Phenylalanine concentration at diagnosis' µmo/L | Age at diagnosis' d | Mutation | Baseline plasma phenylalanine[2] µmol/L | Dietary phenylalanine allowance per mg | Dietary phenylalanine allowance per mg |
|---|---|---|---|---|---|---|---|---|
| 1/M | 27 | 173/73 | 1270 | 35 | R408W IVS12nt1g→a | 640 | 1151 | 15.8 |
| 2/M | 29 | 170/67 | 2208 | 15 | R408W R261Q | 1011 | 1793 | 26.7 |
| 3/M | 14 | 164/52 | 1210 | 8 | R408W IVS10nt-11g→a | 1009 | 673 | 13.0 |
| 4/M | 11 | 137/35 | 2051 | 7 | IVS4nt5g→t IVS12nt1g→a | 767 | 372 | 10.7 |
| 5/M | 12 | 148/45 | 2154 | 7 | R408W Y356N | 690 | 979 | 21.6 |
| 6/F | 23 | 94/51 | 1488 | 10 | R408W IVS12nt1g→a | 536 | 545 | 10.6 |
| 7/F | 28 | 159/64 | 2632 | 11 | R408W L242F | 603 | 545 | 8.3 |
| 8/M | 27 | 170/76 | 1924 | 11 | R261Q E280K | 810 | 971 | 12.8 |
| 9/F | 20 | 93/64 | 1016 | 10 | L48S F299C | 331 | 378 | 5.9 |
| 10/F | 31 | 157/70 | 1876 | 15 | R408W F299C | 192 | 408 | 5.8 |
| 11/M | 28 | 180/91 | 3122 | 13 | IVS1nt5g→t IVS12nt1g→a | 392 | 711 | 7.8 |

[1]Age and phenylalanine concentrations at diagnosis represent values when diet treatment was initiated during infancy.
[2]Values represent concentrations of phenylalanine in plasma 2.5 h after eating breakfast on day 3 while consuming the prescribed amino acid diet.

Study Protocol.

Each subject served as his or her own control in this metabolic study, which included 2 dietary treatments of 4 d each: the AA diet (days 1-4) and the GMP diet (days 5-8). One 24-h menu was designed for the AA diet and another for the GMP diet; the same menu was repeated on all days of each diet treatment (Table 10). In each diet, the AA formula or GMP products were divided equally in each of 3 meals during the day. Distribution of protein equivalents throughout the day improves protein utilization and can lower plasma phenylalanine concentrations. During the study, all food, beverages, snacks, formula, and GMP products were weighed in grams by trained dietary staff at the Waisman Center or the University of Wisconsin Clinical and Translational Research Core (UW-CTRC). To ensure identical intake on all days of the study, subjects were encouraged to consume all foods and beverages. No subject failed to do this.

TABLE 10

Comparison of typical menus for the amino acid (AA) and the glycomacropeptide (GMP) diets[1]

| AA diet | GMP diet |
|---|---|
| Breakfast (103 mg phenylalanine, 14 g protein) | Breakfast (102 mg phenylalanine, 14 g protein) |
| 177 mL PKU formula[2] (0 mg phenylalanine) | 296 mL GMP chocolate beverage (51 mg phenylalanine) |
| 30 g Cold cereal (51 mg phenylalanine) | 30 g Cold cereal (51 mg phenylalanine) |
| 11 g Pretzels (52 mg phenylalanine) | Lunch (124 mg phenylalanine, 13 g protein) |
| Lunch (124 mg phenylalanine, 15 g protein) | 148 mL GMP chocolate beverage (24 mg phenylalanine) |
| 177 mL PKU formula[2] (0 mg phenylalanine) | 113 g (½ cup) GMP chocolate pudding (38 mg phenylalanine) |
| 12.5 g Cinnamon toast (62 mg phenylalanine) | Cheese sandwich (45 mg phenylalanine; 64 g low-protein bread, |
| Cheese sandwich (45 mg phenylalanine; 64 g low-protein bread) | 1 Slice low-protein cheese, 8.7 g butter) |
| 1 Slice low-protein cheese, 8.7 g butter) | 125 g Peaches (17 mg phenylalanine) |
| 125 g Peaches (17 mg phenylalanine) | Dinner (226 mg phenylalanine, 18 g protein) |
| Dinner (220 mg phenylalanine, 18 g protein) | 1 GMP bar (33 mg phenylalanine) |
| 177 mL PKU formula[2] (0 mg phenylalanine) | 237 mL GMP sports beverage (19 mg phenylalanine) |
| 9 g Bowtie pasta (53 mg phenylalanine) | Pasta Alfredo (61 mg phenylalanine; 60 g low-protein pasta, |
| Pasta Alfredo (61 mg phenylalanine; 60 g low-protein pasta, | 5 g Regular bowtie pasta, 88 g low-protein Alfredo sauce) |
| 5 g Regular bowtie pasta, 88 g low-protein Alfredo sauce) | 92 g Broccoli, 50 g carrots and 14 g butter (105 mg phenylalanine) |
| 92 g Broccoli, 50 g carrots and 14 g butter (105 mg phenylalanine) | 140 g Pears (7 mg phenylalanine) |
| 140 g Pears (7 mg phenylalanine) | 237 mL Lemonade (0 mg phenylalanine) |
| 237 mL Lemonade (0 mg phenylalanine) | |

[1]All foods were measured on a gram scale by trained staff. Since this study was completed, improved recipes have been developed to further lower the phenylalanine content of all of the GMP products shown in this typical menu (12). For example, a GMP bar can now be produced with only 14 mg phenylalanine compared with 33 mg phenylalanine, and the GMP chocolate pudding now contains 21 mg phenylalanine compared with 38 mg phenylalanine in the original formulation used for this research. PKU, phenylketonuria.
[2]The PKU formula used in this menu is 40 g Phenex 2 (Abbott Laboratories, Columbus, OH).

Each subject was provided with all food and formula to consume at home for 2 d before initiation of the study and for days 1 and 2 of the AA diet. Before dinner on day 2, each subject was admitted to the UW-CTRC for continuation of the AA diet (days 3 and 4) and for 4 d of the GMP diet (days 5-8). A physical exam was completed on all days of the UW-CTRC admission. All subjects were required to walk or complete physical activity 2-3 times/d to allow for an activity level consistent with their usual routine. Timing of meals and snacks was also similar to each subject's usual routine.

On days 1 and 2, each subject collected a blood spot on filter paper for phenylalanine and tyrosine analysis. During the UW-CTRC admission, blood was drawn daily for plasma AA and automated chemistry panel analysis to measure serum concentrations of prealbumin, albumin, total protein, electrolytes, glucose, blood urea nitrogen (BUN), creatinine, calcium, magnesium, phosphate, uric acid, total and direct bilirubin, alkaline phosphatase, and liver enzymes (γ-glutamyltranspeptidase, alanine aminotransferase, aspartate aminotransferase, and lactic dehydrogenase). All postprandial blood samples were drawn daily 3 h after the start of breakfast or 2.5 h after eating breakfast (days 3-8).

After the first 5 subjects had completed the protocol, the Data Safety and Monitoring Board evaluated the protocol and study progress. As a result of the board's suggestions, blood draws for chemistry panels were eliminated on the first 2 d of the GMP diet (days 5 and 6), and an additional fasting blood sample was added before breakfast on the last 2 d of the AA diet (days 3 and 4) and on the last 2 d of the GMP diet (days 7 and 8) for the remaining 6 subjects. All fasting samples were analyzed for plasma AAs. The mean age of the 6 subjects for whom both fasting and postprandial blood samples were obtained was 26±2 y and included 4 females and 2 males (subjects 6-11; Table 9).

Because the GMP food products were not supplemented with vitamins and minerals, all subjects were given a complete multivitamin with mineral supplement (Phlexy-Vits; Nutritia North America, Gaithersburg, Md.) or a combination of Theragran M (Walgreen Co, Deerfield, Ill.) and Target-Mins (Country Life, Hauppauge, N.Y.) during the GMP diet. Any subject consuming a formula or formulas that did not contain vitamins and minerals was given the same supplements provided for the GMP diet during the AA diet. Additional calcium was given, if needed, to meet Dietary Reference Intake (DRI) recommendations for age (Institute of Medicine, Dietary Reference Intakes for Energy, Carbohydrates, Fiber, Fat, Protein and Amino Acids, Washington D.C.: National Academy Press, 2002).

Study Diets.

GMP (Bio-Pure GMP; Davisco, Le Sueur, Minn.) was analyzed for AA content at the University of Missouri Experimental Station Chemical Laboratory. The phenylalanine content for the commercial GMP was 0.4 g phenylalanine/100 g GMP with a protein content of 86.0 g/100 g GMP. This GMP was used for 3 subjects with a higher phenylalanine tolerance. For 9 subjects with a lower phenylalanine tolerance, the original stock of GMP was further purified to reduce the phenylalanine content to an average of 0.21±0.01 g phenylalanine/ 100 g GMP with an average protein content of 75.0±0.7 g/100 g GMP. Purification of the GMP decreased only the phenylalanine content; the proportion of the other AAs remained unchanged in the purified GMP compared with the commercial GMP.

The GMP was supplemented with 4 limiting AAs, expressed as the final concentration in milligrams AA per gram GMP protein: histidine, 23; leucine, 72; methionine, 28; and tryptophan, 9. This is equivalent to 130% of estimated needs on the basis of the 2002 DRIs (Institute of Medicine, Dietary Reference Intakes for Energy, Carbohydrates, Fiber, Fat, Protein and Amino Acids, Washington D.C.: National Academy Press, 2002). Because tyrosine is an indispensable AA in PKU, tyrosine was supplemented at 150% of estimated needs for a final concentration of 71 mg/g GMP protein. For the GMP diet, no attempt was made to duplicate the concentration of supplemental tyrosine found in the various formulas consumed by each subject because, in most cases, the tyrosine content of the formula was substantially greater than the estimated needs. Thus, for all subjects, tyrosine intake in the AA diet was greater than tyrosine consumed when GMP products were substituted.

Low-phenylalanine food products made with GMP as the protein source were developed for this study by the Wisconsin Center for Dairy Research, the University of Wisconsin-Madison. Before initiation of the study, each subject tasted a variety of food products made with GMP and selected 2 to 3 products that would be included in menus for the GMP diet. GMP beverages and foods included an orange-flavored sports beverage, a chocolate-flavored or caramel-flavored beverage, chocolate or strawberry pudding, and a cinnamon crunch bar (as in Example 3; see Table 7). The range of phenylalanine content in the GMP food products varied with the purity of the GMP and the additional ingredients used to produce these foods and beverages, but, in general, a serving of GMP food products provided 5-10 g protein and 15-30 mg phenylalanine.

Diet Composition.

The AA and GMP diets were calculated on the basis of a prestudy evaluation of each subject's phenylalanine allowance and were controlled for energy, protein, phenylalanine, and fat (see Table 11). The AA diet (days 1-4) included a subject's usual AA formula, which was different for each subject. For the GMP diet (days 5-8), GMP products were substituted for a subject's entire daily intake of AA formula. The phenylalanine content of foods used to plan the menus was determined by AA analysis of selected foods and by calculation of phenylalanine content for the remaining foods. Foods that were not analyzed were matched in quantity, brand, and packing lot in both diets, whereas foods analyzed for phenylalanine content were used in variable amounts to account for the phenylalanine content of the GMP products.

Because of the limitations in data to quantitate the phenylalanine content of foods, dietary composites were collected for phenylalanine analysis to verify calculations of phenylalanine content. Thus, a duplicate of all food, formula, and GMP food products consumed by each subject during a 24-h period was collected for 2 d during both the AA diet and the GMP diet. Each duplicate was ground and freeze-dried, and an aliquot of each composite was sent to the University of Missouri for AA analysis. When comparing the composite analyses for each subject, phenylalanine content in the AA diet and the GMP diet was not significantly different ($P=0.061$).

TABLE 11

Nutrient composition of amino acid (AA) and glycomacropeptide (GMP) diets[1]

| | AA diet | GMP diet |
|---|---|---|
| Energy (kcal/kg) | | |
| <18 y old | 56 ± 6 | 57 ± 5 |
| ≥18 y old | 35 ± 1 | 35 ± 2 |
| Energy from protein (%)[2] | 11 ± 1 | 10 ± 1 |

TABLE 11-continued

Nutrient composition of amino acid (AA) and glycomacropeptide (GMP) diets[1]

| | AA diet | GMP diet |
|---|---|---|
| Energy from fat (%)[3] | 24 ± 1 | 23 ± 1 |
| Phenylalanine intake (mg · kg⁻¹ · d⁻¹) | 13 ± 2 | 13 ± 2 |
| Tyrosine intake (mg · kg⁻¹ · d⁻¹) | 85 ± 9 | 51 ± 54 |

[1]Values are means ± SEMs and are based on calculated dietary intake; n = 11.
[2]Protein from synthetic AAs represents 75% of the total protein in the AA diet and only 10% of the total protein in the GMP diet (from supple¬ menting the GMP with limiting indispensable AAs). All other protein in the AA and GMP diets is from natural sources of intact protein.
[3]Total fat intake ranged from 18% to 31% of total energy. A low fat intake is typical in those with phenylketonuria, given their selection of carbohydrate-based foods and the low fat content of many AA formulas designed for older individuals with this disorder (28).
[4]Significantly different from the AA diet, P < 0.0001 (paired t test, pairing on subject).

Measurements.

The blood spots collected by each subject to establish their phenylalanine allowance and on prestudy days 1 and 2 were analyzed for phenylalanine and tyrosine by tandem mass spectrometry (MS/MS; data not shown). An AA profile was completed on all fasting and postprandial plasma samples collected on days 3-8 by using a Beckman 6300 amino acid analyzer (Beckman-Coulter Inc, Fullerton, Calif.) equipped with an ion chromatography system that uses postcolumn ninhydrin derivatization. The samples were deproteinized with sulfosalicylic acid, centrifuged (14,000×g; 5 min) and passed through a 0.2-μm syringe filter before adding an internal standard and injecting it into the column.

Serum chemistry profiles were analyzed by using standard techniques at the Clinical Laboratory, the University of Wisconsin-Madison Hospital and Clinics. Plasma insulin was measured in postprandial samples by using an radioimmunoassay specific for human insulin (Linco Research, St Charles, Mo.) on samples pooled within subjects for days 3+4 and days 7+8. Insulin-like growth factor I (IGF-I) was measured in postprandial plasma samples for days 4 and 8 after removal of IGF-binding proteins by HPLC; the recovery of IGF-1 was 85-90%.

Statistical Analysis.

All statistical analysis was conducted with the statistical program R for Mac OS X version 1.12 (R Project for Statistical Computing, Wirtschaftsuniversität, Vienna, Austria). After dietary composites were analyzed, AA values within each diet were averaged for each subject (n=2), and then values between both diets were compared by using paired t tests. Also, paired t tests, pairing on subject, were conducted to compare plasma AA values from the last day of the AA diet (day 4) to the last day of the GMP diet (day 8) for both postprandial and fasting samples. Changes in the chemistry panel and liver function tests were compared by using the same method. In addition, paired t tests were conducted to compare fasting and postprandial AA concentrations within each diet in the subset of 6 subjects from whom fasting plasma was available. All comparisons were considered statistically significant if P≤0.05. On the basis of the primary endpoint comparing plasma phenylalanine concentration on the last day of the AA diet (day 4) with the last day of the GMP diet (day 8), the achieved sample size (n=11) was sufficient to provide 80% power at P=0.05 if the change in plasma phenylalanine concentration was 150 μmol/L.

Results

Diet Acceptability and AA Composition.

After consuming the GMP diet for 4 d, 10 of 11 subjects claimed that the GMP products were superior in sensory qualities to their usual AA formula. Moreover, at the conclusion of the study, 6 of the 7 adult subjects expressed a strong preference to consume GMP products rather than their usual AA formula, if GMP became available to them as a dietary option.

Compared with current recommendations, the analyzed intake (mg amino acid/g of dietary protein) of all indispensable AAs met requirements for both the AA and GMP diets (World Health Organization, Protein and Amino Acid Requirements in Human Nutrition, Geneva Switzerland: United Nations University, 2007). However, AA analysis of the dietary composites indicated several significant differences in AA intake with ingestion of the AA diet compared with the GMP diet (see Table 12). Because GMP contains a high concentration of the LNAAs threonine and isoleucine, mean intakes of both of these AAs were significantly higher with the GMP than the AA diet. Despite supplementation of GMP with tyrosine at 150% of DRI and leucine, histidine, tryptophan, and methionine at 130% of the DRI, the intake of these AAs, with the exception of methionine, was significantly lower with the GMP than the AA diet. The intakes of other AAs that were significantly lower with ingestion of the GMP diet compared with the AA diet included the indispensable AA lysine and the dispensable AAs arginine, alanine, glycine, and taurine.

TABLE 12

Analyzed profile of amino acids (AAs) from 24-h composites of AA and glycomacropeptide (GMP) diets[1]

| AA | AA diet | GMP diet | P value[2] |
|---|---|---|---|
| | g amino acid/24-h diet | | |
| Alanine | 4.08 ± 0.32 | 3.15 ± 0.07 | 0.039 |
| Arginine | 4.07 ± 0.23 | 0.80 ± 0.09 | <0.0001 |
| Aspartic acid | 6.09 ± 0.37 | 5.08 ± 0.25 | 0.059 |
| Cysteine | 143 ± 0.09 | 0.50 ± 0.05 | <0.0001 |
| Glutamic acid | 10.3 ± 0.90 | 11.6 ± 0.64 | 0.219 |
| Glycine | 3.52 ± 0.26 | 0.99 ± 0.07 | <0.0001 |
| Histidine | 1.89 ± 0.10 | 1.27 ± 0.09 | 0.001 |
| Isoleucine | 3.70 ± 0.16 | 4.75 ± 0.26 | 0.004 |
| Leucine | 6.51 ± 0.35 | 4.12 ± 0.28 | <0.0001 |
| Lysine | 4.53 ± 0.21 | 3.09 ± 0.17 | <0.0001 |
| Methionine | 1.24 ± 0.06 | 1.28 ± 0.08 | 0.605 |
| Phenylalanine | 0.79 ± 0.09 | 0.74 ± 0.08 | 0.061 |
| Proline | 5.27 ± 0.27 | 591 ± 0.32 | 0.198 |
| Serine | 3.27 ± 0.26 | 3.30 ± 018 | 0.883 |
| Taurine | 0.54 ± 0.08 | 0.25 ± 0.03 | 0.019 |
| Threonine | 3.00 ± 0.10 | 7.12 ± 0.41 | <0.0001 |
| Tryptophan | 1.07 ± 0.07 | 0.57 ± 0.05 | <0.0001 |
| Tyrosine | 4.40 ± 0.17 | 2.63 ± 0.21 | <0.0001 |
| Valine | 4.50 ± 0.14 | 4.13 ± 0.21 | 0.105 |
| BCAA | 14.72 ± 0.62 | 13.00 ± 0.72 | 0.034 |

[1]Values are means ± SEMs; n = 22. BCAA, sum of leucine, isoleucine, and valine.
[2]Represents the difference between the AA and the GMP diets by paired t test.

Physical Examination and Blood Chemistry.

There were no physical concerns detected on exam or expressed by any subject to indicate any negative effect on health status when subjects consumed GMP as the primary protein source for a 4-d period. There were no significant differences among serum concentrations of albumin, prealbumin, or total protein as indicators of protein status or creatinine as an indicator of renal status measured on the last day of the AA diet (day 4) compared with the GMP diet (day 8; Table 13). However, BUN as an indicator of hepatic ureagenesis was significantly lower with ingestion of the GMP diet on both day 7 and day 8 than with the AA diet on day 4 (see FIG. 6). Plasma concentration of IGF-I was not significantly different with the AA and GMP diets, which suggests adequate protein nutrition in both diets. Plasma insulin concentration was higher and marginally significant with the GMP diet compared with the AA diet (P=0.053), and serum glucose concentration was not significantly different. Serum carbon dioxide content, which is primarily bicarbonate, was significantly higher with the GMP diet compared with the AA diet, which is consistent with a lower systemic acid content. The mean concentrations of other standard chemistries, including electrolytes and liver function tests, remained within the normal range with both diets (data not shown). The exception was elevated concentrations of various liver function tests (alanine aminotransferase and γ-glutamyltranspeptidase) measured in subject 2, who was on anticonvulsant medications for his seizure disorder. However, further increases in these liver function tests were not detected with ingestion of the GMP diet compared with the elevations measured at admission to the study.

TABLE 13

Effect of amino acid (AA) and glycomacropeptide (GMP) diets on postprandial indexes of protein and glucose metabolism[1]

| Test | AA diet | GMP diet | P value[2] |
|---|---|---|---|
| Blood urea nitrogen (mmol/L) | 4.2 ± 0.3 | 3.4 ± 0.2 | 0.02 |
| Creatinine (itmol/L) | 73 ± 5.5 | 73 ± 4.6 | 1.00 |
| Total protein (g/L) | 68 ± 1.4 | 67 ± 1.4 | 0.27 |
| Albumin (g/L) | 44 ± 0.9 | 44 ± 0.8 | 0.84 |
| Prealbumin (g/L) | 317 ± 7.5 | 310 ± 7.3 | 0.22 |
| Insulin-like growth factor I (nmol/L) | 13.5 ± 1.3 | 13.7 ± 1.5 | 0.14 |
| Insulin (pmol/L) | 84 ± 22 | 116 ± 34 | 0.05 |
| Glucose (mmol/L) | 4.5 ± 0.1 | 4.8 ± 0.1 | 0.14 |
| $CO_2$ content (mmol/L) | 26 ± 0.6 | 28 ± 0.6 | 0.01 |

[1]Values are means ± SEMs; n = 11, except total protein and insulin for which n = 10; all values are within normal range. Values are for serum except those for insulin-like growth factor I and insulin, which used plasma.
[2]Difference between the last day of the AA diet (day 4) and the GMP diet (day 8) by paired t test, pairing on subject.

Plasma AA Concentrations.

Figure 6:
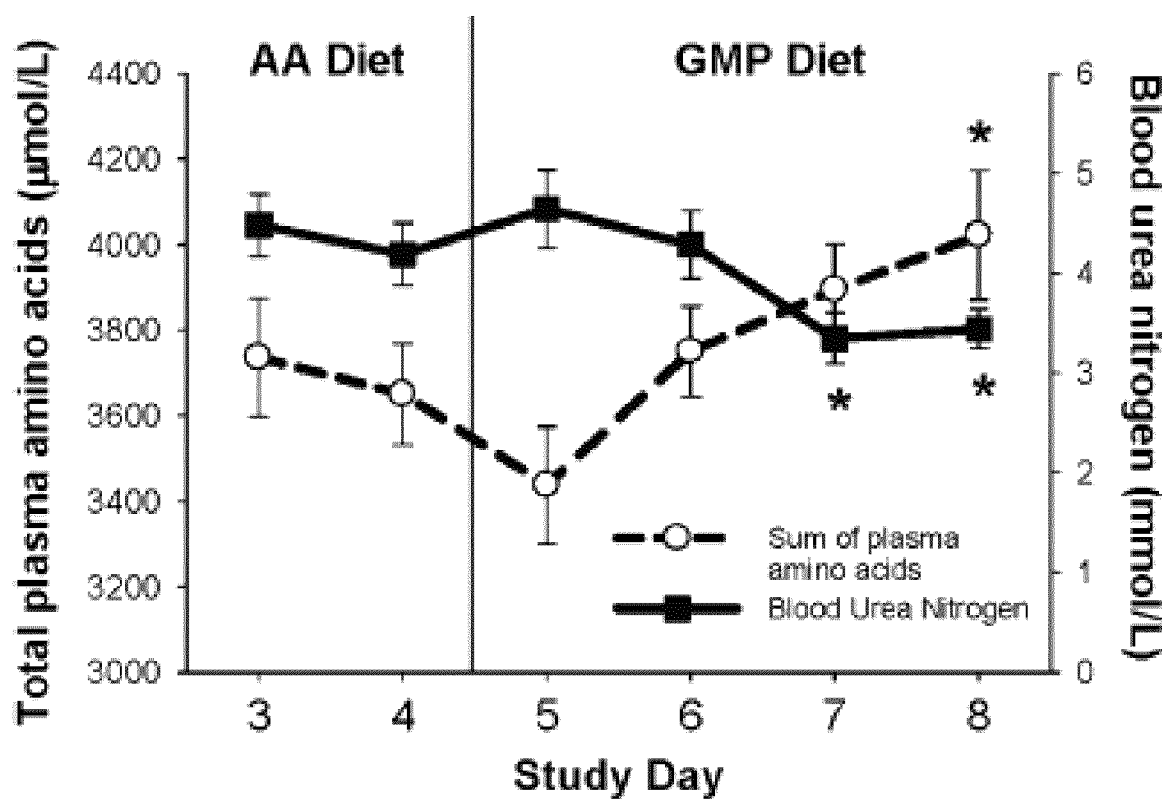
FIG. 6 shows the concentration of total amino acids (AAs) and blood urea nitrogen in postprandial plasma with ingestion of the glycomacropeptide (GMP) or the AA diet. Plasma was obtained 2.5 h after eating breakfast; n=11 with the exception of blood urea nitrogen on study days 5 and 6 for which n=6. Total plasma AAs indicate the sum of all AAs measured in plasma. Values are means±SEMs. Total plasma AAs increased and blood urea nitrogen decreased with ingestion of the GMP diet when compared with day 4 of the AA diet. There was a significant effect of time in the repeated-measures ANOVA. *Significantly different from the AA diet on day 4, P<0.05 (paired t test, pairing on subject).

The concentration of total AAs in plasma was significantly greater, and the concentration of BUN was significantly lower, with the GMP diet compared with the AA diet when measured 2.5 h after eating breakfast (see FIG. 6). This is consistent with slower absorption of AAs from an intact source of protein compared with synthetic AAs and higher insulin concentrations with ingestion of GMP.

Phenylalanine and Tyrosine.

Figure 7:
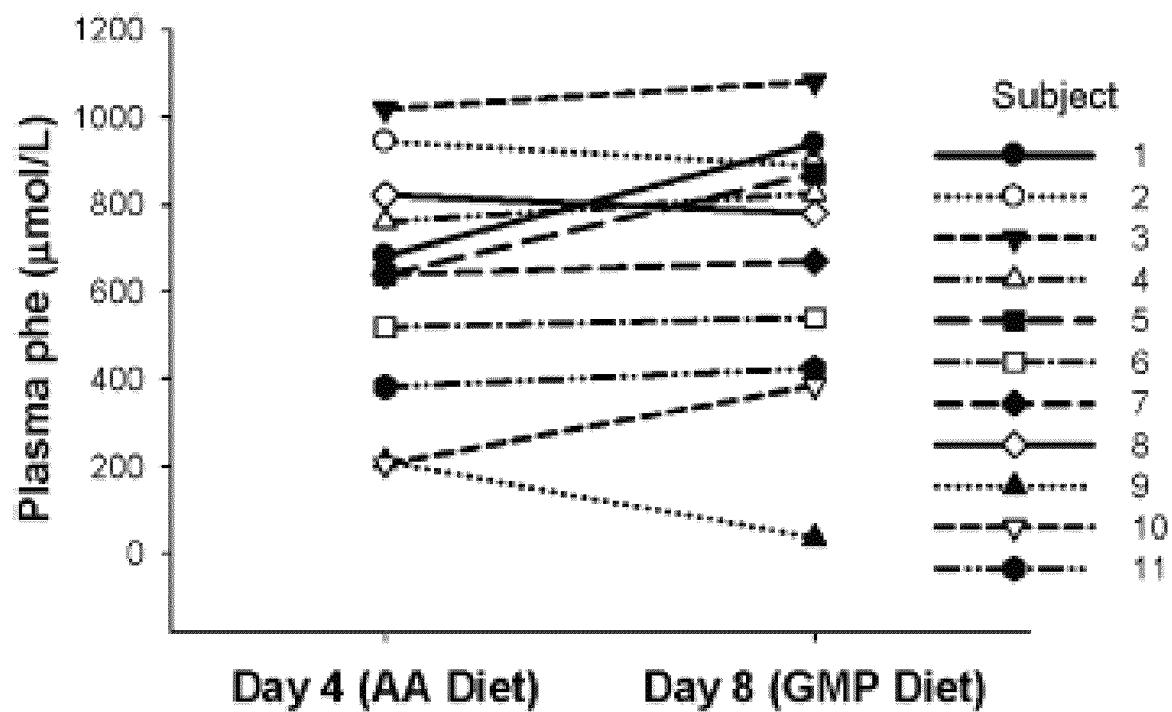
FIG. 7 shows concentrations of phenylalanine in plasma of individual subjects with phenylketonuria (n=11) after consuming the amino acid (AA) diet or the glycomacropeptide (GMP) diet for 4 d. Blood was obtained 2.5 h after eating breakfast, and plasma was isolated for analysis of the complete AA profile. Subjects showed a range of plasma phenylalanine concentrations after consuming the AA diet or the GMP diet for 4 d. There was no significant difference in the concentration of phenylalanine in plasma when the last day of the AA diet (day 4) was compared with the last day of the GMP diet (day 8); P=0.173 by paired t test, pairing on subject. Group mean±SEM was 619±82 μmol/L (AA diet) and 676±92 μmol/L (GMP diet). The mean change in the concentration of phenylalanine in plasma was 57±52 μmol/L. phe, phenylalanine.

There was no significant difference (P=0.173) in the mean postprandial concentration of phenylalanine in plasma with ingestion of the AA diet (day 4) compared with the GMP diet (day 8; FIG. 7). The mean change in the concentration of phenylalanine in plasma was 57±52 μmol phenylalanine/L. Among individual subjects, the response of plasma phenylalanine concentration to ingestion of the GMP diet was heterogeneous, ranging from a decrease of 175 μmol phenylalanine/L to an increase of 257 μmol phenylalanine/L. Overall, there was no consistent association between a change in the concentration of phe in plasma with ingestion of the AA diet compared with the GMP diet and sex, genotype, and age.

Figure 8:
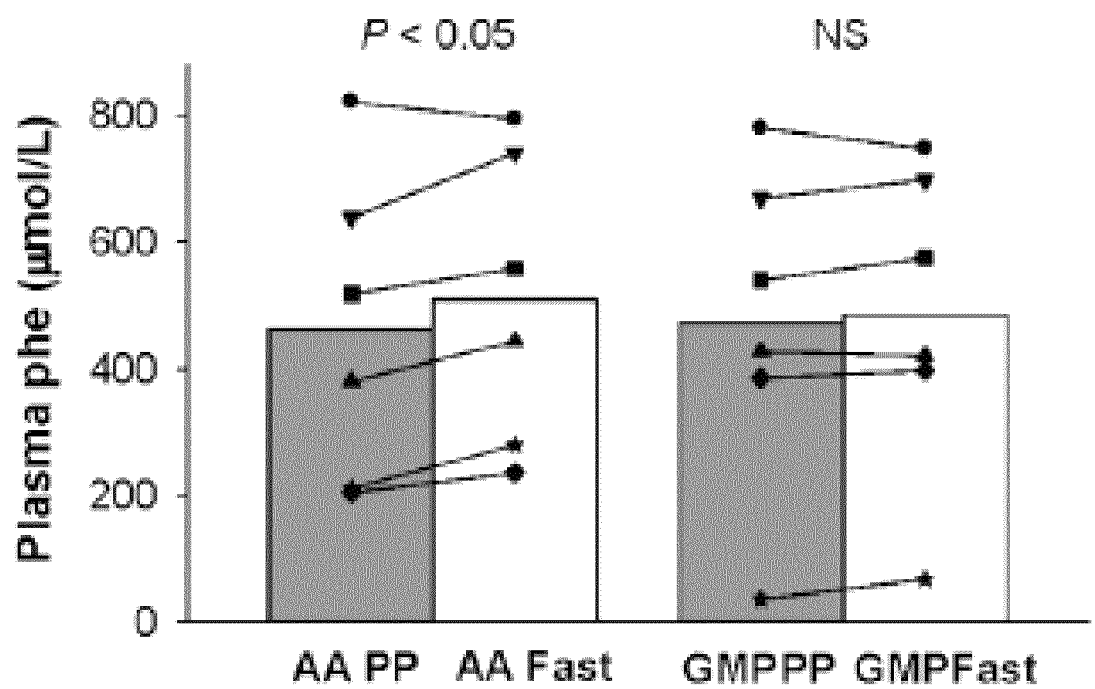
FIG. 8 shows the concentration of phenylalanine in postprandial (PP; 2.5 h after eating breakfast) compared with fasting (fast, overnight fast) plasma in subjects with phenylketonuria fed glycomacropeptide (GMP) compared with the amino acid (AA) diet for 4 d. Group means and the response of individual subjects are shown; n=6 (day 4 compared with day 8). There was no significant change in plasma phenylalanine concentration comparing fasting with PP concentrations when consuming the GMP diet (P=0.349); however, the AA diet showed a significant increase in plasma phenylalanine (P=0.048) by paired t test, pairing on subject. phe, phenylalanine.

Concentrations of phenylalanine in both fasting and postprandial plasma were available on day 4 (AA diet) and on day 8 (GMP diet) for a subset of 6 adult subjects. The postprandial response to the GMP diet was not significantly different with this subset (n=6) than with the first 5 subjects. Ingestion of the AA diet for 4 d resulted in a significant 10% increase in the concentration of phenylalanine in plasma obtained after an overnight fast compared with the concentration of phenylalanine in postprandial plasma obtained 2.5 h after eating breakfast (P=0.048; see FIG. 8). In contrast, ingestion of the GMP diet for 4 d resulted in no significant change in the concentration of phenylalanine in plasma when comparing plasma obtained in a fasting state to plasma obtained in a postprandial state.

Tyrosine is an important AA in the PKU diet because it is indispensable and a precursor of adrenaline, norepinephrine, melanin, and thyroxine. Concentrations of tyrosine in plasma obtained in the postprandial or fasting samples were not significantly different with ingestion of the GMP or AA diets (see Table 14). Concentrations of tyrosine in plasma after an overnight fast were decreased compared with postprandial concentrations with ingestion of both the GMP and the AA diet; however, the GMP diet resulted in a mean fasting tyrosine concentration that was below the normal range.

Additional AAs.

Figure 9:
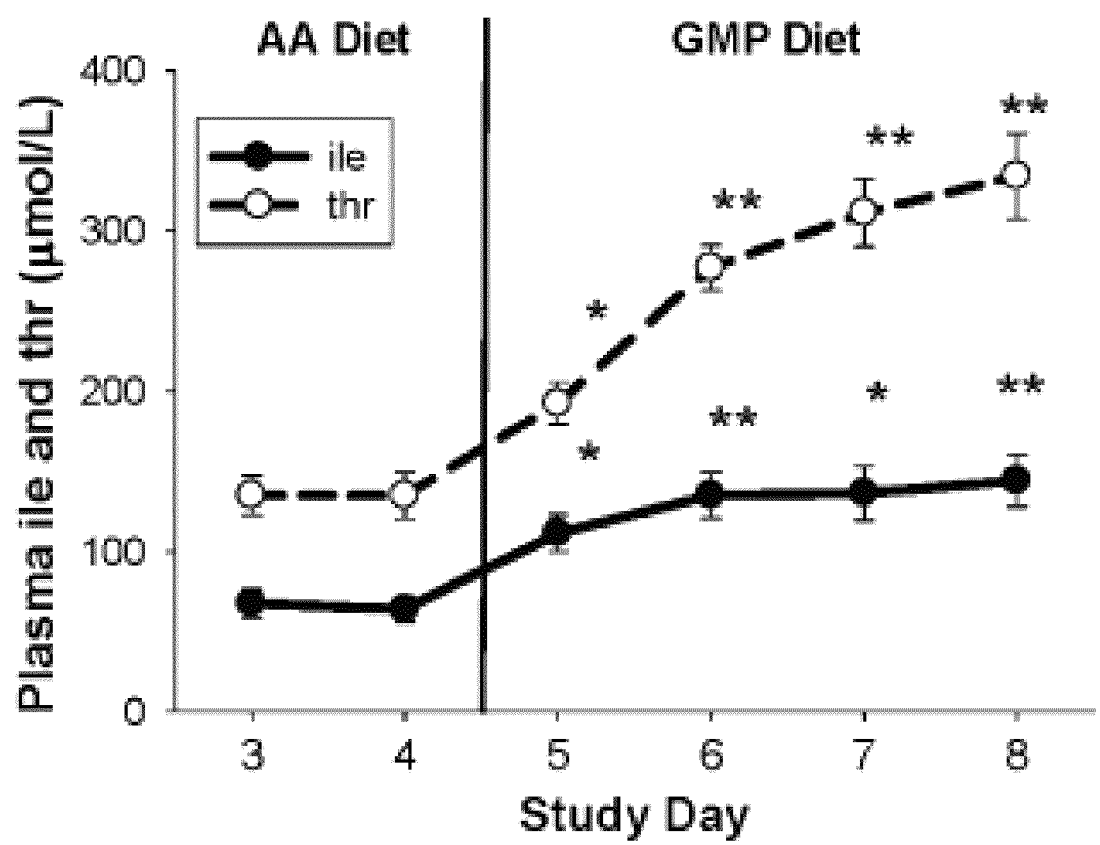
FIG. 9 shows the concentrations of threonine and isoleucine in postprandial plasma after consuming the glycomacropeptide (GMP) diet for 4 d (days 5-8). Values are mean±SEM; n=11, of plasma obtained 2.5 h after breakfast. For study days 3 and 4, all subjects consumed an amino acid (AA) diet; on days 5-8, all AA formula was replaced with GMP food products. There was a significant effect of time in the repeated-measures ANOVA. *Significantly different from the last day of the AA diet (day 4), P<0.05 (paired t test, pairing on subject). **Significantly different from the last day of the AA diet (day 4), P<0.0001. There was no further significant increase in plasma concentration of isoleucine and threonine after days 5 and 7, respectively. ile, isoleucine; thr, threonine.

The most dramatic change in the profile of AAs in plasma with ingestion of the GMP compared with the AA diet was the 2.25- to 2.47-fold increase in postprandial concentrations of the nontoxic LNAA isoleucine and threonine, which places these values above the normal clinical range (see Table 14). A significant increase in plasma concentration of isoleucine and threonine with the GMP diet occurred within 24 h of ingesting the GMP diet and was consistent with the high concentrations of these AAs in GMP (See FIG. 9). However, there was no further significant increase in plasma concentration of isoleucine and threonine after days 5 and 7, respectively. The concentration of isoleucine was not different in plasma obtained after an overnight fast, whereas the concentration of threonine in fasting plasma remained ~2-fold greater with ingestion of the GMP compared with the AA diet.

Consistent with the AA profile of the GMP and AA dietary composites, there were significantly lower postprandial concentrations of ornithine and tryptophan in plasma and significantly higher concentrations of isoleucine and threonine in plasma with consumption of the GMP compared with the AA diet. After an overnight fast, plasma concentration of arginine was significantly lower and concentration of threonine was significantly higher with the GMP compared with the AA diet (see Table 14).

TABLE 14

Effect of amino acid (AA) and glycomacropeptide (GMP) diets on fasting and postprandial (PP) concentrations of AAs in plasma[1]

| | AA diet | | | GMP diet | | | Response to diet fasting compared with PP P value[4] |
|---|---|---|---|---|---|---|---|
| AA | PP[2] | Fasting[2] μmol/L | P value[3] | PP[2] | Fasting[2] mol/L | P value' | |
| Alanine | 455 ± 52 | 356 ± 25 | 0.029 | 514 ± 45 | 401 ± 50 | 0.001 | 0.743 |
| Arginine | 62 ± 14 | 57 ± 5 | 0.694 | 47 ± 5 | 47 ± 6 | 0.845 | 0.551 |
| Citrulline | 37 ± 4 | 26 ± 5 | 0.138 | 23 ± 3 | 26 ± 4 | 0.084 | 0.063 |

TABLE 14-continued

Effect of amino acid (AA) and glycomacropeptide (GMP) diets on fasting and postprandial (PP) concentrations of AAs in plasma[1]

| | AA diet | | | GMP diet | | | Response to diet fasting |
|---|---|---|---|---|---|---|---|
| AA | PP[2] µmol/L | Fasting[2] µmol/L | P value[3] | PP[2] mol/L | Fasting[2] mol/L | P value' | compared with PP P value[4] |
| Cystine | 43 ± 1 | 43 ± 2 | 0.899 | 37 ± 2 | 41 ± 3 | 0.019 | 0.062 |
| Glutamic acid | 40 ± 8 | 50 ± 10 | 0.207 | 43 ± 10 | 49 ± 9 | 0.556 | 0.692 |
| Glutamine | 635 ± 29 | 628 ± 15 | 0.747 | 659 ± 33 | 623 ± 28 | 0.025 | 0.095 |
| Glycine | 415 ± 62 | 399 ± 55 | 0.473 | 346 ± 40 | 371 ± 47 | 0.099 | 0.112 |
| Histidine | 85 ± 9 | 78 ± 5 | 0.206 | 82 ± 6 | 75 ± 4 | 0.066 | 0.681 |
| Isoleucine | 57 ± 6 | 49 ± 4 | 0.352 | 119 ± 15 | 54 ± 5 | 0.015 | 0.004 |
| Leucine | 120 ± 20 | 96 ± 3 | 0.313 | 86 ± 11 | 83 ± 4 | 0.823 | 0.264 |
| Lysine | 210 ± 19 | 181 ± 9 | 0.062 | 191 ± 24 | 171 ± 16 | 0.138 | 0.311 |
| Methionine | 24 ± 2 | 24 ± 1 | 0.832 | 31 ± 4 | 25 ± 3 | 0.150 | 0.144 |
| Ornithine | 74 ± 7 | 60 ± 8 | 0.004 | 50 ± 4 | 62 ± 18 | 0.460 | 0.129 |
| Phenylalanine | 462 ± 100 | 508 ± 95 | 0.048 | 472 ± 106 | 483 ± 101 | 0.349 | 0.037 |
| Proline | 200 ± 15 | 144 ± 12 | 0.001 | 234 ± 37 | 160 ± 20 | 0.012 | 0.322 |
| Serine | 131 ± 21 | 122 ± 16 | 0.123 | 127 ± 14 | 120 ± 11 | 0.517 | 0.821 |
| Taurine | 73 ± 19 | 82 ± 18 | 0.154 | 73 ± 13 | 63 ± 11 | 0.145 | 0.027 |
| Threonine | 158 ± 22 | 135 ± 17 | 0.013 | 354 ± 44 | 265 ± 29 | 0.030 | 0.064 |
| Tryptophan | 48 ± 5 | 44 ± 3 | 0.269 | 34 ± 3 | 42 ± 2 | 0.048 | 0.006 |
| Tyrosine | 81 ± 8 | 38 ± 3 | 0.001 | 56 ± 10 | 29 ± 3 | 0.027 | 0.155 |
| Valine | 240 ± 9 | 194 ± 13 | 0.015 | 241 ± 21 | 187 ± 5 | 0.048 | 0.521 |
| BCAA | 417 ± 28 | 347 ± 14 | 0.084 | 445 ± 45 | 324 ± 8 | 0.048 | 0.062 |

[1]Values are means ± SEMs; n = 6, except for cystine for which n = 5. BCAA, sum of leucine, isoleucine, and valine.
[2]PP plasma concentrations of ornithine (P = 0.019) and tryptophan (P = 0.003) were significantly lower, but within the normal range, and isoleucine (P = 0.003) and threonine (P = 0.004) were significantly higher with ingestion of the GMP diet than with the AA diet and above the normal range. The only significant differences in fasting AA concentrations were a decrease in arginine (P = 0.008) and an increase in threonine (P = 0.001) with ingestion of the GMP diet compared with the AA diet.
[3]There was a significant effect of time in the repeated-measures ANOVA. Statistical analysis by paired t test, pairing on subject, is from data collected on the last day of the AA diet (day 4) and the last day of the GMP diet (day 8).
[4]The response to a diet is calculated first by finding the difference between fasting and PP AA concentrations for each subject on the AA diet and on the GMP diet and then by comparing the differences by paired t test, pairing on subject.

This is the first clinical trial to investigate the efficacy of substituting intact protein from GMP food products for synthetic AA formulas that are currently required for nutritional management of PKU. No adverse health problems were found, and blood chemistries remained normal when subjects with PKU consumed GMP as their primary protein source for 4 d in this controlled metabolic diet study (Table 13). Furthermore, the GMP products were preferred by the subjects, which confirms the results of blind taste tests comparing GMP to AA products in those with PKU (See Example 2). Thus, foods and beverages made with GMP are both safe and highly acceptable for use in the phenylalanine-restricted diet for PKU.

Over a period of 4 d, there was no significant change in plasma phenylalanine concentrations with ingestion of GMP products compared with the AA formula (FIG. 7). GMP, as an intact protein source, may delay absorption of AAs and improve utilization of phenylalanine and other AAs for protein synthesis when compared with a synthetic AA source. In this study, the AA diet showed a significantly higher mean fasting phenylalanine concentration compared with the postprandial phenylalanine concentration (FIG. 8), whereas there was no significant difference in fasting and postprandial phenylalanine concentrations apparent with the GMP diet (Table 14). This suggests that the GMP diet induced less variation and potentially lower mean concentrations of phenylalanine in plasma over a 24-h period. This is consistent with increased protein retention and decreased oxidation of AAs in association with a slower rate of absorption of AAs when the dietary protein source is an intact protein, such as GMP, as compared with a free AA source, such as AA formula.

Evidence of improved protein retention with the GMP diet was also shown by a lower serum BUN and higher plasma insulin and total AA concentrations when measured 2.5 h after eating a breakfast containing GMP compared with one containing AAs (Table 13, FIG. 6). Urea is produced linearly in response to plasma AA concentrations, and control of nitrogen balance is primarily regulated by urea production. BUN, as a measure of hepatic utilization of AAs for urea synthesis, would be expected to remain lower with slower splanchnic AA release. Thus, a slower, more gradual and sustained elevation in plasma AA concentration with an intact protein source, in conjunction with a lower BUN concentration, suggests that fewer AAs are degraded for urea production and instead are retained for protein synthesis when GMP is substituted for synthetic AAs as the primary protein source.

Postabsorptive AAs, including isoleucine and threonine (Calbet et al., J Nutr 2002; 132:2174-82), are known to stimulate insulin release with subsequent stimulation of protein synthesis and inhibition of protein degradation (Schmid, et al., Pancreas 1992; 7:698-704). Because GMP induces a slower and more prolonged release of amino acids, the insulin response and stimulus of net protein synthesis may be potentiated. In addition, whey protein has been shown to increase insulin concentration to a greater extent than other milk protein fractions or other intact protein sources (Nilsson et al., Am J Clin Nutr 2004; 80:1246-53). Thus, the ability of GMP to slow AA catabolism and ureagenesis may reflect increased postprandial concentrations of threonine and isoleucine acting as insulin secretagogues as well as delayed absorption of AAs.

For this study, GMP was supplemented with the following 5 limiting AAs on the basis of the 2002 DRI recommendations: histidine, leucine, methionine, tryptophan, and tyrosine. Plasma concentrations of histidine, leucine, and tryptophan remained within the normal range, which suggests adequate supplementation of these AAs in the GMP diet (Table 14). In contrast, plasma concentration of tyrosine was below the normal range when measured in the fasting state (Table 14), which suggests that additional tyrosine supplementation may be required in GMP. Indeed, additional tyrosine from a supplement providing 1000 mg/d allowed for plasma tyrosine concentrations to remain within the normal range for one subject who consumed GMP as his primary protein source for 10 wk (see Example 3). In summary, our data suggest that GMP must be supplemented with arginine, histidine, leucine, tryptophan, and tyrosine to provide a complete source of dietary protein in the PKU diet.

Lifelong adherence to the PKU diet is very difficult, often resulting in poor compliance and the neuropsychological consequences of hyperphenylalaninemia. This research shows a new, improved paradigm for the PKU diet through the use of palatable foods and beverages made with the intact, low-phenylalanine protein GMP instead of synthetic AAs. When supplemented with limiting indispensable AAs, GMP appears to be a safe and acceptable alternative to synthetic AAs as the primary protein source for nutritional management of PKU. As an intact protein, GMP delays absorption of AAs and improves protein retention and phenylalanine utilization compared with a diet that provides the majority of nitrogen from AAs.

Example 5

Increasing GMP Purity and Using a Mass Balance Calculation for Amino Acid Supplementation of GMP-Based Foods This Example illustrates methods for increasing the purity of GMP used in making GMP-based foods. In addition, the Example illustrates the use of a mass balance calculation for determining the extent of indispensable amino acid supplementation of GMP-based foods. Introduction Daily recommended intakes (DRI) of indispensable amino acids for individuals older than 1 y have been established based on the nitrogen content of foods (see Table 15).

TABLE 15

Daily recommended intake (DRI) of indispensable amino acids for children ≥1 y of age and all other age groups. (Adapted from Inst. of Medicine 2005, Dietary Reference Intakes for Energy, Carbohydrate, Fiber, Fat, Fatty acids, Cholesterol, Protein, and Amino Acids, Washington, DC: Natl. Academies Press).

| Amino acid | DRI mg/g N | DRI mg/g PE[a] |
|---|---|---|
| His | 114 | 18 |
| Ile | 156 | 25 |
| Leu | 341 | 55 |
| Lys | 320 | 51 |
| Met + Cys | 156 | 25 |
| Phe + Tyr[b] | 291 | 47 |
| Thr | 170 | 27 |
| Trp | 43 | 7 |
| Val | 199 | 32 |

[a]PE = N × 6.25.
[b]Only Tyr was used to supplement GMP.

DRI values for amino acids are often reported on a protein equivalent (PE) basis defined as total nitrogen (N) times a conversion factor of 6.25 (Inst. of Medicine 2005). Most proteins contain about 16% nitrogen and a conversion factor of 6.25 (100 g protein/16 g N=6.25 g protein/g N) is appropriate (Nielsen S S 2003, Food Analysis, 3rd ed. New York: Kluwer Academic/Plenum Publishers). However, the nitrogen to protein conversion factor varies among foods. For example, the nitrogen to protein conversion factor used for most dairy proteins is 6.38 (Id.). GMP is a heterogeneous peptide, some GMP molecules are glycosylated and others are not. Because of this, the conversion factor for a GMP molecule can range from 6.70 to 9.55 depending on the extent of glycosylation present (Dziuba and Minkiewicz 1996, Int Dairy J 6(11-2):1017-44). Ambiguity in the definition of protein mass is illustrated by one manufacturer of GMP that uses a conversion factor of 6.47 to report protein and 7.07 to report GMP (Davisco Foods Intl.).

The actual protein content of foods is difficult to measure when the precise nitrogen to protein conversion factors are unknown. Proteins may contain nonprotein nitrogen, or basic amino acids, which are higher in nitrogen than other amino acids. For GMP to provide the recommended levels of indispensable amino acids in the diet, the protein composition of foods consumed must be known using an unambiguous definition of what constitutes 1 g of protein. In this Example, a conversion factor of 6.25 was used to comply with the Inst of Medicine (Inst. of Medicine. 2005) definition of protein used to establish the DRI for indispensable amino acids for individuals older than 1 y (see Table 15).

Current large-scale technologies to isolate GMP from whey use ion exchange chromatography or ultrafiltration. GMP has an isoelectric point (pI) below 3.8, whereas other major whey proteins have pI values above 4.3. This physicochemical difference between GMP and other whey proteins is commonly used in isolation processes to separate GMP from whey. Commercially available GMP isolated by ion exchange chromatography is typically not pure enough for PKU foods because it contains too much Phe from residual whey proteins (i.e. 5 mg Phe/g product, manufacturer literature, Davisco Foods Intl., Eden Prairie, Minn., U.S.A.). Traditional amino acid formula is free of Phe, which allows an individual with PKU to consume natural foods that contain Phe to meet their daily allowance. In order for GMP to be a feasible protein replacement for amino acid formula in the PKU diet, improved processes are needed to increase GMP purity and reduce Phe content.

To conduct a human clinical trial to test the safety and feasibility of GMP foods for individuals with PKU, a pilot scale process was developed to prepare highly purified GMP sufficient to feed 15 individuals for 4 d. Food-grade materials and food-approved facilities were utilized to manufacture 5 kg of purified GMP using the following unit operations in sequence (1) cation exchange chromatography, (2) ultrafiltration and diafiltration (UF/DF), and (3) lyophilization. Furthermore, a mass balance calculation was developed to provide a clearly defined basis for amino acid supplementation. Purified, supplemented GMP was used to prepare GMP foods consumed in the human clinical trial.

Materials and Methods

This section has been divided into 3 subsections: (1) unit operations used to manufacture purified GMP using food-grade materials, (2) mass balance calculations used to determine GMP recovery and the mass of amino acids for supplementation of purified GMP, and (3) preparation and analysis of a GMP food consumed in the clinical trial and 1 patient response.

GMP Purification Process

Contaminating whey proteins in crude GMP (BioPure GMP, Davisco Foods Intl.) were trapped by adsorption onto a cation exchange resin and GMP was collected in the flow-through fraction. Ultrafiltration/diafiltration (UF/DF) was used to concentrate the GMP and wash out peptides, salts, and nonprotein nitrogen. Lyophilization was used to dry the purified, concentrated GMP.

Cation Exchange Chromatography.

A 20-cm-dia chromatography column (INdEX, GE Healthcare, Piscataway, N.J., U.S.A.) was packed with SP Sepharose Big Beads (GE Healthcare). The column volume (CV) was 5.34 L, and the bed height was 18 cm.

Feed solution (75 g/L) was prepared by mixing crude GMP (BioPure GMP, Davisco Foods Intl.) with 10 mM sodium lactate, pH 4, and filtering through a 0.45-μm pore size filter (Sartobran P, Sartorius, Edgewood, N.Y., U.S.A.). Equilibration and elution buffers were food-grade 50 mM sodium lactate, pH 4, and 10 mM NaOH, pH 12, respectively. Equilibration buffer and GMP feed solution were held at 4° C. to inhibit microbial growth. Elution buffer was held at 22° C. Flow rate was 950 mL/min. Each cation exchange cycle consisted of 4 steps: (1) the column was brought to pH 4 using 2 CV of equilibration buffer, (2) 0.5 CV of feed solution was applied to the column, (3) the column was rinsed with equilibration buffer wherein the first 0.3 CV of effluent was discarded (column dead volume) and the next 2 CV of purified GMP was collected, and (4) bound proteins were desorbed from the column using 2.5 CV of elution buffer. Each of the 5 campaigns consisted of 9 to 11 consecutive cycles. About 100 L of dilute GMP protein solution were generated from each campaign. The cation exchange column was cleaned by pumping in 0.2 M NaOH, holding for 1 h, and then storing the column in 10 mM NaOH.

Ultrafiltration and Diafiltration.

GMP effluent from the cation exchanger was adjusted to pH 7 by addition of 1 M NaOH, and concentrated at 60° C. using a hollow fiber ultrafiltration membrane (3 kDa, 3.3 m$^2$, UFP-3-C-55, GE Healthcare). The applied pressure was 1.4 bar. GMP solution was concentrated from 100 to 10 L, and then 20 L of distilled water added and the solution was concentrated again to 10 L. The concentrate was filtered using a 0.45-μm pore size filter (Sartorius) into a sanitized container and stored at 4° C. Before and after each use, the UF membrane was cleaned for 30 min using 0.2 M NaOH containing 100 ppm NaOCl (bleach) at 50° C. The UF membrane was stored in 10 ppm NaOCl.

Lyophilization.

Concentrated, sterile-filtered GMP solution was frozen into a thin layer onto 1.2 or 2 L glass lyophilization flasks and dried for 48 h (Lyphlock6, Labconco, Kansas City, Mo., U.S.A.). GMP powder was recovered, weighed, and a portion used for analysis.

Composition Analysis.

Crude protein analysis (CP) and complete amino acid profiling (AAP) were conducted by the Experiment Station Chemical Laboratories (Univ. of Missouri-Columbia, Columbia, Mo., U.S.A.). AOAC official method 982.30 was used for AAP, and AOAC official method 990.03 was used for CP ([AOAC] Assn. of Official Analytical Chemists, Intl. 2005. Official methods of analysis of official analytical chemists. 18th ed. Gaithersburg, Md.: AOAC). Results were reported as gram per 100 g dry weight of purified GMP. A conversion factor of 6.25 times total nitrogen was used to express the results on a PE basis. Duplicate analyses were performed for all samples.

Mass Balance Calculations

Mass balance calculations are presented to describe (1) the calculations used to determine GMP recovery from the manufacturing process, (2) the lysine basis used for amino acid supplementation, and (3) the method used to determine the required amount of supplemental amino acids.

GMP recovery.

Recovery was calculated on a PE basis. Grams of PE in the feed solution ($M_{PE,feed}$) were determined by multiplying the GMP feed concentration (75 g/L) by the grams of PE per gram of powder (from CP analysis) and then multiplying by the total volume of feed solution processed. The total grams PE recovered ($M_{PE,recovered}$) was obtained by multiplying the mass of purified GMP powder times the grams of PE per gram of purified GMP (from CP analysis). GMP recovery (%) was equal to $M_{PE,recovered}/M_{PE,feed} \times 100$.

Lysine Basis for Amino Acid Supplementation.

Amino acid supplementation is required for purified GMP to meet the nutritional targets set by the DRI and the clinical trial. Lysine (Lys) was chosen as the basis for the mass balance supplementation calculation, because it was closest to the target value (see Table 16, column C compared with D). Only 5 indispensable amino acids for PKU required supplementation: His, Leu, Met, Trp, and Tyr. Dispensable and conditionally indispensable amino acids were not supplemented.

Free amino acids are absorbed and degraded faster than those provided by intact proteins. Therefore, the target amino acid composition for the clinical trial was set above the DRI levels. Targets for His, Leu, Met, and Trp were set at 130% of the DRI level. Tyr was supplemented at 150% of the DRI level, because amino acid formulas are often enriched with high levels of Tyr. In the tables and figures pertaining to the supplementation of GMP to meet the DRI, Phe and Tyr are listed together, as are Met and Cys, because Tyr and Cys are conditionally dispensable amino acids that can be synthesized from Phe and Met, respectively. However, in a PKU patient, Tyr cannot be synthesized from Phe.

TABLE 16

Supplemental amino acid (AA) calculation method.

| | A | B<br>GMP | C = A/B | D<br>Clinical | E = D − C<br>Ignores PE of added AA (not<br>included in denominator) | | F = C + E | G<br>Includes PE of added AA<br>(included in denominator) | H = F × B/G |
|---|---|---|---|---|---|---|---|---|---|
| Amino<br>acid | GMP AA<br>composition[a]<br>mg/g purified<br>GMP | PE[a] g<br>PE/g<br>purified<br>GMP | GMP<br>composition<br>on PE basis<br>mg/g PE | trial<br>target<br>mg/g<br>PE | AA<br>supplementation<br>required mg/g<br>PE | Supplemented<br>composition<br>mg/g PE | | Corrected<br>PE g PE/g<br>purified<br>GMP | Corrected<br>supplemented<br>composition<br>mg/g PE |
| His | 1.15 ± 0.07 | — | 1.5 ± 0.1 | 23 | 22 | | 23.5 ± 0.1[a] | — | 21 ± 2[a] |
| Ile | 75.5 ± 4.2 | — | 102 ± 2 | 25 | 0 | | 102 ± 2[a] | — | 90 ± 10[a] |
| Leu | 17 ± 1 | — | 23 ± 0.2 | 72 | 49 | | 72 ± 0.2[a] | — | 66 ± 7[a] |
| Lys | 44 ± 3 | — | 60.1 ± 0.8 | 51 | 0 | | 60.1 ± 0.8[a] | — | 55 ± 6[a] |
| Met +<br>Cys | 15 ± 2 | — | 20.5 ± 0.5 | 33 | 12 | | 32.5 ± 0.8[a] | — | 30 ± 3[a] |
| Phe + | 3 ± 1 | — | 2.6 ± 0.6 | 71 | 68 | | 70.6 ± 0.6[a] | — | 64 ± 6[a] |

TABLE 16-continued

Supplemental amino acid (AA) calculation method.

| Amino acid | A<br>GMP AA composition[a] mg/g purified GMP | B<br>GMP<br>PE[a] g PE/g purified GMP | C = A/B<br>GMP composition on PE basis mg/g PE | D<br>Clinical trial target mg/g PE | E = D − C<br>Ignores PE of added AA (not included in denominator) | | F = C + E | G<br>Includes PE of added AA (included in denominator) | H = F × B/G |
|---|---|---|---|---|---|---|---|---|---|
| | | | | | AA supplementation required mg/g PE | Supplemented composition mg/g PE | | Corrected PE g PE/g purified GMP | Corrected supplemented composition mg/g PE |
| Tyr | | | | | | | | | |
| Thr | 120 ± 10 | — | 161 ± 2 | 27 | 0 | 161 ± 2$^a$ | | — | 150 ± 10$^a$ |
| Trp | 0 ± 0 | — | 0 ± 0 | 9 | 9 | 9 ± 0$^a$ | | — | 8 ± 0.8$^a$ |
| Val | 62 ± 3 | — | 85 ± 2 | 32 | 0 | 85 ± 2$^a$ | | — | 78 ± 8$^a$ |
| PE | — | 0.74 ± 0.05 | — | — | — | — | | 0.81 ± 0.06 | — |

[a]Composition obtained by analysis. Values are mean ± SD. Sample size was n = 2.
Same letters in column F and H indicate no significant statistical difference (P > 0.05).

Amino Acid Supplementation Calculations.

A challenge with supplementation is that adding amino acids to the purified GMP changes the amino acid target (mg amino acid/g PE) by changing both the numerator (mg amino acid) and the denominator (g PE). Two methods will be illustrated for the supplementation calculation: one includes the change in the denominator and the other does not. Both methods account for the change in the numerator. The steps used to calculate amino acid supplementation are presented in Table 16 above. The experimental results for AAP were used to obtain the milligram of each amino acid per gram of purified GMP (column A). The experimental results for CP (column B) were divided into column A to obtain the GMP amino acid composition on a PE basis (column C). Conversion to a PE basis (column C) was needed to compare the purified GMP amino acid composition to the clinical trial target values (column D). The amino acid values of purified GMP were subtracted from each of the clinical trial target values to yield the required mass of each supplemented amino acid (column E). By adding the required amino acid values (column E) to the purified GMP amino acid values (column C), the composition of the supplemented GMP was calculated (column F). This method for the supplementation calculation ignored the impact of adding amino acids on the denominator of the amino acid composition (mg/g PE).

To account for the change in the denominator, the increase in the grams of PE per gram of purified GMP due to supplementation must be taken into account (Table 16, columns G and H). To do this, the total nitrogen contribution of the supplemental amino acids needed for 1 g of purified GMP was determined from the molecular formula and multiplied times 6.25 to yield the total grams of PE contributed by the added amino acids. The grams of PE from the supplemented amino acids were added to the grams of PE per 1 g of purified GMP (column B) to yield the corrected grams of PE per gram of purified GMP (column G). The supplemented composition (column F) was multiplied by column B and divided by column G to account for the change in the denominator (column H).

The corrected supplemented GMP composition was not statistically significantly different from the uncorrected composition (Table 16, column H compared with F) (P>0.05). Therefore, the calculation method used to supplement purified GMP in this study assumed that the contribution of added amino acids to the denominator was negligible.

Preparation and Analysis of GMP Foods.

The recipe for GMP strawberry pudding is presented in Table 17. Purified GMP, supplemental amino acids, and non-dairy creamer (Flavorite Non-Dairy Creamer, SuperValu, Eden Prairie, Minn., U.S.A.) contributed amino acids to the GMP strawberry pudding. Amino acid contribution from purified GMP, nondairy creamer, and added amino acids were used to calculate the amino acid composition of the pudding on a PE basis using the method presented previously in Table 16.

TABLE 17

GMP strawberry pudding recipe

| Ingredients | Dry mix percent % (w/w) |
|---|---|
| Purified GMP[a] | 12.94 |
| Supplemented amino acids[a] | |
| His | 0.22 |
| Leu | 0.70 |
| Met | 0.11 |
| Tyr | 0.68 |
| Trp | 0.09 |
| Food ingredients | |
| Nondairy creamer[a] | 39.73 |
| Sucrose | 32.22 |
| Starch | 8.60 |
| Strawberries, dried | 2.13 |
| Citric acid | 1.59 |
| Sodium chloride | 0.57 |
| Strawberry flavor | 0.41 |
| Red color | 0.01 |
| Dry mix total | 100 |

[a]Purified GMP, supplemental amino acids, and nondairy creamer contribute amino acids to final product.

Statistical Analysis.

Statistical analysis was performed using a one-way analysis of variance (ANOVA) (Minitab Statistical Software, Release 13.32, State College, Pa., U.S.A.) to compare the composition of supplemented GMP with and without taking the denominator into account (Table 16). Confidence intervals were constructed to compare the calculated composition of GMP strawberry pudding to the observed composition and the DRI values. A 95% confidence level was used to construct confidence intervals, and statistical significance was declared at $\alpha<0.05$.

Results

The goal of this study was to produce purified GMP with reduced Phe in quantities great enough to supply 15 PKU subjects with GMP foods during their participation in an 8 d clinical trial. Purified GMP required supplementation with indispensable limiting amino acids to provide a nutritionally complete protein source for use in GMP foods. The safety and efficacy of GMP foods as a palatable source of protein for the PKU diet was tested. The following sections discuss how these objectives were met and have been separated into the effect of the pilot plant process on the recovery and Phe content of purified GMP, the mass balance on amino acids in GMP strawberry pudding and comparison of the amino acid composition of the GMP strawberry pudding to the DRI and an amino acid formula, and the effect of the purified, supplemented GMP foods on the plasma amino acid levels of PKU subjects.

Effect of Purification Process on Phe Content and GMP Recovery.

Table 18 contains the Phe content, recovery, and number of cation exchange cycles for each campaign. Phe in crude GMP was reduced 47% by the purification process, from 4.7±0.5 mg/g PE to 2.7±0.4 mg/g PE. Average GMP recovery was 52±4%. The low recovery of GMP was attributed primarily to a portion of GMP that bound to the cation exchange column and was not recovered in the flow-through fraction. The purification process used to increase the purity of commercially available GMP gave consistent, repeatable Phe concentrations, and there were no statistical differences between Phe concentrations in purified GMP produced by the 5 campaigns (P>0.05).

TABLE 18

Phe content of purified and commercially available GMP

| Campaign | Cycles | Phe[a] mg/g PE | GMP recovery % |
|---|---|---|---|
| 1 | 10 | 3.3 ± 0.2 | 51 |
| 2 | 11 | 2.6 ± 0.2 | 55 |
| 3 | 10 | 3 ± 0 | 55 |
| 4 | 9 | 2.2 ± 0.5 | 53 |

TABLE 18-continued

Phe content of purified and commercially available GMP

| Campaign | Cycles | Phe[a] mg/g PE | GMP recovery % |
|---|---|---|---|
| 5 | 9 | 2.7 ± 0.1 | 44 |
| Average purified GMP | — | 2.7 ± 0.4 | 52 ± 4 |
| Commercially available GMP | — | 4.7 ± 0.5 | — |

[a]Composition obtained by analysis. Values are mean ± SD Sample size was n = 2.

GMP transmission through the UF membrane for each campaign is presented in Table 19. Overall, GMP retention by the UF membrane was 96±2%. Although GMP has a molecular weight of about 7 kDa, it has an apparent molecular weight of 45 kDa at pH 4 and above. The pH of GMP solution was increased to 7 for the UF/DF step to minimize GMP transmission through the 3 kDa membrane. This likely explains the high recovery found for the UF step.

TABLE 19

GMP transmission through UF membrane

| GMP Campaign | GMP transmission (%) |
|---|---|
| 1 | 3.4 |
| 2 | 6.8 |
| 3 | 2 |
| 4 | 3.6 |
| 5 | 2 |
| Mean SD (n = 5) | 4 ± 2 |

Comparison of Amino Acid Supplementation Calculations and GMP Food Composition.

The GMP strawberry pudding was analyzed and the composition compared to the calculated amino acid composition (Table 20). Purified GMP (Table 20, column A) was supplemented with amino acids (column B), determined using the mass balance method that ignored the change in denominator due to added amino acids; similarly for the added amino acids from the nondairy creamer (column C). The sum of columns A, B, and C was the calculated composition of the GMP pudding ignoring changes in the denominator (column D).

TABLE 20

Calculated and analyzed amino acid (AA) composition of GMP strawberry pudding

| Amino acid | A Purified GMP[A] mg/g PE GMP | B Added AA from supplemented amino acids[B] mg/g PE GMP | C Added AA from nondairy creamer[A] mg/g PE GMP | D = A + B + C (Added AA not included in denominator) Calculated AA composition[B] mg/g PE GMP | E (Added AA included in denominator) Corrected, calculated AA composition[C] mg/g PE Total | F Analyzed AA composition[A] mg/g PE Total |
|---|---|---|---|---|---|---|
| His | 1.5 ± 0.1 | 22 | 2.9 ± 0.6 | 26.4 ± 0.6[a] | 21 ± 3[a] | 18 ± 3[a] |
| Ile | 102 ± 2 | 0 | 5.6 ± 0.5 | 108 ± 2[a] | 83 ± 7[a,b] | 70 ± 10[b] |
| Leu | 23 ± 0.2 | 69 | 10 ± 1 | 102 ± 1[a] | 81 ± 6[b] | 77 ± 2[b] |
| Lys | 60.1 ± 0.8 | 0 | 6 ± 1 | 66 ± 1[a] | 51 ± 5[a,b] | 47 ± 8[b] |
| Met + Cys | 20.5 ± 0.5 | 11 | 4 ± 1 | 36 ± 1[a] | 28 ± 2[b] | 22 ± 3[b] |
| Phe + Tyr | 2.6 ± 0.6 | 66 | 8.7 ± 0.7 | 70.6 ± 0.9[a] | 63 ± 4[b] | 45 ± 3[c] |
| Thr | 161 ± 2 | 0 | 4.1 ± 0.7 | 165 ± 2[a] | 130 ± 10[a] | 120 ± 30[a] |
| Trp | 0 ± 0 | 9 | 1.7 ± 0.1 | 10.7 ± 0.1[a] | 8.7 ± 0.6[a] | 10 ± 2[a] |
| Val | 85 ± 2 | 0 | 7 ± 1 | 91 ± 3[a] | 70 ± 6[a,b] | 70 ± 10[b] |

[A]Composition obtained by analysis. Values are mean ± SD. Sample size was n = 2.
[B]Calculated without including added amino acids in the denominator (Method of Table 2, column F).
[C]Calculated including added amino acids in the denominator (Method of Table 2, column H).
Same letter between the columns D, E, and F indicates that no difference was detected between means (P > 0.05).
A statistically significant difference was detected between columns E and F for Tyr + Phe at α < 0.05 but not at α < 0.01.

For comparison, the amino acid composition of the GMP strawberry pudding was calculated to include the changes in the denominator (Table 20, column E). Ignoring the contribution to the denominator resulted in a 30% overestimation, on average, of the calculated amino acid composition compared to the observed values (Table 20, column D compared with F). By including the contribution to the denominator, the corrected calculated amino acid composition was not statistically different from the observed composition (P>0.05), except for Tyr (P<0.05) (Table 20, column E compared with F). The observed amino acid composition of the GMP strawberry pudding (column F) met or exceeded all of the DRI target values (Table 15).

Figure 10:
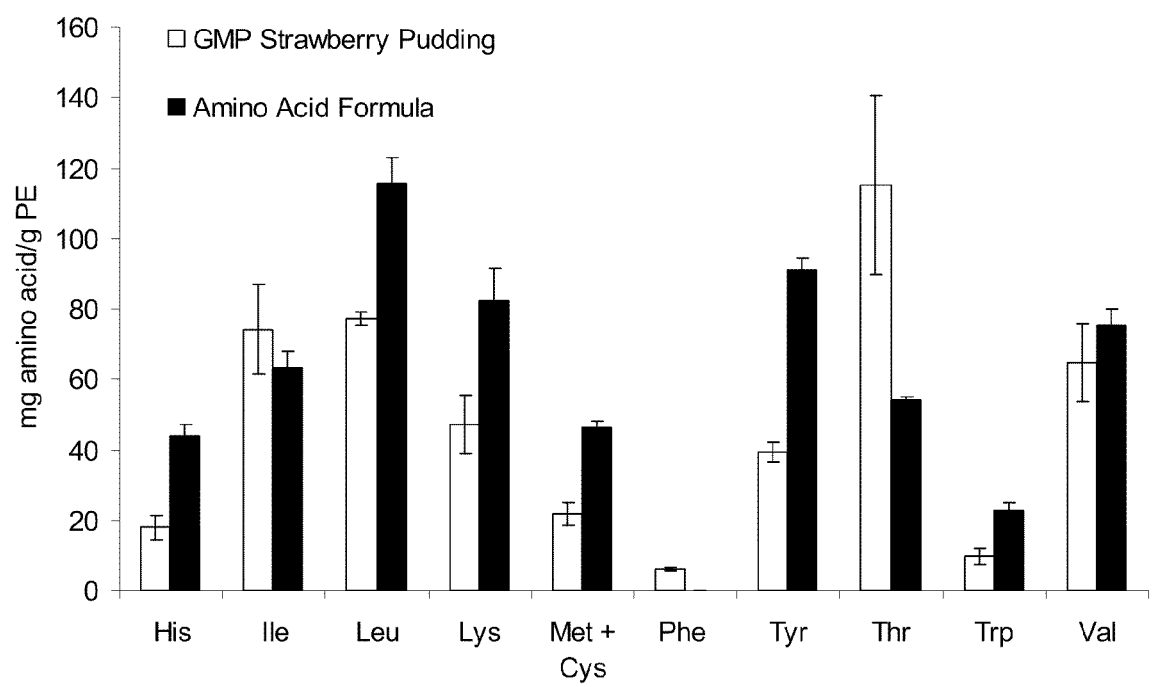
FIG. 10 shows the amino acid profile of GMP strawberry pudding compared to amino acid formula (Phlexy-10 Drink Mix, SHS North America, Rockville, Md., U.S.A.). Values are mean±SD. Sample size was n=2. Same letter above GMP strawberry pudding and amino acid bars indicates that values are not statistically different (P>0.05).

The amino acid composition of GMP strawberry pudding was compared to an amino acid formula (see FIG. 10). The amino acid formula contained significantly more His, Leu, Met+Cys, Tyr, and Trp than the GMP strawberry pudding (P<0.05). However, both amino acid formula and GMP strawberry pudding met or exceeded DRI targets for all indispensable amino acids (P>0.05, Table 15).

Discussion

Manufacture of Purified GMP.

The low overall recovery of GMP (52±4%) was attributed to interactions between GMP and the cation exchange column and resulted in a portion of GMP binding to the column. The binding of GMP to the column was attributed to heterogeneity of GMP. Some GMP molecules were less negatively charged than others at the operating pH of 4 and therefore bound to the cation exchange column. Operating at a higher pH may have minimized GMP binding to the column by increasing the negative charge on GMP. This would also cause a decrease in electrostatic attraction between residual whey proteins and the cation exchange column as the positive charge on these proteins would be decreased. Increasing the operating pH to greater than 4 would have compromised purity. Purity was a priority over recovery in the production of GMP used in the clinical trial.

UF/DF removed low molecular weight solutes and concentrated the GMP prior to the final drying step. UF/DF cannot remove contaminating whey proteins, such as ALA and BLG, because these proteins are too large to permeate a 3 kDa membrane. On the other hand, low molecular weight solutes, such as whey peptides, are small enough to be removed by UF/DF and may contain Phe.

Lyophilization produced a fine white powder with no flavor or odor and dissolved clearly in water (data not shown). However, the disadvantage of this drying method was the long processing time. Each other step in the process could be completed in 1 d, but lyophilization took several days to complete. Despite the intensive time requirement, lyophilization was the most practical choice to dry purified GMP for use in this study. Spray drying was not used because of the potential losses of GMP and limitations of the method when drying small quantities of product. In large-scale manufacture, spray drying would be the method of choice.

Amino Acid Supplementation of Manufactured GMP.

The calculation method used for supplementation of GMP ignored the grams of PE from added amino acids in the denominator, but was easily implemented and resulted in a GMP strawberry pudding that met or exceeded the DRI targets for all indispensable amino acids (Table 20). For GMP alone, ignoring the change to the denominator from added amino acids did not result in a statistically significantly different GMP composition (Table 16, column F compared with H).

Ignoring the change in the denominator from addition of both nondairy creamer and supplemented amino acids resulted in a 30% overestimation of amino acids compared to the observed value and 6 of the 9 amino acids were statistically significantly below the observed value (Table 20, column D compared with F). On the other hand, when the PE contributed by added amino acids were accounted for in the denominator, the corrected calculated values matched the observed values (P>0.05) except for Tyr (P<0.05) (Table 20, column E compared with F). However, Tyr was not statistically significantly different than the observed value at $\alpha$<0.01 (P>0.01). The lower than expected Tyr value was attributed to low purity of the Tyr supplement. Photodegradation of Tyr can occur and could have taken place at some point during the manufacture or storage, which would lead to a lower than expected purity. Although the DRI for Tyr was met in the GMP food, increased Tyr supplementation would provide a higher level of Tyr.

Simplifications were reasonable for the supplementation calculations for GMP alone, due to the negligible impact on amino acid composition and ease of implementation, but were not reasonable to make when performing the mass balance calculations on the GMP food. GMP plus supplemented amino acids made up 15% (w/w) of the GMP pudding, whereas the nondairy creamer made up nearly 40% (w/w) of the pudding, and had a significant impact on the final composition.

Although the nutritional requirement for amino acids is not a static subject, the mass balance calculation method of the present study is generically useful to supplement GMP foods to meet or exceed the nutritional needs of the human diet based on the most recent science.

Example 6

Acceptability of GMP Food of the Invention Compared to AA-Based Formula

In this Example, the inventors conducted sensory studies to compare the acceptability of Bettermilk™, a medical food of the present invention made by Cambrooke Foods, LLC, Ayer, Mass., to Phenex-2™, a conventional amino acid formula for PKU diets, produced by Abbott Nutrition, Columbus, Ohio. Bettermilk contains GMP and supplemental amounts of the amino acids arginine, leucine, tyrosine, tryptophan, and histidine. Both formulas were supplemented with vitamins and minerals to provide nutritionally complete medical foods. The results indicate that GMP Bettermilk is significantly more acceptable in both adult PKU and non-PKU subjects compared with AA-based Phenex-2.

Figure 11:
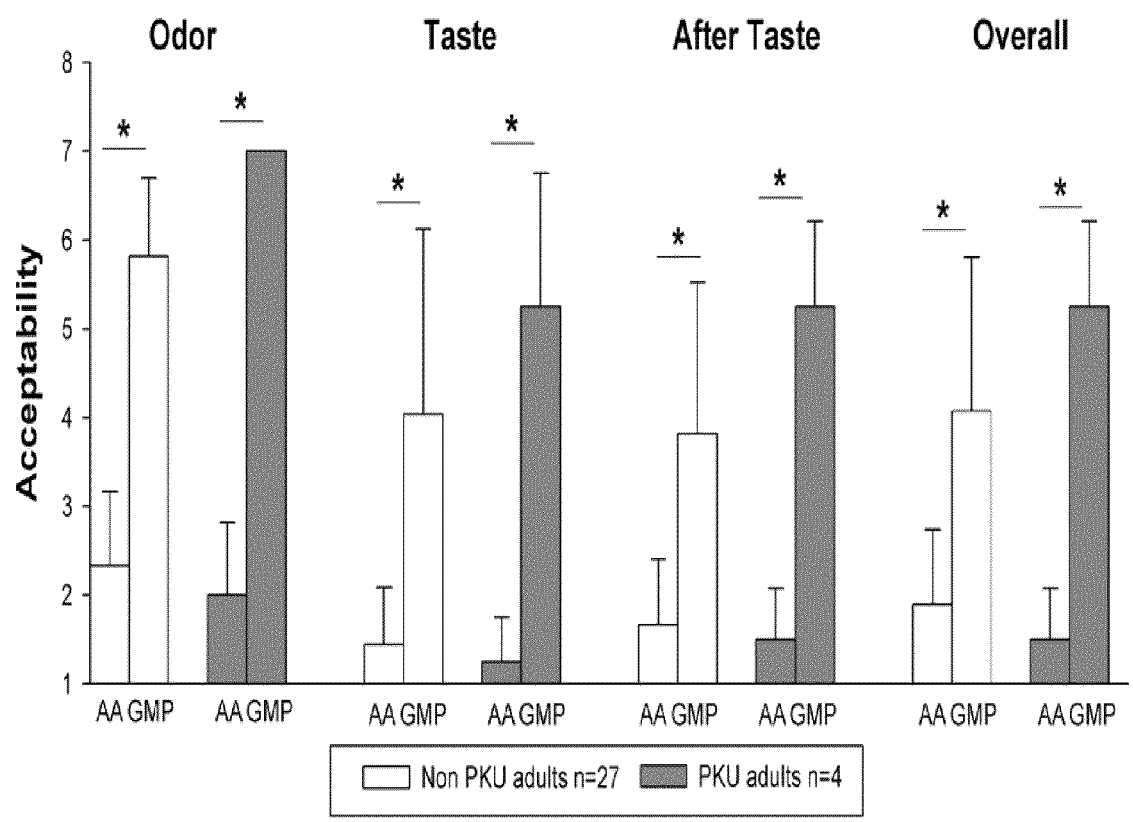
FIG. 11 is a bar graph showing acceptability ratings using four different criteria (odor, taste, after taste, and overall) for both Bettermilk™, a GMP food of the present invention, and Phenex-2™, a commonly used amino acid formula. The ratings are averaged from 27 non PKU adults (unshaded bars) and 4 PKU adults (shaded bars). Values are mean±SD; *p≤0.01, paired t-test. Acceptability ranking is: 1—dislike extremely, 2—dislike a lot, 3—dislike, 4—dislike a little, 5—like a little, 6—like, 7—like a lot, and 8—like extremely.

In the study, 27 non PKU adults and 4 PKU adults sampled both Bettermilk and Phenex-2. Participants then rated the acceptability of each product on a scale of 1-8. 1-dslike extremely; 2-dislike a lot; 3-dislike; 4-dislike a little; 5-like a little; 6-like; 7-like a lot; and 8-like extremely. The results are shown in FIG. 11. As can be seen from the data presented, participants rated the GMP food much higher than the AA formula on all acceptability criteria (odor, taste, after taste, and overall), and the difference in acceptability was substantially greater for the PKU participants as compared to the non PKU participants. This provides further evidence of the advantages of the GMP medical foods of the invention as compared to conventional amino acid formulas.

Example 7

Effects of GMP Foods as Compared with Amino Acids on Ghrelin Levels in Individuals with PKU Given the potential of GMP medical foods to promote satiety, the objective of this study was to assess satiety using a visual analog scale (VAS) and compare plasma concentrations of ghrelin in individuals with PKU fed a breakfast of GMP medical foods as compared to an AA-based breakfast.

Using additional data from the study reported above in Example 4 above, this study demonstrates the ability of a breakfast of GMP foods to promote satiety and affect plasma concentrations of the appetite stimulating hormone ghrelin in those with PKU when compared to an AA-based breakfast. The eleven PKU subjects (8 adults and 3 boys ages 11-14) profiled in Example 4 served as their own controls in an inpatient metabolic study with two 4-day treatments: an AA-based diet followed by a diet replacing all AA formula with GMP foods. Plasma concentration of ghrelin was obtained before and 180 min after breakfast. Satiety was assessed using a visual analog scale before, immediately after and 150 min after breakfast. Postprandial ghrelin concentration was significantly lower (p=0.03) with GMP compared to an AA-based breakfast, with no difference in fasting ghrelin. Lower postprandial ghrelin concentrations were associated with greater feelings of fullness after breakfast suggesting greater satiety with GMP compared to AAs. These results show sustained ghrelin suppression, and suggest greater satiety with ingestion of a meal containing GMP compared with AAs.

Materials and Methods

Plasma Ghrelin Measurements

All postprandial blood samples were drawn 180 min after the start (150 min after completion) of breakfast. For the last six subjects (Subject 6-11) fasting blood samples were also obtained before breakfast on the last 2 days of the AA diet (days 3 and 4) and on the last 2 days of the GMP diet (days 7 and 8). Total plasma ghrelin was measured in fasting (n=6) and postprandial (n=11) samples by radioimmunoassay (Linco Research, St. Charles, Mo.); for each subject equal volumes of plasma were combined for days 3+4 (AA diet) and days 7+8 (GMP diet) as supported by observed stability of the plasma AA profile on these days. Total ghrelin for subject 2 was removed from analysis because the interpolated value was a clear statistical outlier that greatly exceeded the highest concentration on the standard curve.

Motivation-to-Eat VAS Questionnaires

Each subject completed a four-question motivation-to-eat VAS questionnaire three times: before breakfast, immediately following breakfast, and 2 h after finishing breakfast to assess subjective measures of appetite and satiety. Each question consisted of a 100 mm line with opposing statements on either end. Subjects were asked to indicate with a vertical mark where on the line best described their feelings at the time with regards to the following questions: (1) How strong is your desire to eat?, (2) How hungry do you feel?, (3) How full do you feel? and (4) How much food do you think you can eat? (prospective food consumption, PFC). An appetite score to reflect the four questions on the motivationto-eat VAS questionnaire was calculated for each questionnaire using the formula: Appetite score (mm)=[desire to eat+hunger+(100-fullness)+PFC]/4.

Statistical Analysis

All statistical analysis was conducted with the statistical program R for Mac OS X version 2.9 (R Project for Statistical Computing, Wirtschaftsuniversität, Vienna, Austria). Primary analyses were performed using two-tailed paired t-tests, pairing on subject. Tests were considered significant at p<0.05; values are means±SEM. Fasting and postprandial plasma ghrelin values were compared within each diet treatment (e.g., fasting AA vs. postprandial AA) and between the diet treatments (e.g., fasting AA vs. fasting GMP) using a paired t-test, pairing on subject. Motivation-to-eat VAS questionnaires on the last day of the AA diet and the last day of the GMP diet were compared within diets (e.g., fasting AA vs. postprandial AA) and between diets (e.g., fasting AA vs. fasting GMP). Secondary analysis used a linear mixed effects model to examine the effect of: BMI, diet treatment, age, macronutrient intake at breakfast, plasma phe and plasma values (ghrelin, insulin and/or total AAs) on answers to daily VAS questionnaires and gherlin plasma value, controlling for a random subject effect. If there was no subject effect, a fixed effects linear model was used. The best model was found using backward elimination, eliminating insignificant variables.

Results

Motivation-to-Eat VAS Profiles

The motivation-to-eat VAS profiles were not significantly different at any time point between the AA diet (Day 4) and the GMP diet (Day 8). However as expected, the appetite profile significantly changed before, immediately after and 2 h after consuming either the AA or GMP breakfast (data not shown). Protein intake was identified as the most common significant variable for the VAS questionnaires using the mixed effects statistical model. The protein content of breakfast showed a significant negative association with the appetite score immediately after breakfast (p=0.01) such that the appetite score decreased with greater protein intake at breakfast. In the final model for the appetite score immediately after breakfast, other significant factors in addition to protein content included BMI, age and the interaction between diet treatment and the day of the study. BMI significantly affected VAS answers at all time points in the mixed effects model analysis. A higher BMI was associated with a greater desire to eat, hunger, and appetite score and lower feelings of fullness.

Plasma Ghrelin

Figure 12:
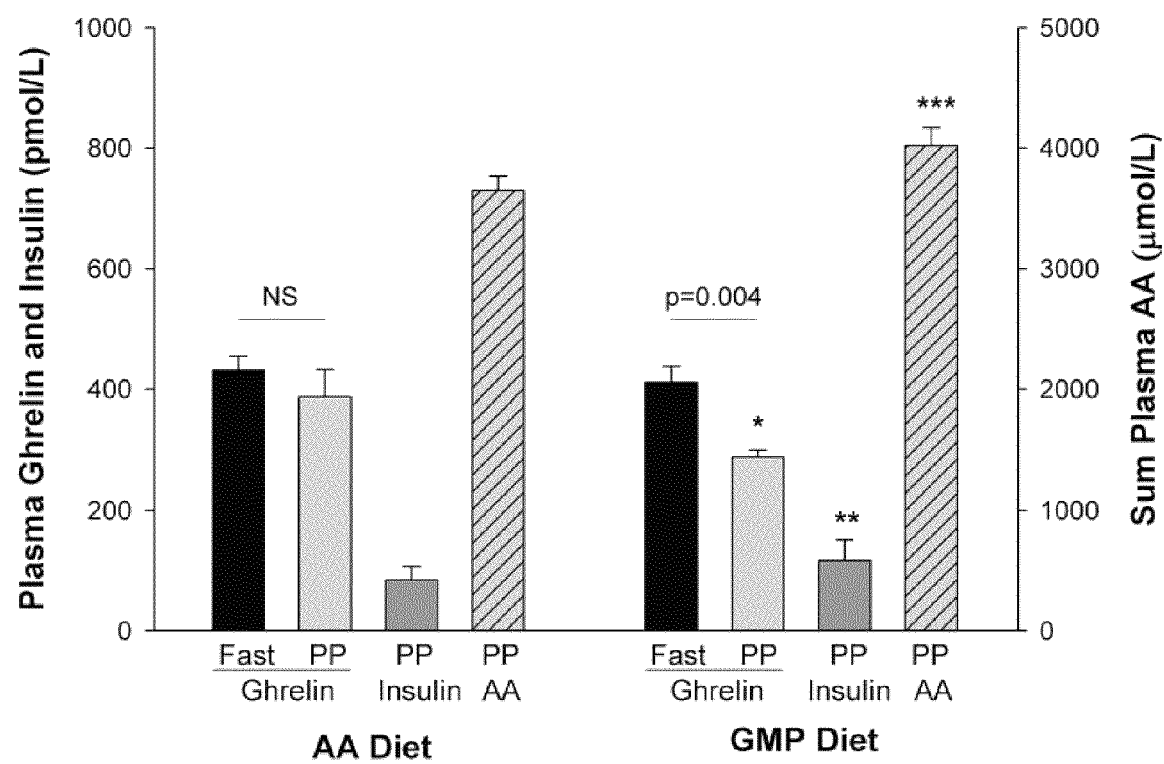
FIG. 12 is a bar graph showing plasma concentrations of ghrelin, insulin and amino acids for PKU subjects when on a GMP diet and on an amino acid diet. Ghrelin and insulin values represent equal volumes of plasma combined for each subject from days 3+4 for the AA breakfast, days 7+8 for the GMP breakfast. Sum of postprandial (PP) plasma AA values on the last day of the AA diet (day 4) and last day of the GMP diet (day 8). All values are means±SEM; n=6 for ghrelin fasting values. *Indicates significantly different from postprandial ghrelin with AA breakfast (p=0.03, paired t-test, pairing on subject; n=10). Indicates moderately significant difference from insulin with the AA breakfast (p=0.053, paired t-test, pairing on subject; n=10). *Indicates significantly different from sum of plasma AAs with the AA breakfast (p=0.049, paired t-test, pairing on subject; n=11).
Figure 13:
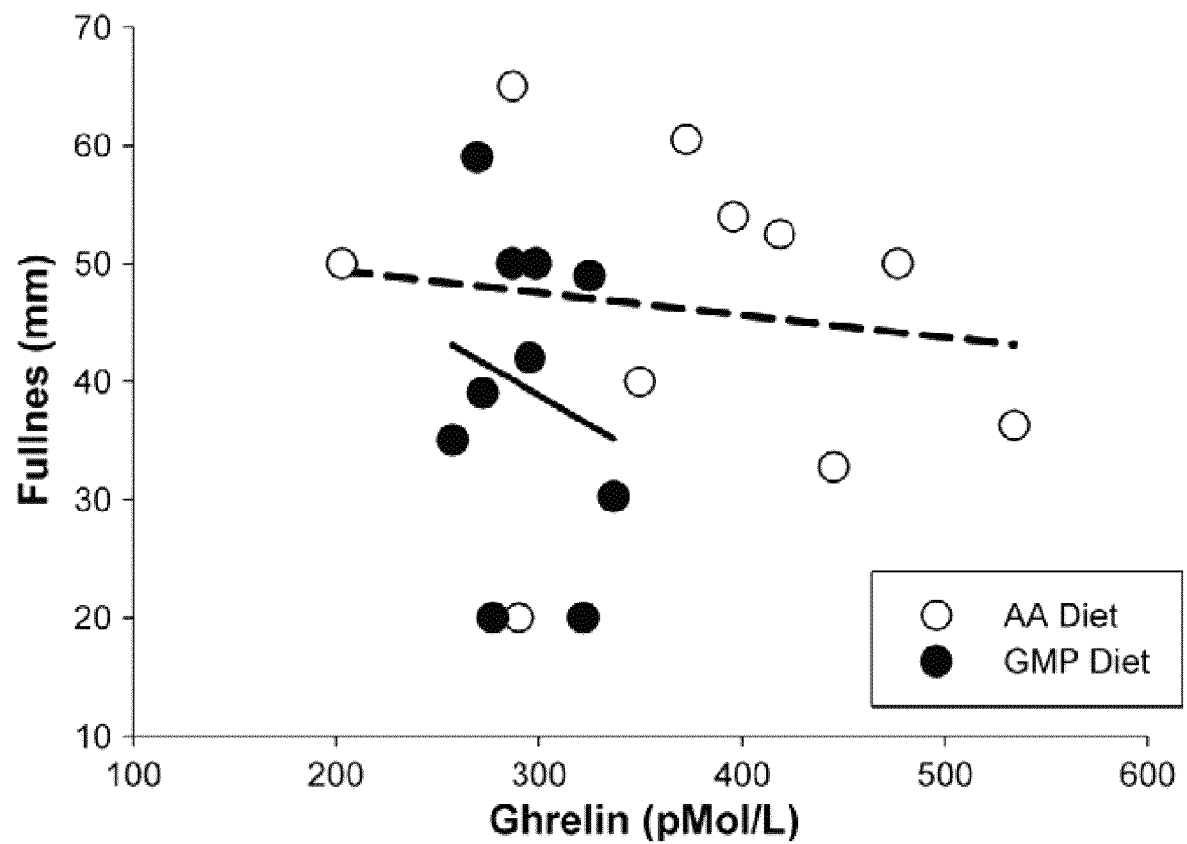
FIG. 13 is a graph of the relationship between plasma ghrelin concentrations 180 min after the start of breakfast (x axis) and feeling of fullness 2 h after breakfast (y axis) for PKU subjects on both GMP (unfilled circles) and amino acid (filled circles) diets. Lower postprandial ghrelin was associated with greater feeling of fullness. Lines represent least squares regression lines fitted to individual diet treatment data; AA breakfast is dashed line and GMP breakfast is solid line. Lines are significantly different. Using backward elimination with a mixed effects model, the best model predicting postprandial fullness scores included diet treatment, postprandial ghrelin and the interaction between ghrelin and diet treatment.

The concentration of ghrelin in plasma obtained after an overnight fast was not significantly different between the AA and GMP diets (see FIG. 12) and there were no significant associations between fasting plasma ghrelin concentrations and a variety of variables. In particular, there was no direct association found between fasting ghrelin and BMI in this diverse sample population. The total concentration of AAs in fasting plasma was also not significantly different between the two diets (data not shown). Postprandial plasma ghrelin concentration, taken 180 min following the start of the AA breakfast, was not different from fasting ghrelin prior to eating the AA breakfast (FIG. 12). In contrast, the GMP breakfast induced significantly lower postprandial plasma ghrelin concentration, an expected response following a meal. In addition, postprandial ghrelin following the GMP breakfast was significantly lower than postprandial ghrelin following the AA breakfast. There were no significant associations between post-prandial ghrelin concentrations and BMI. Using backward elimination with a linear mixed effects model, the only factor predicting postprandial ghrelin was diet treatment, in that postprandial plasma ghrelin was lower with the GMP breakfast. Postprandial plasma ghrelin concentration was a significant factor in the prediction of fullness 2 h after breakfast (see FIG. 13). Higher fullness scores were significantly associated with lower postprandial ghrelin concentrations, diet treatment, and the interaction between ghrelin and diet.

Discussion

The absence of a protein source in a meal may result in increased feelings of hunger throughout the day. The improved taste and preference combined with the ability to make a variety of good tasting foods with GMP supports the notion that GMP may improve the dietary management of PKU by providing a protein source that can be more easily spaced throughout the day. Moreover, we report for the first time that ingestion of intact protein from GMP compared with synthetic AAs results in sustained suppression of ghrelin following a meal in those with PKU.

Ghrelin is the only known orexigenic hormone, with highest concentrations in the fasted state and in anticipation of a meal, whereas concentrations are suppressed following a meal. We found no difference in fasting ghrelin concentration when comparing the AA and GMP breakfasts in 3 children (ages 11-14) and 8 adults with PKU who served as their own control.

The data provide novel information about the response of ghrelin to a meal. We demonstrate that isocaloric breakfast treatments containing the intact protein GMP compared with synthetic AAs induce a different ghrelin response. Ghrelin levels decrease after a meal in proportion to caloric content and protein and carbohydrate suppress ghrelin to a similar extent in studies with isocaloric substitution of 20% energy or greater from protein or carbohydrate. Thus, the higher proportion of energy provided by carbohydrate in the GMP breakfast (7.8%) is unlikely to account for the differential ghrelin response observed in this study.

Ghrelin concentration was only measured at two time points, fasting and 180 min after the start of breakfast, therefore the nadir was likely missed. However, the observed significant decline in ghrelin concentrations between these two time points with the GMP breakfast, but not the AA, shows that the intake of an AA breakfast does not allow sustained suppression of ghrelin 180 min after breakfast. In fact, the ghrelin hunger signal 3 h after the AA meal was no different than after a 12 h fast. Greater ghrelin suppression following a meal with intact protein compared to AAs may be due to variations in the rate of absorption of synthetic AAs compared with GMP. The appearance of AAs in plasma occurs within 1 h following consumption of AAs and approximately 2 h with consumption of a comparable intact protein. Fast absorption of AAs has been shown to negatively affect protein retention and utilization in rats and humans.

Although the most significant consequence of long-term AA consumption may be reduced protein retention, the sharp rise of plasma AAs concentration also affects physiological signals of satiety. The aminostatic hypothesis proposes that an increase in plasma AA concentrations is accompanied by a greater stimulation of GI hormones and decreased appetite followed by a return of appetite when plasma AA concentrations fall (S. M. Mellinkoff, M. Frankland, D. Boyle, M. Greipel, Relationship between serum amino acid concentration and fluctuations in appetite. 1956, Obes. Res. 5 (1997) 381-384). Thus, whey proteins, such as GMP, may decrease appetite due to rapid absorption and sustained levels of plasma AAs, whereas synthetic AAs cause an acute rise in plasma AAs which disappear from plasma faster and to a greater extent compared to intact protein, resulting in increased appetite shortly after a meal. Supportive of this hypothesis, a breakfast containing GMP induced higher total postprandial plasma AA and lower ghrelin concentrations compared with synthetic AAs. Moreover, our data show an association between lower postprandial ghrelin concentration and greater feelings of fullness suggesting that a GMP meal sustains satiety when compared with AAs.

Ghrelin suppression is regulated by postgastric feedback (D. L. Williams, D. E. Cummings, H. J. Grill, J. M. Kaplan, Meal-related ghrelin suppression requires postgastric feedback (Endocrinology 144 (2003) 2765-2767), requiring luminal nutrients in the distal intestine, not in the stomach or duodenum. The rapid rise of plasma AAs following consumption of an AA-based formula suggests that luminal nutrients are present for a shorter time, therefore limiting their ability to suppress ghrelin.

In addition, ghrelin works in a reciprocal manner with insulin (D. E. Cummings, J. Q. Purnell, R. S. Frayo, K. Schmidova, B. E. Wisse, D. S. Weigle, A preprandial rise in plasma ghrelin levels suggests a role in meal initiation in humans, Diabetes 50 (2001) 1714-1719). Similarly, our results show that postprandial plasma insulin concentration is higher and ghrelin lower after a breakfast containing GMP compared with an AA-based breakfast. Thus, GMP foods may improve insulin and ghrelin regulation, satiety signaling, and protein retention in individuals with PKU relative to a conventional amino acid diets.

CONCLUSION

The nutritional management of PKU is in need of new dietary options besides synthetic AAs to facilitate ingestion of a low-phe source of protein throughout the day in order to improve metabolic control and control hunger. These results confirm the importance of protein consumption in a meal to improve satiety, and provide novel evidence that a GMP breakfast suppresses plasma levels of the satiety hormone ghrelin for a longer period of time compared with an AA breakfast. Food products made with the intact, low-phe protein GMP are a first step to providing a more physiologically complete diet that improves dietary options, and facilitates protein distribution and metabolic control of PKU.

Example 8

Recommended Amino Acid Supplementation for the Present Invention

In this prophetic example, the inventors present recommended amino acid supplementation amounts for the present invention. In particular, the inventors provide recommended variations from the supplementation amounts used in the previous working examples.

Methionine.

The inventors do not recommend that methionine be added to the medical foods of the present invention. It has recently been determined that the minimum requirement for methionine plus cysteine for school-age children and adults is significantly lower than previously thought (Turner, et al., Am J Clin Nutr 2006; 83:619-23; Ball, et al., J Nutr 2006; 136 (suppl 2):1682S-93S). This suggests that GMP contains an adequate amount of methionine, and that methionine supplementation is not required. As methionine is a sulfur-containing amino acid with an unpleasant taste, not supplementing the GMP-based foods with methionine will further increase the palatability of the foods.

Arginine.

In contrast to the previously presented examples, the inventors recommend supplementing the GMP in the medical foods of the invention with additional arginine. Specifically, the inventors propose adding arginine to the medical foods of the invention so that the total weight ratio within the food of the arginine to the protein is preferably from about 60 to 90 milligrams arginine/gram total protein, and more preferably about 75 milligrams arginine/gram total protein.

Although arginine is recognized in the art as a nutritionally dispensable amino acid (Tharakan et al., Clin Nutr 2008; 27:513-22), arginine has multiple non-nutritional functions, which include serving as a substrate for synthesis of protein, urea, and nitric oxide (the cofactor for PAH, tetrahydrobiopterin, is also the cofactor for nitric oxide synthetase). Arginine is synthesized in the kidney from intestinal citrulline derived from glutamine and oxidized to ornithine in the urea cycle. Consistent with minimal arginine in GMP, plasma concentrations of arginine and ornithine reported in the clinical trials of Example 4 were significantly lower with ingestion of the GMP compared with the AA diet (see Table 14). Thus, the inventors conclude that GMP should be supplemented with arginine for utilization in the PKU diet.

Leucine.

The inventors recommend that the medical foods of the present invention be supplemented with an amount of leucine that is substantially more than that indicated by any published recommended intake requirement or than amount used in any of the above working examples. Specifically, the inventors propose adding leucine to the medical foods of the invention so that the total weight ratio within the food of leucine to the protein is preferably from about 100 to 200 milligrams leucine/gram total protein, and more preferably about 100 milligrams leucine/gram total protein.

The inventors have determined that elevated plasma levels of leucine may competitively inhibit Phe transport across the intestinal mucosa and blood brain barrier via a certain carrier protein. Thus, leucine supplementation beyond levels of nutritional need may surprisingly reduce Phe levels in both plasma and brain, the primary organ where Phe exerts its neurotoxic effects. The higher recommended leucine levels, then, may lead to decreased levels of Phe in plasma and brain in individuals with PKU using the GMP-based foods of the invention.

Furthermore, recent evidence demonstrates that leucine stimulates synthesis of skeletal muscle protein by enhancement of mRNA translation initiation rates (Norton L E et al., J Nutr 2009; 139:1103-1109 and Crozier, S J et al., J Nutr 2005; 135:376-382). Improved synthesis of skeletal muscle protein in those with PKU would lower blood phe levels and may increase lean body mass.

Tyrosine.

A supplemented amount of tyrosine is not added to medical foods for the treatment of tyrosine metabolism disorders, such as tyrosinemia. For other applications, including for a PKU diet, the inventors recommend that the medical foods of the present invention be supplemented with an amount of tyrosine that is somewhat more than the amount used in any of the above working examples. Specifically, the inventors propose adding tyrosine to non heat-treated medical foods of the invention so that the initial total weight ratio within the food of tyrosine to the protein is preferably from about 62 to 93 milligrams tyrosine/gram total protein, and more preferably about 85 milligrams tyrosine/gram total protein.

Tyrosine is an important AA in the PKU diet because it is indispensable and a precursor of adrenaline, norepinephrine, melanin, and thyroxine. In Example 4 above, the inventors found that concentrations of tyrosine in plasma obtained in the postprandial or fasting samples were not significantly different with ingestion of the GMP or AA diets (see Table 14 above). Concentrations of tyrosine in plasma after an overnight fast were decreased compared with postprandial concentrations with ingestion of both the GMP and the AA diet. However, the GMP diet resulted in a mean fasting tyrosine concentration that was below the normal range. Thus, the inventors recommend tyrosine supplementation above the 150% DRI supplementation level of the foods tested in Example 4.

In addition, in Example 5 above, the inventors found that when the PE contributed by added amino acids were accounted for in the denominator, the corrected calculated values matched the observed values (P>0.05) of all the measured amino acids, except for Tyr (P<0.05) (see Table 20 above, column E compared with F). The lower than expected Tyr value suggests that Tyr degraded at some point during the manufacture or storage process. Although the DRI for Tyr was met in the GMP food (which were supplemented at 150% of DRI), increased Tyr supplementation would provide a higher level of Tyr.

Tryptophan.

A supplemented amount of tryptophan is not added to medical foods for the treatment of tryptophan metabolism disorders, such as hypertryptophanemia. For other applications, including for a PKU diet, the inventors propose optionally adding tryptophan to the medical foods of the invention so that the initial total weight ratio within the food of tryptophan to the protein is preferably from about 12 to 14 milligrams tryptophan/gram total protein, and more preferably about 12 milligrams tryptophan/gram total protein.

In Example 4, the inventors observed a 29% decrease in postprandial plasma trp levels with the GMP compared with AA diet. The trp levels in the GMP diet was well below the range of trp in AA formulas (~15 mg trp/g protein). There is also evidence that trp is important in synthesis of the neurotransmitter, serotonin (Passcuchi et al., Intl J Neuropsychopharmacology (2009), 12:1067-79). Thus, the recommended levels are significantly above both the range established using 130-160% of the recommended minimum intake guidelines published by WHO (World Health Organization, Protein and Amino Acid Requirements in Human Nutrition, Geneva, Switzerland: United Nations University, 2007) or the recommended amount based on 130% of the 2002 DRI (Institute of Medicine, Dietary Reference Intakes for Energy, Carbohydrates, Fiber, Fat, Protein and Amino Acids, Washington, D.C.: National Academy Press, 2002).

Histidine.

A supplemented amount of histidine is not added to medical foods for the treatment of histidine metabolism disorders, such as histidinemia. For other applications, including for a PKU diet, the inventors propose optionally adding histidine to the medical foods of the invention so that the initial total weight ratio within the food of histidine to the protein is preferably from about 20 to 24 milligrams histidine/gram total protein, and more preferably about 23 milligrams histidine/gram total protein. The preferred range is based on 130-160% of the recommended minimum intake guidelines published by WHO (World Health Organization, Protein and Amino Acid Requirements in Human Nutrition, Geneva, Switzerland: United Nations University, 2007). The more preferred value is based on 130% of the 2002 DRI (Institute of Medicine, Dietary Reference Intakes for Energy, Carbohydrates, Fiber, Fat, Protein and Amino Acids, Washington, D.C.: National Academy Press, 2002). Unlike the recommendations for the other amino acids, these recommended values for histidine do not vary from what is contained in the GMP medical foods used in the working examples.

Based on the amino acid supplementation amounts presented in this Example, improved GMP-based medical foods can be produced to provide the needed protein for individuals with PKU while functioning to minimize Phe levels in the blood plasma and brain tissue.

Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. A medical food for the management of a metabolic disorder, comprising glycomacropeptide (GMP) and supplemented amounts of two or more amino acids, wherein one of the supplemented amino acids is arginine and the weight ratio within the medical food of the amino acid arginine to total protein is from about 60 to 90 milligrams arginine/gram total protein, and wherein another of the supplemented amino acids is leucine and the weight ratio within the medical food of the amino acid leucine to total protein is from about 100 to 200 milligrams leucine/gram total protein.

2. The medical food of claim 1, further comprising a supplemented amount of the amino acid tyrosine, and wherein the weight ratio within the medical food of the amino acid tyrosine to total protein is from about 62 to 93 milligrams tyrosine/gram total protein.

3. The medical food of claim 2, wherein the total weight of the supplemented amino acids is from about 22% to 38% of the total weight of protein from the GMP and the supplemented amino acids together.

4. The medical food of claim 2, further comprising a supplemented amount of the amino acids tryptophan and histidine, wherein the total weight of the supplemented amino acids is from about 25% to 42% of the total weight of protein from the GMP and the supplemented amino acids together.

5. The medical food of claim 2, wherein the weight ratio within the medical food of the amino acid arginine to total protein is about 75 milligrams arginine/gram total protein.

6. The medical food of claim 2, wherein the weight ratio within the medical food of the amino acid leucine to total protein is about 100 milligrams leucine/gram total protein.

7. The medical food of claim 2, wherein the weight ratio within the medical food of the amino acid tyrosine to total protein is about 85 milligrams tyrosine/gram total protein.

8. The medical food of claim 1, wherein the medical food does not contain a supplemented amount of the amino acid tyrosine.

9. The medical food of claim 8, wherein the medical food contains less than 2.0 milligrams phenylalanine and tyrosine together per gram total protein.

10. The medical food of claim 8, wherein the total weight of the supplemented amino acids is from about 16% to 29% of the total weight of protein from the GMP and the supplemented amino acids together.

11. The medical food of claim 10, further comprising a supplemented amount of the amino acids tryptophan and histidine, wherein the total weight of the supplemented amino acids is from about 19% to 33% of the total weight of protein from the GMP and the supplemented amino acids together.

12. The medical food of claim 1, wherein the medical food is in the form of a beverage, a bar, a wafer, a pudding, a gelatin, a cracker, a fruit leather, a nut butter, a sauce, a salad dressing, a crisp cereal piece, a flake, a puff, a pellet, or an extruded solid.

13. The medical food of claim 1, wherein the food does not contain supplemented amounts of the amino acid methionine.

14. The medical food of claim 2, wherein the GMP comprises not more than 2.0 milligrams phenylalanine per gram GMP protein, and wherein the medical food contains less than 1.5 milligrams phenylalanine per gram total protein.

15. A method of making a medical food for the management of a metabolic disorder, the method comprising the steps of:
(a) providing glycomacropeptide (GMP) and supplemented amounts of two or more amino acids, wherein one of the supplemented amino acids is arginine and the weight ratio of the amino acid arginine provided to the total protein provided is from about 60 to 90 milligrams arginine/gram total protein, and wherein the second supplemented amino acid is leucine and the weight ratio of the amino acid leucine provided to the total protein provided is from about 100 to 200 milligrams leucine/gram total protein; and
(b) mixing the provided glycomacropeptide (GMP) and supplemented amounts of two or more amino acids with one or more non-protein ingredients to make a food.

16. The method of claim 15, wherein a supplemented amount of a third amino acid, tyrosine, is additionally provided such that the weight ratio of the amino acid tyrosine provided to the total protein provided is from about 62 to 93 milligrams tyrosine/gram total protein.

17. The method of claim 15, wherein the weight ratio of the amino acid arginine provided to the total protein provided is about 75 milligrams arginine/gram total protein.

18. The method of claim 16, wherein the weight ratio of the amino acid tyrosine provided to the total protein provided is about 85 milligrams tyrosine/gram total protein.

19. The method of claim 15, wherein the weight ratio of the amino acid leucine provided to the total protein provided is about 100 milligrams lysine/gram total protein.

20. A method of making a medical food for the management of a metabolic disorder, the method comprising the steps of:
(a) purifying glycomacropeptide (GMP) so that it contains no more than 2.0 mg phenylalanine contaminant per gram GMP protein;
(b) mixing the purified GMP produced in step (a) with:
(i) supplemented amounts of two or more amino acids, wherein one of the supplemented amino acids is arginine and the weight ratio of the amino acid arginine mixed to the total protein mixed is from about 60 to 90 milligrams arginine/gram total protein, and wherein the second supplemented amino acid is leucine and the weight ratio of the amino acid leucine mixed to the total protein mixed is from about 100 to 200 milligrams leucine/gram total protein; and
(ii) one or more non-protein ingredients;
whereby a medical food is made.

21. The method of claim 20, wherein the step of purifying the GMP so that it contains no more than 2.0 mg phenylalanine contaminant per gram GMP protein further comprises the use of one or more of the group consisting of cation exchange chromatography, ultrafiltration, and diafiltration.

22. The method of claim 21, further comprising the step of drying the purified GMP by lyophilization or spray drying.

23. The method of claim 15, further comprising the step of allowing the food to set to form a pudding, a gelatin, or a fruit leather.

24. The method of claim 15, further comprising the step of forming the food into a bar, a cracker, a flake, a puff, or a pellet.

25. The method of claim 15, further comprising the step of extruding the food as an extruded solid.

26. The method of claim 15, wherein tyrosine is not provided.

27. The method of claim 15, further comprising the step of heat-treating the food.

28. The method of claim 27, wherein:
(a) the initial weight ratio of the amino acid arginine provided to total protein provided before heat treatment is greater than about 75 milligrams arginine/gram total protein, and the initial weight ratio of the amino acid leucine to total protein provided before heat treatment is greater than about 100 milligrams leucine/gram total protein; and (b) the final weight ratio of the amino acid arginine to total protein within the food after heat treatment is from about 60 to 90 milligrams arginine/gram total protein, and the final weight ratio of the amino acid leucine to total protein within the food after heat treatment is from about 100 to 200 milligrams leucine/gram total protein.

29. The method of claim 16, further comprising the step of heat-treating the food.

30. The method of claim 29, wherein:

(a) the initial weight ratio of the amino acid leucine to total protein provided before heat treatment is greater than about 100 milligrams leucine/gram total protein, the initial weight ratio of the amino acid tyrosine provided to total protein provided before heat treatment is greater than about 85 milligrams tyrosine/gram total protein, and the initial weight ratio of the amino acid arginine provided to total protein provided within the medical food before heat treatment is greater than about 75 milligrams arginine/gram total protein; and (b) the final weight ratio of the amino acid leucine to total protein within the food after heat treatment is from about 100 to 200 milligrams leucine/gram total protein, the final weight ratio of the amino acid tyrosine to total protein within the food after heat treatment is from about 62 to 93 milligrams tyrosine/gram total protein, and the final weight ratio of the amino acid arginine to total protein within the food after heat treatment is from about 60 to 90 milligrams arginine/gram total protein.

31. The method of claim 30, wherein:

(a) supplemented amounts of the amino acids tryptophan and histidine are also provided, such that the initial weight ratio of the amino acid tryptophan provided to total protein provided before heat treatment is greater than about 12 milligrams tryptophan/gram total protein, and the initial weight ratio of the amino acid histidine provided to total protein provided before heat treatment is greater than about 23 milligrams histidine/gram total protein; and (b) the final weight ratio of the amino acid tryptophan to total protein within the food after heat treatment is from about 12 to 14 milligrams tryptophan/gram total protein, and the weight ratio of the amino acid histidine to total protein within the food after heat treatment is from about 20 to 24 milligrams histidine/gram total protein.

32. A method of treating a metabolic disorder, comprising administering to a human having a metabolic disorder a medical food comprising glycomacropeptide (GMP), a supplemented amount of the amino acid arginine, wherein the weight ratio within the medical food of the amino acid arginine to the total protein is from about 60 to 90 milligrams arginine/gram total protein, and a supplemented amount of the amino acid leucine, wherein the weight ratio within the medical food of leucine to the total protein is from about 100 to 200 milligrams leucine/gram total protein, and wherein the metabolic disorder is selected from a Phenylalanine metabolism disorder, a Tyrosine metabolism disorder, a Tryptophan metabolism disorder, and a Histidine metabolism disorder.

33. The method of claim 32, wherein the medical food further comprises a supplemented amount of the amino acid tyrosine, such that the weight ratio within the medical food of the amino acid tyrosine to the total protein is from about 62 to 93 milligrams tyrosine/gram total protein.

34. The method of claim 32, wherein the medical food does not contain a supplemented amount of the amino acid tyrosine.

35. The method of claim 34, wherein the medical food contains less than 2.0 milligrams phenylalanine and tyrosine together per gram total protein.

36. The method of claim 33, wherein the medical food does not contain a supplemented amount of the amino acid phenylalanine, and wherein the metabolic disorder is the Phenylalanine metabolism disorder Phenylketonuria (PKU).

37. The method of claim 36, wherein the medical food contains less than 1.5 milligrams phenylalanine per gram total protein.

38. The method of claim 33, wherein the human to which the medical food is administered is at least two years old.

39. The method of claim 34, wherein the metabolic disorder is selected from the group consisting of the Tyrosine metabolism disorders Type I tyrosinemia, Type II tyrosinemia, Type III tyrosinemia/Hawkinsinuria, and Alkaptonuria/Ochronosis.

40. The medical food of claim 1, wherein the two or more supplemented amino acids are all selected from the group consisting of arginine, leucine, tyrosine, tryptophan and histidine, and wherein no other supplemented amino acids are present.

41. The medical food of claim 40, wherein the supplemented amino acids include tyrosine, and wherein the weight ratio within the medical food of the amino acid tyrosine to total protein is from about 62 to 93 milligrams tyrosine/gram total protein.

42. The medical food of claim 41, wherein the supplemented amino acids include both tryptophan and histidine, and wherein the total weight of the supplemented amino acids is from about 25% to 42% of the total weight of protein from the GMP and the supplemented amino acids together.

* * * * *